US011731962B2

(12) United States Patent
Teng et al.

(10) Patent No.: US 11,731,962 B2
(45) Date of Patent: Aug. 22, 2023

(54) LPXC INHIBITOR AND METHODS OF MAKING

(71) Applicant: Blacksmith Medicines, Inc., San Diego, CA (US)

(72) Inventors: Min Teng, San Diego, CA (US); Baskar Nammalwar, San Diego, CA (US); David T. Puerta, San Diego, CA (US)

(73) Assignee: BLACKSMITH MEDICINES, INC., San Diego, CA (US)

( * ) Notice: Subject to any disclaimer, the term of this patent is extended or adjusted under 35 U.S.C. 154(b) by 115 days.

(21) Appl. No.: 17/211,029

(22) Filed: Mar. 24, 2021

(65) Prior Publication Data
US 2021/0309651 A1 Oct. 7, 2021

Related U.S. Application Data

(60) Provisional application No. 63/153,152, filed on Feb. 24, 2021, provisional application No. 62/994,654, filed on Mar. 25, 2020.

(51) Int. Cl.
C07D 413/14 (2006.01)
(52) U.S. Cl.
CPC ................... *C07D 413/14* (2013.01)
(58) Field of Classification Search
CPC .. C07D 239/36; C07D 403/10; C07D 403/12; C07D 403/14
See application file for complete search history.

(56) References Cited

U.S. PATENT DOCUMENTS

| | | | |
|---|---|---|---|
| 5,543,534 A | 8/1996 | Vuligonda et al. | |
| 5,846,514 A | 12/1998 | Foster et al. | |
| 6,334,997 B1 | 1/2002 | Foster et al. | |
| 6,699,849 B1 | 3/2004 | Loftsson et al. | |
| 7,579,486 B2 | 8/2009 | Puerta et al. | |
| 7,786,316 B2 | 8/2010 | Puerta et al. | |
| 9,145,381 B2 | 9/2015 | Fanelli et al. | |
| 10,130,714 B2 | 11/2018 | Wong et al. | |
| 10,414,735 B2 | 9/2019 | Teng et al. | |
| 10,611,747 B2 | 4/2020 | Teng et al. | |
| 10,875,832 B2 | 12/2020 | Teng et al. | |
| 11,021,471 B2 | 6/2021 | Teng et al. | |
| 11,407,740 B2 | 8/2022 | Teng et al. | |
| 2003/0181472 A1 | 9/2003 | Clark et al. | |
| 2003/0190608 A1 | 10/2003 | Blackburn | |
| 2005/0009101 A1 | 1/2005 | Blackburn | |
| 2007/0117848 A1 | 5/2007 | Puerta et al. | |
| 2007/0149556 A1 | 6/2007 | Mikamiyama et al. | |
| 2012/0035255 A1 | 2/2012 | Fanelli et al. | |
| 2012/0041032 A1 | 2/2012 | Puerta et al. | |
| 2012/0329741 A1 | 12/2012 | Oyelere et al. | |
| 2014/0038990 A1 | 2/2014 | Buschmann et al. | |
| 2014/0079666 A1 | 3/2014 | Webb et al. | |
| 2015/0202208 A1 | 7/2015 | Kiyama et al. | |
| 2017/0088532 A1 | 3/2017 | Cohen et al. | |
| 2017/0290918 A1 | 10/2017 | Honda et al. | |
| 2018/0327365 A1 | 11/2018 | Teng et al. | |
| 2019/0106398 A1 | 4/2019 | Cohen et al. | |
| 2020/0095236 A1 | 3/2020 | Teng et al. | |
| 2021/0078957 A1 | 3/2021 | Teng et al. | |
| 2021/0221796 A1 | 7/2021 | Teng et al. | |
| 2021/0315902 A1 | 10/2021 | Teng et al. | |
| 2022/0324846 A1 | 10/2022 | Teng et al. | |

FOREIGN PATENT DOCUMENTS

| | | |
|---|---|---|
| CN | 105777464 A | 7/2016 |
| EP | 2181985 B1 | 10/2011 |
| WO | WO-9830205 A1 | 7/1998 |
| WO | WO-2004062601 A2 | 7/2004 |
| WO | WO-2005110399 A2 | 11/2005 |
| WO | WO-2006028523 A2 | 3/2006 |
| WO | WO-2008027466 A1 | 3/2008 |
| WO | WO-2008045668 A1 | 4/2008 |
| WO | WO-2008154642 A2 | 12/2008 |
| WO | WO-2010059838 A2 | 5/2010 |
| WO | WO-2010100475 A1 | 9/2010 |
| WO | WO-2012151567 A1 | 11/2012 |
| WO | WO-2012177638 A1 | 12/2012 |
| WO | WO-2013151923 A1 | 10/2013 |
| WO | WO-2014117090 A1 | 7/2014 |
| WO | WO-2014160649 A1 | 10/2014 |
| WO | WO-2015024010 A2 | 2/2015 |
| WO | WO-2015085238 A1 | 6/2015 |
| WO | WO-2015099107 A1 | 7/2015 |
| WO | WO-2017083431 A2 | 5/2017 |
| WO | WO-2017083434 A1 | 5/2017 |

(Continued)

OTHER PUBLICATIONS

Aytemir et al. Synthesis and Evaluation of Anticonvulsant and Antimicrobial Activities of 3-Hydroxy-6-methyl-2-substituted 4H-Pyran-4-one Derivatives. Archiv Der Pharmazie 337(5):281-288 (2004).
Banker et al. Modern Pharmaceutics. 3rd ed. Marcel Dekker, New York.p. 596 (1996).
Berge et al. Pharmaceutical Salts. Journal of Pharmaceutical Sciences 66(1):1-19 (Jan. 1977).
Bingi et al. One-pot catalyst free synthesis of novel kojic acid tagged 2-aryl/alkyl substituted-4H-chromenes and evaluation of their antimicrobial and anti-biofilm activities. Bioorganic & Medicinal Chemistry Letters 25(9):1915-1919 (2015).
Bundgaard et al. Design of Prodrugs pp. 7-9, 21-24 (1985).
Di Francesco et al. Development of 2-t butyl-N-methyl pyrimidones as potent inhibitors of HIV integrase. Bioorg Med Chem Lett 18(8):2709-13 (2008).
Ding et al. Design, synthesis and biological evaluation of LpxC inhibitors with novel hydrophilic terminus. Chinese Chemical Letters 26(6):763-767 (2015).

(Continued)

*Primary Examiner* — Deepak R Rao
(74) *Attorney, Agent, or Firm* — Wilson Sonsini Goodrich & Rosati

(57) ABSTRACT

Provided herein is an LpxC inhibitor compound, as well as methods of making and pharmaceutical compositions comprising said compound, and methods of use thereof in the treatment of disease that would benefit from treatment with an LpxC inhibitor, including gram-negative bacterial infections such as urinary tract infections and the like.

18 Claims, No Drawings

(56) References Cited

FOREIGN PATENT DOCUMENTS

| WO | WO-2018208985 A2 | 11/2018 |
|---|---|---|
| WO | WO-2018208987 A2 | 11/2018 |
| WO | WO-2019154412 A1 | 8/2019 |
| WO | WO-2020061375 A1 | 3/2020 |
| WO | WO-2020102572 A1 | 5/2020 |
| WO | WO-2021195258 A1 | 9/2021 |
| WO | WO-2021195260 A1 | 9/2021 |

OTHER PUBLICATIONS

Emami et al. Mannich bases of 7-piperazinylquinolones and kojic acid derivatives: Synthesis, in vitro antibacterial activity and in silico study. EP J Med Chem 68:185-191 (2010).
Evans. Synthesis of radiolabeled compounds. J Radioanal Chern 64(1-2):9-32 (1981).
Garrett et al. The Art of Meeting Palladium Specifications in Active Pharmaceutical Ingredients Produced by Pd-Catalyzed Reactions. Adv. Synth. Catal. 346:889-900 (2004).
Guideline on the Specification Limits for Residues of Metal Catalysts. European Medicines Agency. Pre-authorization Evaluation of Medicines for Human Use, London (Jan. 2007) (pp. 1-32).
Hale et al. Exploring the UDP pocket of LpxC through amino acid analogs. Bioorg Med Chem Lett. 23:2362-2367 (2013).
Kabalka et al. The Synthesis of Radiolabeled Compounds via Organometallic Intermediates. Tetrahedron 45(21):6601-6621 (1989).
Krivonogov et al. Aminomethylation of pyrimidines. Russian Journal of Organic Chemistry 36(8):1219-1224 Chemical Abstracts CAS No. 345959-90-2P (2000).
Li et al. Design, synthesis and biological evaluation of 2-substituted 3-hydroxy-6-methyl-4H-pyran-4-one derivatives as Pseudomonas aeruginosa biofilm inhibitors. Eur J Med Chem 158:753-766 (2018).
Lin et al. Inhibition of LpxC protects mice from resistant Acinetobacter baumannii by modulating inflammation and enhancing phagocytosis. Mbio 3(5):pii:e00312-12 (2012).
Montgomery et al. Pyridone methylsulfone hydroxamate LpxC inhibitors for the treatment of serious gram-negative infections. J Med Chem 55:1662-1670 (2012).
PCT/US2016/061195 International Search Report and Written Opinion dated Jul. 31, 2017.
PCT/US2016/061198 International Search Report and Written Opinion dated Feb. 15, 2017.
PCT/US2018/031896 International Search Report and Written Opinion dated Nov. 7, 2018.
PCT/US2018/031898 International Search Report and Written Opinion dated Nov. 7, 2018.
PCT/US2019/051986 International Search Report and Written Opinion dated Jan. 3, 2020.
PCT/US2019/052021 International Search Report and Written Opinion dated Jan. 6, 2020.
PCT/US2019/061529 International Search Report and Written Opinion dated Mar. 13, 2020.
PCT/US2021/023948 International Search Report and Written Opinion dated Jun. 10, 2021.
PCT/US2021/023950 International Search Report and Witten Opinion dated Jul. 28, 2021.
Ravin. Chapter 76: Preformulation. Remington's Pharmaceutical Sciences, 17th ed., Mack Publishing Company, Easton, Pa. (pp. 1409-1423) (1985).
Storr et al., Vanadyl-thiazolidinedione combination agents for diabetes therapy. Bioconjugate Chemistry 14(1):212-221 (2003).
Us et al. 4H-Pyran-4-one derivatives:; leading molecule for preparation of compounds with antimycobacterial potential. Turkish Journal of Chemistry 30:803-812 (2009).
Us et al. Mannich base derivatives of 3-hydroxy-6- methyl-4H-pyran-4-one with antimicrobial activity. Turkish Journal of Chemistry 33:447-456 (2010).
Vaara: Antibiotic-supersusceptible mutants of *Escherichia coli* and *Salmonella typhimurium*. Antimicrob Agents Chemother. 37(11):2255-2260 (1993).
Wolff, (ed.), Burger's Medicinal Chemistry and Drug Discovery, Fifth Edition, vol. 1: Principles and Practice, San Diego, California, John Wiley & Sons, 1994, pp. 975-977. (4 pages).
Yan et al. Synthesis of hydroxypyrone- and hydroxythiopyrone-based matrix metalloproteinase inhibitors: Developing a structure-activity relationship. Bioorg. Med. Chem. Lett. 19(7):1970-1976 (2009).
Young et al.: Leakage of periplasmic enzymes from envA1 strains of *Escherichia coli*. J. Bacteriol.173(12):3609-3614 (1991).
PCT/US2022/044710 International Search Report and Written Opinion dated Jan. 16, 2023.
Wuts et al. Greene's Protective Groups in Organic Synthesis. 4th ed., Wiley & Sons (pp. 1-1082) (2007).

LPXC INHIBITOR AND METHODS OF MAKING

CROSS-REFERENCE

This application claims the benefit of U.S. Provisional Patent Application No. 62/994,654, filed Mar. 25, 2020, and U.S. Provisional Patent Application No. 63/153,152, filed Feb. 24, 2021, each of which is incorporated herein by reference in its entirety.

STATEMENT AS TO FEDERALLY SPONSORED RESEARCH

This invention was made with government support under AI120246 awarded by the National Institutes of Health. The government has certain rights in the invention.

BACKGROUND

A need exists in the medicinal arts for the effective treatment of illness caused by bacterial infection.

BRIEF SUMMARY OF THE INVENTION

Provided herein is an LpxC inhibitor compound, as well as methods of making and pharmaceutical compositions comprising said compound, and methods of use thereof in the treatment of disease that would benefit from treatment with an LpxC inhibitor, including gram-negative bacterial infections such as urinary tract infections and the like.

In one aspect, disclosed herein is a process for the preparation of Formula 15:

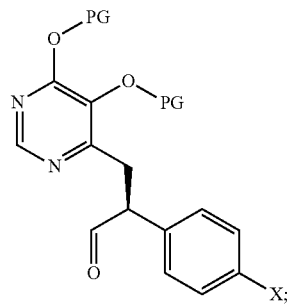

Formula 15 wherein X is halogen, —OTf, —OTs, or —OMs; and each PG is a suitable protecting group;
comprising:
(1) contacting the compound of Formula 14:

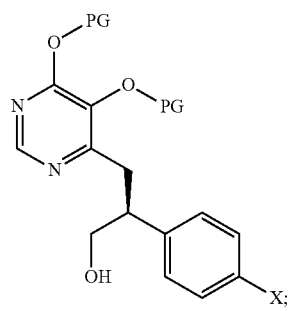

Formula 14 wherein X is halogen, —OTf, —OTs, or —OMs; and each PG is a suitable protecting group;
with a suitable oxidation reagent system in a suitable solvent to provide a compound of Formula 15.

In some embodiments, the suitable oxidation reagent system of step (1) is a TEMPO/bleach system; and the suitable solvent of step (1) is acetonitrile, dichloromethane, chloroform, dichloroethane, hexanes, water, or a combination thereof. In some embodiments, the suitable oxidation reagent system of step (1) comprises catalytic TEMPO and stoichiometric bleach; and the suitable solvent of step (1) is a mixture of water and dichloromethane. In some embodiments, step (1) is performed at a temperature of from about 0° C. to about 5° C.

In some embodiments, the compound of Formula 14 is prepared by:
(1a) contacting a compound of Formula 13:

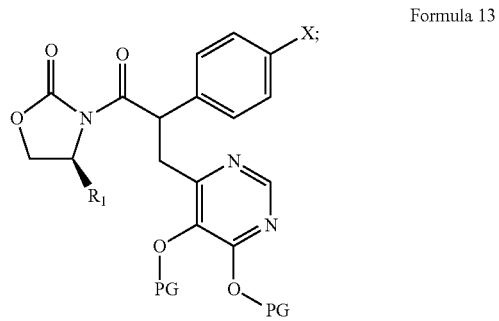

Formula 13 wherein X is halogen, —OTf, —OTs, or —OMs;
$R_1$ is $C_1$-$C_{10}$ alkyl, aryl, or benzyl; and
each PG is a suitable protecting group;
with a suitable borohydride reagent in a suitable solvent to provide the compound of Formula 14.

In some embodiments, the suitable borohydride reagent of step (1a) is lithium borohydride, sodium borohydride, sodium cyanoborohydride, potassium borohydride, lithium triethylborohydride, or sodium triacetoxyborohydride; and the suitable solvent of step (1a) is acetonitrile, methanol, ethanol, isopropyl alcohol, dimethoxyethane, 2-methyltetrahydrofuran, methyl tert-butyl ether, cyclopentyl methyl ether, tetrahydrofuran, diethyl ether, diisopropyl ether, 1,4-dioxane, toluene, water, or a combination thereof. In some embodiments, the suitable borohydride reagent of step (1a) is lithium borohydride; and the suitable solvent of step (I a) is a mixture of tetrahydrofuran and ethanol. In some embodiments, the step (1a) is performed at a temperature of from about 0° C. to about 25° C.

In some embodiments, the process further comprises crystallizing the compound of Formula 14. In some embodiments, the compound of Formula 14 is crystallized from acetonitrile, methanol, ethanol, isopropyl alcohol, acetone, methyl acetate, ethyl acetate, dichloromethane, chloroform, diethyl ether, diisopropyl ether, tert-butyl methyl ether, tetrahydrofuran, 2-methyltetrahydrofuran, dioxane, benzene, toluene, petroleum ether, pentane, hexane, heptane, cyclohexane, acetic acid, water, or a mixture thereof. In some embodiments, the compound of Formula 14 is crystallized from a mixture of isopropyl alcohol and water.

In some embodiments, the compound of Formula 13 is prepared by:

(1b) contacting a compound of Formula 12:

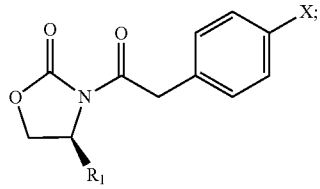

Formula 12 wherein X is halogen, —OTf, —OTs, or —OMs; and
R₁ is $C_1$-$C_{10}$ alkyl, aryl, or benzyl;
with a compound of Formula 9:

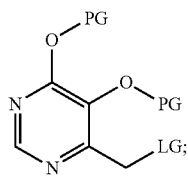

Formula 9 wherein LG is a suitable leaving group; and
each PG is a suitable protecting group;
in the presence of a suitable base, and in a suitable solvent, to provide a compound of Formula 13.

In some embodiments, the suitable base of step (1b) is n-butyl lithium, lithium diisopropylamide (LDA), lithium bis(trimethylsilyl)amide (LiHMDS), or lithium tetramethylpiperidide (LiTMP); and the suitable solvent of step (1 b) is diethyl ether, diisopropyl ether, tetrahydrofuran, 2-methyltetrahydrofuran, 1,4-dioxane, tert-butyl methyl ether, cyclopropyl methyl ether, or a combination thereof. In some embodiments, the suitable base of step (1 b) is LiHDMS; and the suitable solvent of step (1b) is tetrahydrofuran. In some embodiments, step (1b) is performed at a temperature of about −25 to about −15° C. In some embodiments, in step (1b), the compound of Formula 12 is reacted with the base for from about 15 min to about 60 min before the addition of the compound of Formula 9.

In some embodiments, the process further comprises (2) contacting the compound of Formula 15 with a compound of Formula 16, or a salt thereof:

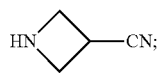

Formula 16 in the presence of a suitable reducing agent in a suitable solvent to provide a compound of Formula 17:

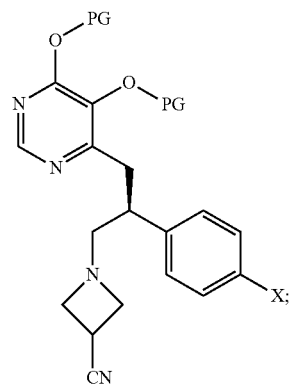

Formula 17 wherein X is halogen, —OTf, —OTs, or —OMs; and
each PG is a suitable protecting group.

In some embodiments, the suitable reducing agent of step (2) is sodium borohydride, sodium cyanoborohydride, sodium triacetoxyborohydride, lithium cyanoborohydride, $H_2$/catalyst, or picoline-borane; and the suitable solvent of step (2) is acetonitrile, methanol, ethanol, dichloromethane, chloroform, dichloroethane, toluene, water, or a combination thereof. In some embodiments, the suitable reducing agent of step (2) is picoline-borane; and the suitable solvent of step (2) is a mixture of methanol and dichloromethane. In some embodiments, step (2) is performed at a temperature of from about 0° C. to about 25° C.

In some embodiments, the process further comprises (3) contacting the compound of Formula 17 with a compound of Formula 20, or a salt thereof:

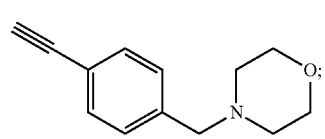

Formula 20 in the presence of a coupling catalyst, a suitable base, and in a suitable solvent to provide a compound f Formula 21:

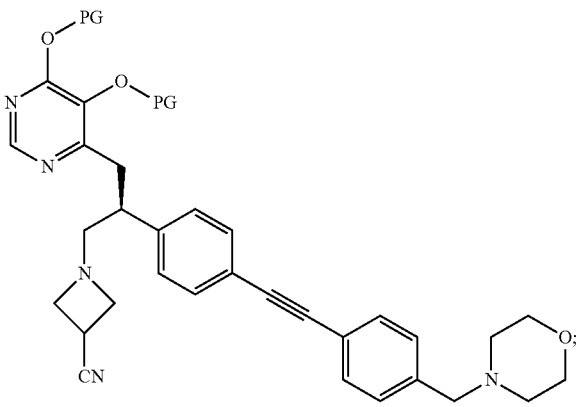

Formula 21 wherein each PG is a suitable protecting group.

In some embodiments, the coupling catalyst of step (3) is a palladium catalyst; the suitable base of step (3) is sec-butylamine or tetrabutylammonium fluoride (TBAF); and the suitable solvent of step (3) is acetonitrile, dimethylformamide, diethyl ether, ethanol, tetrahydrofuran, isopropyl alcohol, 1,4-dioxane, toluene, water, or a combination thereof. In some embodiments, the coupling catalyst of step (3) is a palladium catalyst; the suitable base of step (3) is sec-butylamine; and the suitable solvent of step (3) is water. In some embodiments, step (3) is performed at a temperature of about 40-45° C.

In some embodiments, the process further comprises (4) contacting the compound of Formula 21 with a suitable reagent in a suitable solvent to provide (S)-1-(3-(5,6-dihydroxypyrimidin-4-yl)-2-(4-((4-(morpholinomethyl)phenyl)ethynyl)phenyl)propyl)azetidine-3-carbonitrile (Compound A):

(Compound A)

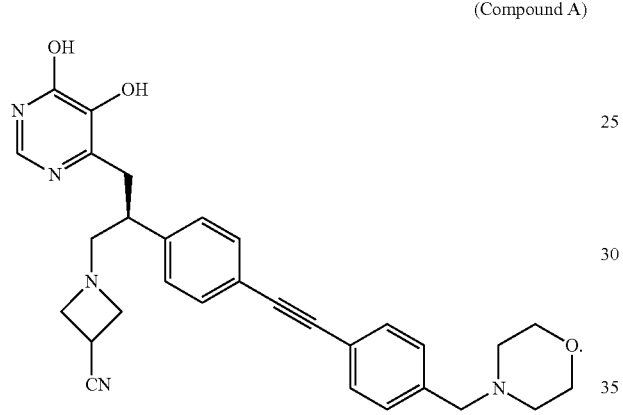

In some embodiments, the suitable reagent of step (4) is H$_2$/catalyst, HCl, HBr, TFA, TBAF, BCl$_3$, 9-I-BBN, BF$_3$—OEt$_2$, TMS-Cl, or TMS-Br, and the suitable solvent of step (4) is acetonitrile, dichloromethane, chloroform, dichloroethane, diethyl ether, tetrahydrofran, isopropyl alcohol, 1,4-dioxane, toluene, anisole, water, or a combination thereof. In some embodiments, the suitable reagent of step (4) is TFA; and the suitable solvent of step (4) is anisole. In some embodiments, step (4) further comprises pentamethylbenzene.

In some embodiments, the process further comprises crystallizing Compound A. In some embodiments, Compound A is crystallized from acetonitrile, methanol, ethanol, isopropyl alcohol, acetone, methyl acetate, ethyl acetate, dichloromethane, chloroform, diethyl ether, diisopropyl ether, tert-butyl methyl ether, tetrahydrofuran, 2-methyltetrahydrofuran, dioxane, benzene, toluene, petroleum ether, pentane, hexane, heptane, cyclohexane, acetic acid, water, or a mixture thereof. In some embodiments, Compound A is crystallized from a mixture of ethyl acetate and tetrahydrofuran.

In some embodiments, the process further comprises treatment of the compound of Formula 21 with a metal scavenger. In some embodiments, the process further comprises treatment of Compound A with a metal scavenger. In some embodiments, the metal scavenger comprises SiO$_2$, charcoal, aqueous solution of L-cysteine, a Silicycle metal scavenger, Si-thiol, SiliaBond DMT, SiliaBond Cysteine, or 3-mercaptopropyl ethyl sulfide silica.

In some embodiments, LG is a halogen, a sulfonate, or a sulfate. In some embodiments, LG is Cl, Br, I, —OTf, —OTs, or —OMs.

In some embodiments, each —O-PG is a benzyl ether, an acetal, or a silyl ether, wherein each PG is the same protecting group. In some embodiments, each PG is benzyl, p-methoxybenzyl, methoxymethyl, [2-(trimethylsilyl)ethoxy]methyl, triisopropylsilyl, or tert-butyldimethylsilyl.

In some embodiments, X is Cl, Br, I, —OTf, —OTs, or —OMs. In some embodiments, X is Cl, Br, or I.

In some embodiments, R$_1$ is methyl, isopropyl, tert-butyl, phenyl, or benzyl.

In some embodiments, LG is Br, each PG is Bn; X is I; and R$_1$ is benzyl.

In another aspect, disclosed herein is a process for the preparation of a compound of Formula 4:

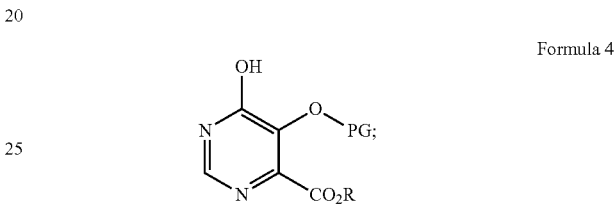

Formula 4 wherein PG is a suitable protecting group; and
R is C$_1$-C$_{10}$ alkyl;
comprising:
(1) contacting the compound of Formula 3:

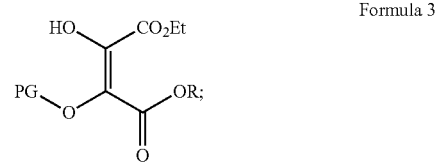

Formula 3 wherein PG is a suitable protecting group; and
R is C$_1$-C$_{10}$ alkyl;
with formamidine acetate and a suitable base in a suitable solvent to provide the compound of Formula 4.

In some embodiments, the suitable base of step (1) is sodium hydride, sodium methoxide, sodium ethoxide, lithium methoxide, lithium ethoxide, n-butyl lithium, lithium diisopropylamide (LDA), lithium bis(trimethylsilyl)amide (LiHMDS), or lithium tetramethylpiperidide (LiTMP); and the suitable solvent of step (I b) is methanol, ethanol, isopropyl alcohol, diethyl ether, diisopropyl ether, tetrahydrofuran, 2-methyltetrahydrofuran, 1,4-dioxane, tert-butyl methyl ether, cyclopropyl methyl ether, or a combination thereof. In some embodiments, the suitable base of step (1) is sodium ethoxide; and the suitable solvent of step (1) is ethanol. In some embodiments, step (1) is performed at a temperature of about 0° C. to 10° C.

In some embodiments, the process further comprises (2) contacting the compound of Formula 4 with a halogenating agent and a suitable base in a suitable solvent to provide the compound of Formula 5:

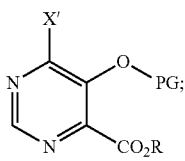

Formula 5

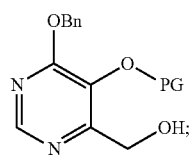

Formula 8-I wherein PG is a suitable protecting group; and

R is $C_1$-$C_{10}$ alkyl; and

X' is Cl or Br.

In some embodiments, the halogenating agent of step (2) is $POCl_3$, $POBr_3$, or $SOCl_2$; the suitable base of step (2) is triethylamine, diisopropylethylamine, sec-butylamine, 1,2,2,6,6-pentamethylpiperidine, tributylamine, or 1,8-diazabicyclo[5.4.0]undec-7-ene (DBU); and the suitable solvent of step (2) is acetonitrile, dichloromethane, chloroform, dichloroethane, toluene, or a combination thereof. In some embodiments, the suitable halogenating agent of step (2) is $POCl_3$; the suitable base of step (2) is triethylamine; and the suitable solvent of step (2) is toluene. In some embodiments, step (1) is performed at a temperature of about 85° C. to 95° C.

In some embodiments, the process further comprises (3) contacting the compound of Formula 5 with benzyl alcohol in the presence of a suitable base, and in a suitable solvent to provide a compound of F

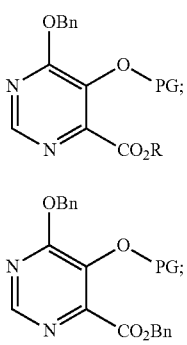

Formula 6-I

Formula 7-I wherein PG is a suitable protecting group; and

R is $C_1$-$C_{10}$ alkyl.

In some embodiments, the suitable base of step (3) is triethylamine, diisopropylethylamine, sec-butylamine, 1,2,2,6,6-pentamethylpiperidine, tributylamine, or 1,8-diazabicyclo[5.4.0]undec-7-ene (DBU); and the suitable solvent of step (3) is acetonitrile, dimethylformamide, diethyl ether, ethanol, tetrahydrofuran, isopropyl alcohol, 1,4-dioxane, toluene, water, or a combination thereof. In some embodiments, the suitable base of step (3) is DBU; and the suitable solvent of step (3) is acetonitrile. In some embodiments, step (3) is performed at a temperature of about 20° C. to 25° C.

In some embodiments, the process further comprises (4) contacting the compound of Formula 6-I or Formula 7-I, or combination thereof with a suitable reducing agent in a suitable solvent to provide a compound of Formula 8-I:

wherein PG is a suitable protecting group.

In some embodiments, the reducing agent of step (4) is sodium borohydride, sodium cyanoborohydride, sodium triacetoxyborohydride, or lithium cyanoborohydride; and the suitable solvent of step (4) is acetonitrile, dimethylformamide, diethyl ether, methanol, ethanol, tetrahydrofuran, isopropyl alcohol, 1,4-dioxane, toluene, water, or a combination thereof. In some embodiments, the reducing agent of step (4) is sodium borohydride; and the suitable solvent of step (4) is a mixture of isopropyl alcohol and methanol. In some embodiments, step (4) is performed at a temperature of about 0° C. to room temperature.

In some embodiments, the process further comprises (5) contacting the compound of Formula 8-I with a suitable reagent in a suitable solvent to provide the compound of Formula 9-I:

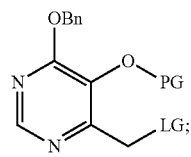

Formula 9-I wherein PG is a suitable protecting group; and

LG is a suitable leaving group.

In some embodiments, the suitable reagent of step (5) is a halogenating agent, a sulfonating agent, or a sulfonyl chloride. In some embodiments, the suitable reagent of step (5) is a halogenating agent; and LG is a halogen. In some embodiments, the suitable reagent of step (5) is $SOCl_2$, $PBr_3$, or $PCl_3$; and the suitable solvent is acetonitrile, dimethylformamide, diethyl ether, ethanol, tetrahydrofuran, isopropyl alcohol, 1,4-dioxane, toluene, water, or a combination thereof. In some embodiments, the suitable reagent of step (5) is $PBr_3$; and the suitable solvent is dimethylformamide. In some embodiments, step (5) further comprises a suitable base, selected from pyridine, N-methylmorpholine, triethylamine, diisopropylethylamine, sec-butylamine, 1,2,2,6,6-pentamethylpiperidine, tributylamine, and 1,8-diazabicyclo[5.4.0]undec-7-ene (DBU). In some embodiments, the suitable base is pyridine.

In some embodiments, R is methyl, ethyl, n-propyl, iso-propyl, n-butyl, iso-butyl, sec-butyl, t-butyl, pentyl, iso-amyl, hexyl, heptyl, octyl, or nonyl. In some embodiments, R is methyl or ethyl.

In some embodiments, —O-PG is a benzyl ether, an acetal, or a silyl ether. In some embodiments, PG is benzyl, p-methoxybenzyl, methoxymethyl, [2-(trimethylsilyl)ethoxy]methyl, triisopropylsilyl, or tert-butyldimethylsilyl. In some embodiments, PG is benzyl.

In some embodiments, R is ethyl; PG is benzyl; and X is Cl.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference for the specific purposes identified herein.

DETAILED DESCRIPTION OF THE INVENTION

Compound A refers to (S)-1-(3-(5,6-dihydroxypyrimidin-4-yl)-2-(4-((4-(morpholinomethyl)phenyl)ethynyl)phenyl)propyl)azetidine-3-carbonitrile which has the chemical structure shown below.

(Compound A)

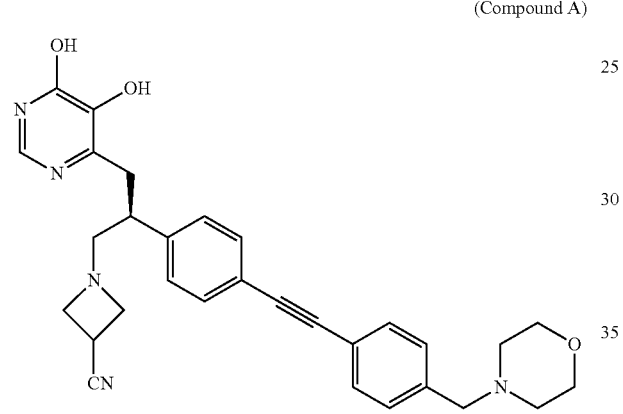

Compound A is a potent inhibitor of UDP-{3-O—[(R)-3-hydroxymyristoyl]}-N-acetylglucosamine deacetylase (LpxC). LpxC is an essential enzyme involved in the first committed step in lipid A biosynthesis for gram-negative bacteria. Lipid A is an essential component of the outer membrane of gram-negative bacteria. LpxC is highly conserved across strains of gram-negative bacteria, making LpxC an attractive target to treat gram-negative infections.

Compound A is an LpxC inhibitor that is useful in the methods of treatment described herein. In gram-negative bacterial cell lines, Compound A is a potent inhibitor, exhibiting MIC values of <1 μg/mL against *E. coli* and *K. pneumoniae* cell lines. Additionally, Compound A does not inhibit gram-positive bacterial cell lines, such as *S. aureus*.

The preparation and use of Compound A has been previously described (see, PCT/US2019/052021, which is incorporated by reference in its entirety).

Preparation of Compounds

Compounds described herein are synthesized using standard synthetic techniques or using methods known in the art in combination with methods described herein. Unless otherwise indicated, conventional methods of mass spectroscopy, NMR, HPLC are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In the reactions described, it may be necessary to protect reactive functional groups, for example hydroxy or amino groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Preparation of Compound A

Disclosed herein are novel methods for the synthesis of Compound A.

In some embodiments, Compound A is synthesized as outlined in Schemes 1-4.

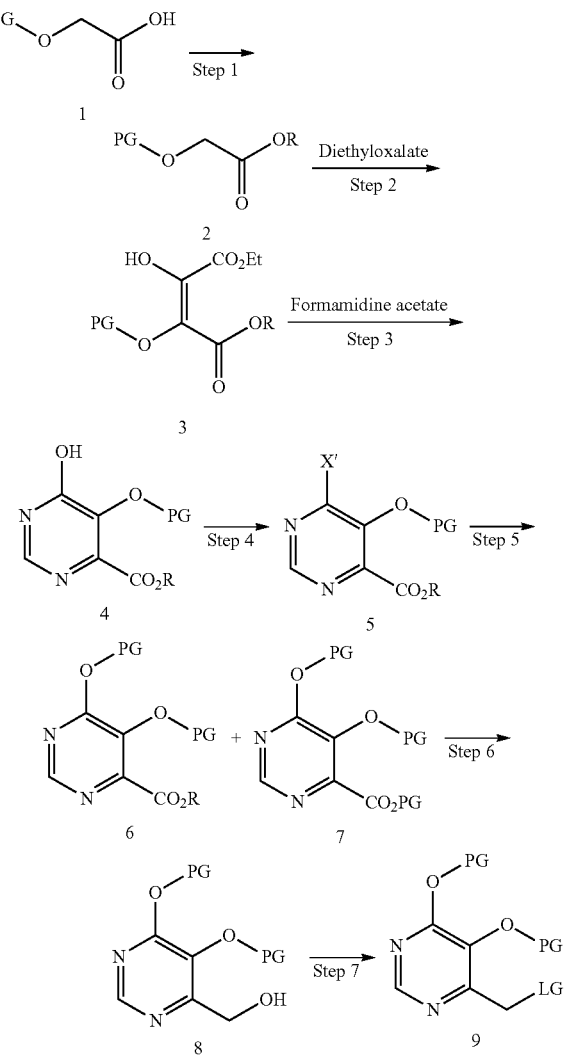

Briefly, in some embodiments, a compound of Formula 1 is esterified to yield a compound of Formula 2. In some embodiments, the compound of Formula 2 is treated with diethyl oxalate to provide a compound of Formula 3. In some embodiments, cyclization of the compound of Formula 3 with formamidine acetate provides a compound of Formula 4. In dome embodiments, halogenation of the compound of Formula 4 provides a compound of Formula 5. In some embodiments, treatment of the aryl halide with a suitable alcohol (PG-OH) yields a compound of Formula 6, or a compound of Formula 7, or a combination thereof. In other embodiments, a compound of Formula 4 is treated with a suitable reagent to yield the protected compound of Formula 6 directly. In some embodiments, the compound of Formula 6 or Formula 7, or the combination thereof, is converted to the compound of Formula 8 by reduction of the ester. Finally, in some embodiments, the alcohol of Formula 8 is converted to a leaving group to yield the compound of Formula 9.

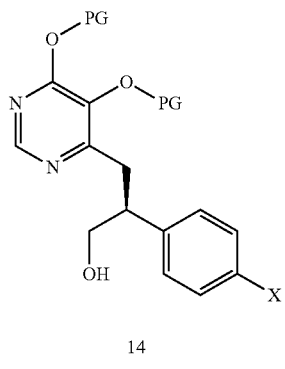

Briefly, in some embodiments, the chiral oxazolidinone of Formula 10 is treated with the acid of Formula 11 to yield the compound of Formula 12. In some embodiments, the ketone of Formula 12 is reacted with a compound of Formula 9 (vide supra) to form the compound of Formula 13. In some embodiments, the oxazolidinone is cleaved under reducing conditions to yield the primary alcohol of Formula 14.

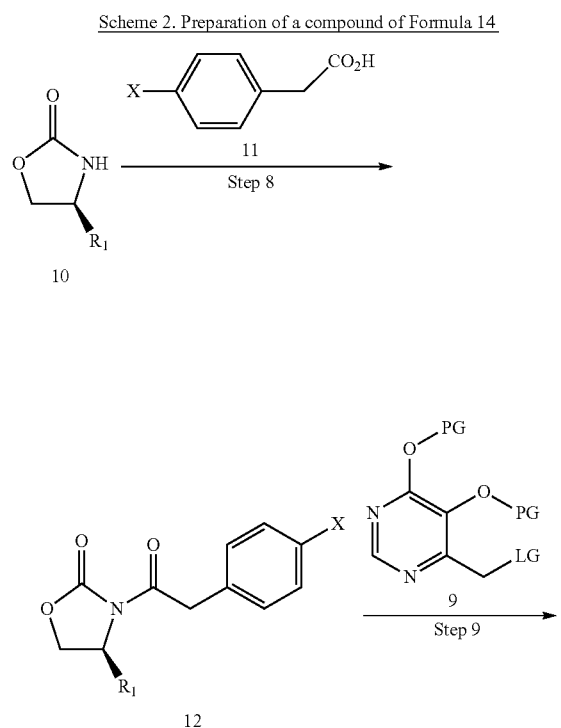

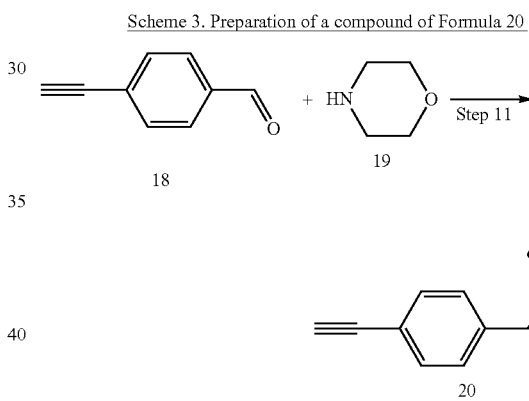

Briefly, in some embodiments, the compound of Formula 18, is reacted with a compound of Formula 19, or a salt thereof, under reductive amination conditions to yield the compound of Formula 20, or a salt thereof.

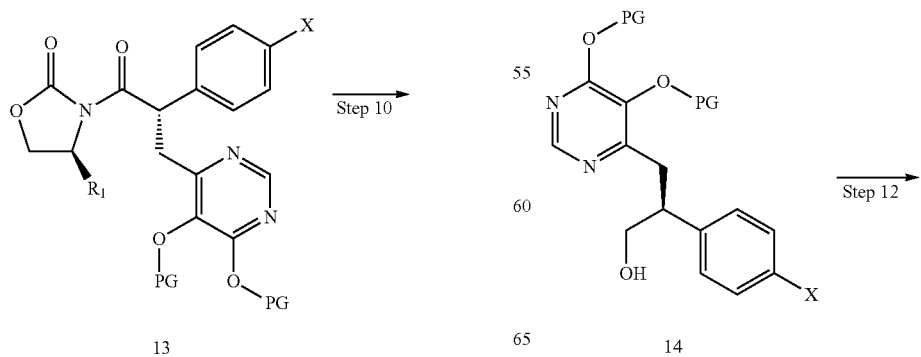

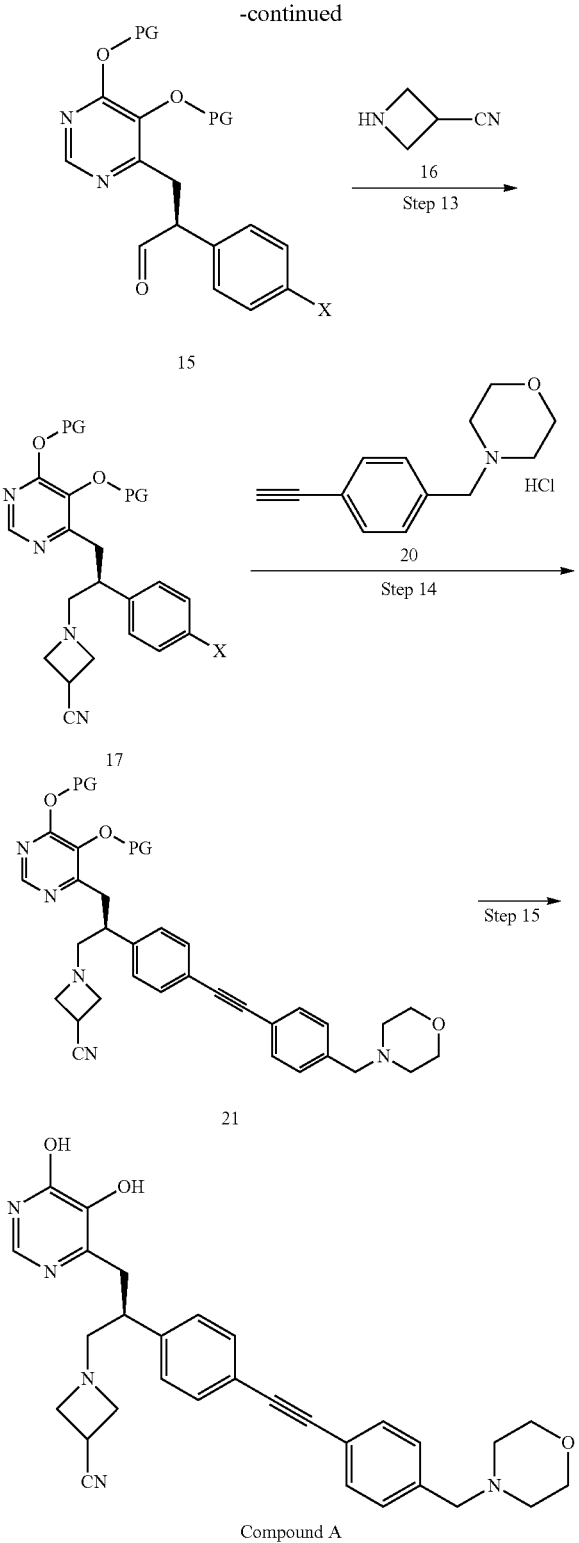

of Formula 20 (vide supra) under cross-coupling conditions to yield the compound of Formula 21. Finally, in some embodiments, the protected compound of Formula 21 is treated with appropriate deprotection conditions to yield Compound A.

As disclosed herein, variables in Schemes 1-4 are defined as follows: each PG is a suitable protecting group; R is $C_1$-$C_{10}$ alkyl; X' is Cl or Br; LG is a suitable leaving group; $R_1$ is $C_1$-$C_{10}$ alkyl, aryl, or benzyl; and X is halogen, —OTf, —OTs, or —OMs.

In some embodiments, each PG is the same suitable protecting group. In some embodiments, each PG is a different suitable protecting group. In some embodiments, each —O-PG is an ether, a benzyl ether, an acetal, or a silyl ether; wherein each PG is the same protecting group. In some embodiments, each —O-PG is a benzyl ether, an acetal, or a silyl ether, wherein each PG is the same protecting group. In some embodiments, each PG is methyl, benzyl, p-methoxybenzyl, methoxymethyl, [2-(trimethylsilyl)ethoxy]methyl, triisopropylsilyl, or tert-butyldimethylsilyl. In some embodiments, each PG is benzyl.

In some embodiments, R is methyl, ethyl, n-propyl, iso-propyl, n-butyl, iso-butyl, sec-butyl, t-butyl, pentyl, iso-amyl, hexyl, heptyl, octyl, or nonyl. In some embodiments, R is methyl, ethyl, or isopropyl. In some embodiments, R is methyl or ethyl. In some embodiments, R is ethyl.

In some embodiments, X is Cl. In other embodiments, X is Br.

In some embodiments, LG is a halogen, a sulfonate, or a sulfate. In some embodiments, LG is Cl, Br, I, mesylate, tosylate, or triflate. In some embodiments, LG is Cl, Br, I, —OTf, —OTs, or —OMs. In some embodiments, is a halogen. In some embodiments, LG is Cl, Br, or I. In some embodiments, LG is Br or I. In some embodiments, LG is Br.

In some embodiments, $R_1$ is $C_1$-$C_6$ alkyl, phenyl, naphthyl, or benzyl. In some embodiments, $R_1$ is methyl, isopropyl, tert-butyl, phenyl, or benzyl. In some embodiments, $R_1$ is isopropyl, phenyl, or benzyl. In some embodiments, $R_1$ is benzyl.

In some embodiments, X is halogen. In some embodiments, X is Cl, Br, or I. In some embodiments, X is Br or I. In some embodiments, X is Br. In some embodiments, X is I. In some embodiments, X is —OTf, —OTs, or —OMs.

Step 1: Synthesis of a Compound of Formula 2

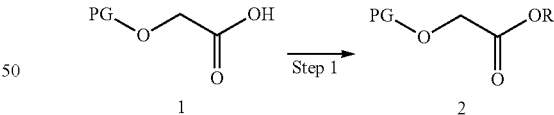

In some embodiments, a compound of Formula 1 is esterified to a compound of Formula 2. In some embodiments, the esterification proceeds in a suitable alcohol solvent in the presence of a suitable acid. In some embodiments, the suitable solvent has the formula R—OH, wherein R is $C_1$-$C_{10}$ alkyl. In some embodiments, the suitable solvent is methanol, ethanol, or isopropanol. In some embodiments, the suitable solvent is ethanol, and R is ethyl. In some embodiments, the suitable acid is an inorganic acid. In some embodiments, the suitable acid is HCl, HBr, HNO$_3$, or H$_2$SO$_4$, or the like. In some embodiments, the suitable acid is H$_2$SO$_4$. In some embodiments, the reaction is performed at an elevated temperature. In some embodiments, the reaction is performed at the reflux temperature of the reac- Briefly, in some embodiments, the primary alcohol compound of Formula 14 is oxidized to the aldehyde containing compound of Formula 15. In some embodiments, the compound of Formula 15 is reacted with a compound of Formula 16, or a salt thereof, under reductive amination conditions to yield the compound of Formula 17. In some embodiments, the compound of Formula 17 is reacted with the compound tion mixture. In some embodiments, the reaction is performed at the boiling point of the solvent used. In some embodiments, the solvent is ethanol, and the reaction is performed at about 78-80° C.

In some embodiments, the compound of Formula 1 is Compound 1A:

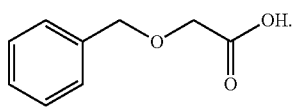
(Compound 1A)

In some embodiments, the compound of Formula 2 is Compound 2A:

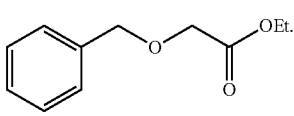
(Compound 2A)

Step 2: Synthesis of a Compound of Formula 3

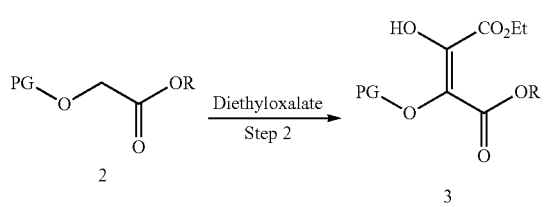

In some embodiments, a compound of Formula 2 is treated with diethyl oxalate in the presence of a suitable base and in a suitable solvent to yield the compound of Formula 3. In some embodiments, the suitable base is sodium hydride, sodium methoxide, sodium ethoxide, lithium aluminum hydride, n-butyllithium, or the like. In some embodiments, the suitable base is sodium hydride. In some embodiments, the sodium hydride is provided as a 60% suspension in mineral oil. In some embodiments, the suitable solvent is methanol, ethanol, dimethoxyethane, 2-methyltetrahydrofuran, methyl tert-butyl ether, cyclopentyl methyl ether, tetrahydrofuran, diethyl ether, diisopropyl ether, 1,4-dioxane, or a combination thereof. In some embodiments, the suitable solvent is dimethoxyethane, 2-methyltetrahydrofuran, methyl tert-butyl ether, cyclopentyl methyl ether, tetrahydrofuran, diethyl ether, diisopropyl ether, 1,4-dioxane, or a combination thereof. In some embodiments, the suitable solvent is tetrahydrofuran. In some embodiments, the reaction is performed at a low temperature. In some embodiments, the reaction is performed at about 0° C. In some embodiments, the reaction mixture is allowed to warm to room temperature (about 25° C.).

In some embodiments, the compound of Formula 3 is Compound 3A:

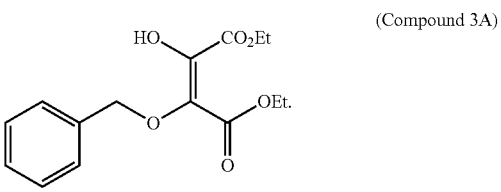 [SMILES: CCOC(=O)/C(O)=C(/OCc1ccccc1)C(=O)OCC]
(Compound 3A)

In some embodiments, the compound of Formula 3 is not isolated, and is taken onto Step 3 directly. In some embodiments, after warming to room temperature and the reaction of Step 2 is complete, the reaction mixture is cooled again and taken on to Step 3 directly.

Step 3: Synthesis of a Compound of Formula 4

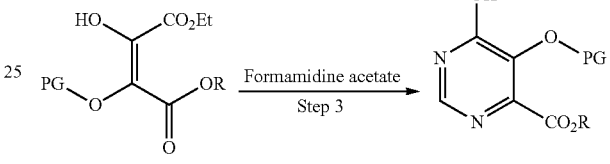

In some embodiments, cyclization of the compound of Formula 3 with formamidine acetate in the presence of a suitable base and in a suitable solvent provides a compound of Formula 4. In some embodiments, the suitable base is sodium hydride, sodium methoxide, sodium ethoxide, lithium methoxide, lithium ethoxide, n-butyl lithium, lithium diisopropylamide (LDA), lithium bis(trimethylsilyl) amide (LiHMDS), or lithium tetramethylpiperidide (LiTMP), or the like. In some embodiments, the suitable base is sodium methoxide, sodium ethoxide, lithium methoxide, lithium ethoxide, or the like. In some embodiments, the suitable base is sodium ethoxide. In some embodiments, the suitable solvent is methanol, ethanol, isopropyl alcohol, diethyl ether, diisopropyl ether, tetrahydrofuran, 2-methyltetrahydrofuran, 1,4-dioxane, tert-butyl methyl ether, cyclopropyl methyl ether, or a combination thereof. In some embodiments, the suitable solvent is methanol or ethanol. In some embodiments, the suitable solvent is ethanol. In some embodiments, the reaction is performed at a low temperature. In some embodiments, the reaction is performed at 0° C. In some embodiments, the reaction is performed at a temperature of about 0-10° C.

In some embodiments, when the compound of Formula 3 is not isolated from Step 2 the suitable solvent is a mixture of methanol or ethanol and tetrahydrofuran. In some embodiments, the suitable solvent is a mixture of ethanol and tetrahydrofuran. In some embodiments, the suitable base is sodium ethoxide and the suitable solvent is a mixture of ethanol and tetrahydrofuran. In some embodiments, the reaction mixture from Step 2 is cooled to a temperature of about 0-10° C. and the reaction of Step 3 is performed.

In some embodiments, the compound of Formula 4 is Compound 4A:

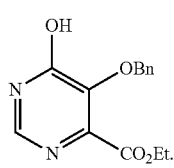

(Compound 4A)

In some embodiments, the compound of Formula 5 is Compound 5A:

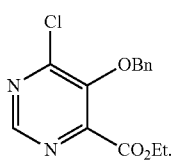

(Compound 5A)

Step 4: Synthesis of a Compound of Formula 5

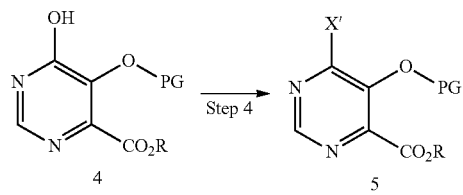

In some embodiments, the hydroxyl group of the compound of Formula 4 is converted to a halogen atom (X' is Br or Cl), providing the compound of Formula 5, by a halogenating agent and a suitable base in a suitable solvent. In some embodiments, halogenation is bromination. In some embodiments, halogenation is chlorination. In some embodiments, the halogenating agent is phosphorus oxychloride ($POCl_3$), thionyl chloride ($SOCl_2$), phosphorus tribromide ($PBr_3$), phosphorus oxybromide ($POBr_3$), hydrobromic acid, bromine, dibromotriphenylphosphorane, or the like. In some embodiments, halogenation is chlorination and the halogenating agent is phosphorus oxychloride ($POCl_3$) or thionyl chloride ($SOCl_2$). In some embodiments, halogenation is bromination and the halogenating agent is phosphorus tribromide ($PBr_3$), phosphorus oxybromide ($POBr_3$), hydrobromic acid, bromine, or dibromotriphenylphosphorane. In some embodiments, the halogenating agent is $POCl_3$, $POBr_3$, or $SOCl_2$. In some embodiments, the halogenating agent is $POCl_3$. In some embodiments, the suitable base is triethylamine, diisopropylethylamine, sec-butylamine, 1,2,2,6,6-pentamethylpiperidine, tributylamine, or 1,8-diazabicyclo[5.4.0]undec-7-ene (DBU), or the like. In some embodiments, the suitable base is triethylamine. In some embodiments, the suitable solvent is acetonitrile, water, ethanol, isopropanol, dichloromethane, chloroform, dichloroethane, toluene, N,N-dimethylformamide, acetic acid, acetone, or the like. In some embodiments, the suitable solvent is acetonitrile, dichloromethane, chloroform, dichloroethane, toluene, or a combination thereof. In some embodiments, the suitable solvent is toluene. In some embodiments, the reaction is performed at an elevated temperature. In some embodiments, the reaction is performed at the reflux temperature of the reaction mixture. In some embodiments, the reaction is performed at about 85-95° C.

Step 5: Synthesis of a Compound of Formula 6, Formula 7, or a Combination Thereof

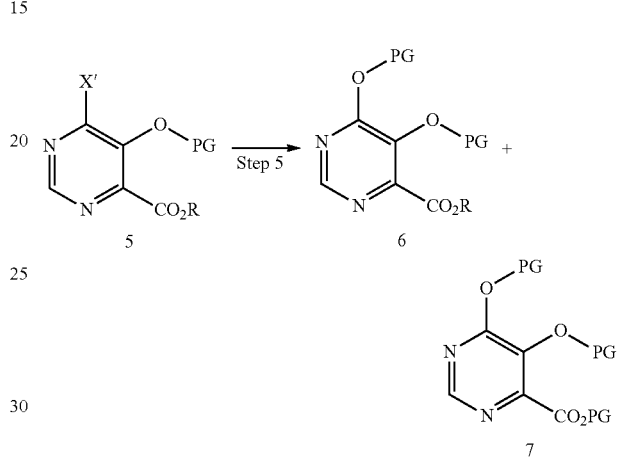

In some embodiments, treatment of the aryl halide of Formula 5 with a suitable alcohol (PG-OH) yields a compound of Formula 6, or a compound of Formula 7, or a combination thereof. In some embodiment, the reaction yields a compound of Formula 6. In other embodiments, the reaction yields a compound of Formula 7. In other embodiments, the reaction yields a combination of a compound of Formula 6 and a compound of Formula 7. In such embodiments, —O-PG is an ether or a benzyl ether.

In some embodiments, the suitable alcohol (R—OH) is methanol, ethanol, or benzyl alcohol. In some embodiments, the suitable alcohol (R—OH) is benzyl alcohol. In some such embodiments, the compound of Formula 6 is a compound of Formula 6-I, and the compound of Formula 7 is a compound of Formula 7-I:

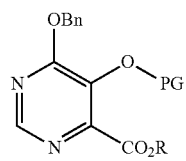

Formula 6-I

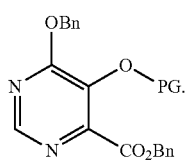

Formula 7-I

In some embodiments, the reaction comprises a suitable base and is run in a suitable solvent. In some embodiments, the suitable base is triethylamine, diisopropylethylamine, sec-butylamine, 1,2,2,6,6-pentamethylpiperidine, tributylamine, or 1,8-diazabicyclo[5.4.0]undec-7-ene (DBU), or the like. In some embodiments, the suitable base is triethylamine, diisopropylethylamine, 1,2,2,6,6-pentamethylpiperidine, tributylamine, or 1,8-diazabicyclo[5.4.0] undec-7-ene (DBU). In some embodiments, the suitable base is DBU. In some embodiments, the suitable solvent is acetonitrile, dimethylformamide, diethyl ether, ethanol, tetrahydrofuran, isopropyl alcohol, 1,4-dioxane, toluene, water, or a combination thereof. In some embodiments, the suitable solvent is acetonitrile. In other embodiments, the suitable solvent is the suitable alcohol having formula R—OH. In some such embodiments, the suitable solvent is methanol, ethanol, or benzyl alcohol.

In some embodiments, the compound of Formula 6 or Formula 6-I is Compound 6A:

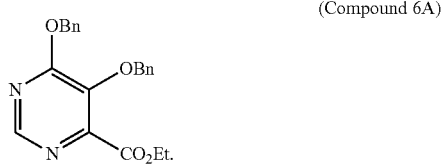 [SMILES: CCOC(=O)c1ncnc(OCc2ccccc2)c1OCc1ccccc1]

(Compound 6A)

In some embodiments, the compound of Formula 7 or Formula 7-I is Compound 7A:

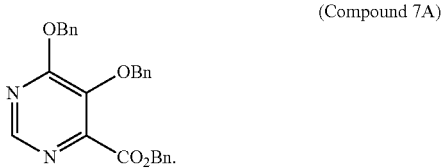 [SMILES: O=C(OCc1ccccc1)c1ncnc(OCc2ccccc2)c1OCc1ccccc1]

(Compound 7A)

Step Alt-5: Alternative Synthesis of a Compound of Formula 6:

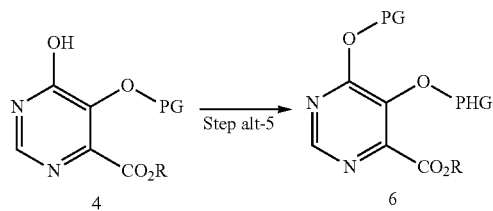

In other embodiments, a compound of Formula 4 is treated with a suitable reagent in a suitable solvent to yield the protected compound of Formula 6 directly.

In some such embodiments, the suitable reagent is a benzyl halide, such as a benzyl bromide. In such embodiments, —O-PG is a benzyl ether. In some such embodiments, the suitable reagent is benzyl bromide, p-methoxybenzyl bromide, or the like. In such embodiments, PG is benzyl, p-methoxybenzyl, respectively, or the like. In some embodiments, the suitable solvent is acetonitrile, dichloromethane, dimethylformamide, acetone, diethyl ether, ethanol, tetrahydrofuran, isopropyl alcohol, 1,4-dioxane, toluene, water, or a combination thereof.

In other such embodiments, the suitable reagent is a silyl chloride. In such embodiments, —O-PG is a silyl ether. In some such embodiments, the suitable reagent is triisopropylsilyl chloride or tert-butyldimethylsilyl chloride, or the like. In such embodiments, PG is triisopropylsilyl or tert-butyldimethylsilyl, respectively, or the like. In some embodiments, the suitable base is imidazole. In some embodiments, the suitable solvent is acetonitrile, dichloromethane, dimethylformamide, diethyl ether, ethanol, tetrahydrofuran, isopropyl alcohol, 1,4-dioxane, toluene, water, or a combination thereof.

In other such embodiments, the suitable reagent is a chloromethyl ether. In such embodiments, —O-PG is an acetal. In some such embodiments, the suitable reagent is [2-(trimethylsilyl)ethoxy]methyl chloride or chloromethyl methyl ether, or the like. In such embodiments, PG is [2-(trimethylsilyl)ethoxy]methyl or methoxymethyl, respectively, or the like. In some embodiments, the suitable base is triethylamine, diisopropylethylamine, 1,2,2,6,6-pentamethylpiperidine, tributylamine, or 1,8-diazabicyclo[5.4.0]undec-7-ene (DBU), or the like. In some embodiments, the suitable solvent is acetonitrile, dichloromethane, dimethylformamide, diethyl ether, ethanol, tetrahydrofuran, isopropyl alcohol, 1,4-dioxane, toluene, water, or a combination thereof.

Step 6: Synthesis of a Compound of Formula 8

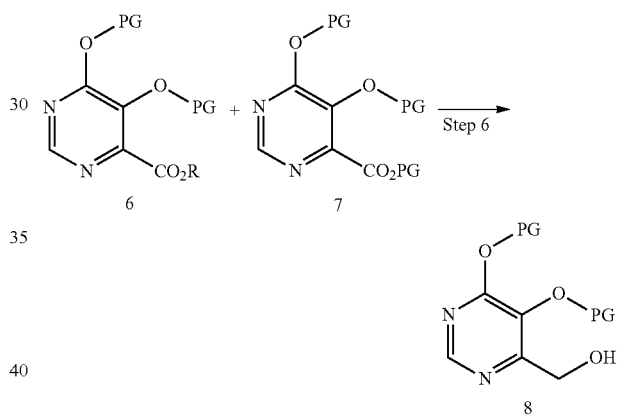

In some embodiments, the compound of Formula 6 or Formula 7, or the combination thereof, is converted to the compound of Formula 8 by reduction of the ester with suitable reducing agent in a suitable solvent. In some embodiments, the suitable reducing agent is a borohydride. In some embodiments, the suitable reducing agent is sodium borohydride, sodium cyanoborohydride, sodium triacetoxyborohydride, or lithium cyanoborohydride, or the like. In some embodiments, the suitable reducing agent is sodium borohydride. In some embodiments, the suitable solvent is acetonitrile, dimethylformamide, diethyl ether, methanol, ethanol, tetrahydrofuran, isopropyl alcohol, 1,4-dioxane, toluene, water, or a combination thereof. In some embodiments, the suitable solvent is methanol, ethanol, isopropyl alcohol, water, or a combination thereof. In some embodiments, the suitable solvent is a mixture of isopropyl alcohol and methanol. In some embodiments, the reaction is performed at a low temperature. In some embodiments, the reaction is performed at about 0° C. In some embodiments, the reaction mixture is allowed to warm to room temperature (about 25° C.).

In embodiments where the compound of Formula 6 or Formula 7 is a compound of Formula 6-I or 7-I, the compound of Formula 8 is a compound of Formula 8-I:

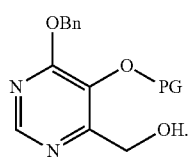

Formula 8-I

In some embodiments, the compound of Formula 8 or Formula 8-I is Compound 8A:

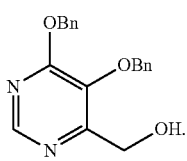

(Compound 8A)

Step 7: Synthesis of a Compound of Formula 9

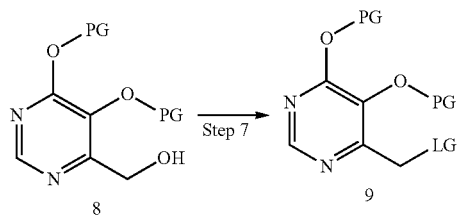

In some embodiments, the alcohol —OH group of Formula 8 is converted to a leaving group to yield the compound of Formula 9, by treatment with a suitable reagent in a suitable solvent. In some embodiments, the suitable reagent is a halogenating agent, a sulfonating agent, or a sulfonyl chloride. In some embodiments, the suitable reagent is a halogenating agent. In such embodiments, LG is a halogen. In some embodiments, LG is Cl, Br, or I. In some embodiments, LG is Br or I. In some embodiments, LG is Cl or Br. In some embodiments, LG is Br. In some embodiments, the suitable reagent is $SOCl_2$, $PBr_3$, or $PCl_3$, or the like. In some embodiments, the suitable reagent is $PBr_3$. In some embodiments, the suitable reagent is a sulfonating agent. In such embodiments, LG is a sulfate. In some embodiments, the suitable reagent is a sulfonyl chloride. In such embodiments, LG is a sulfonate. In some embodiments, the suitable reagent is tosyl chloride, mesyl chloride, or triflyl chloride, or the like. In such embodiments, LG is a tosylate, mesylate, or triflate, respectively, or the like. In some embodiments, the suitable solvent is acetonitrile, dimethylformamide, diethyl ether, ethanol, tetrahydrofuran, isopropyl alcohol, 1,4-dioxane, toluene, water, or a combination thereof. In some embodiments, the suitable solvent is dimethylformamide. In some embodiments, the reaction is performed at about 0° C.

In some embodiments, Step 7 further comprises a suitable base. In some embodiments, the suitable base is pyridine, N-methylmorpholine, triethylamine, diisopropylethylamine, sec-butylamine, 1,2,2,6,6-pentamethylpiperidine, tributylamine, and 1,8-diazabicyclo[5.4.0]undec-7-ene (DBU), or the like. In some embodiments, the suitable base is pyridine.

In embodiments where the compound of Formula 8 is a compound of Formula 8-I, the compound of Formula 9 is a compound of Formula 9-I:

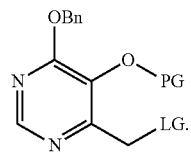

Formula 9-I

In some embodiments, the compound of Formula 9 or Formula 9-I is Compound 9A:

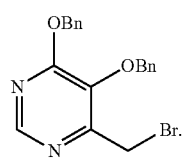

(Compound 9A)

Step 8: Synthesis of a Compound of Formula 12

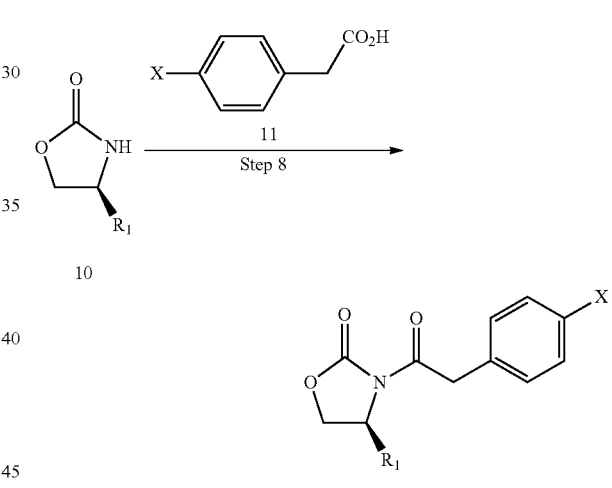

In some embodiments, using standard oxazolidinone chiral auxiliary chemistry, the chiral oxazolidinone of Formula 10 is treated with the acid of Formula 11 to yield the amide of Formula 12. In some embodiments, the amide formation proceeds with a suitable reagent, a suitable base, and in a suitable solvent. In some embodiments, the suitable reagent is BOP, PyBOP, HATU, HBTU, pivaloyl chloride, or the like. In some embodiments, the suitable reagent is pivaloyl chloride. In some embodiments, the use of pivaloyl chloride is more cost-effective than other expensive amide coupling reagents. In some embodiments, the suitable base is N-methylmorpholine, triethylamine, diisopropylethylamine, sec-butylamine, 1,2,2,6,6-pentamethylpiperidine, tributylamine, and 1,8-diazabicyclo[5.4.0]undec-7-ene (DBU), or the like. In some embodiments, the suitable base is N-methylmorpholine. In some embodiments, the suitable solvent is acetonitrile, dimethylformamide, diethyl ether, ethanol, tetrahydrofuran, isopropyl alcohol, 1,4-dioxane, toluene, or a combination thereof. In some embodiments, the suitable solvent is toluene. In some embodiments, the reaction is performed at elevated temperature. In some embodiments, the reaction is performed at the reflux temperature of the reaction mixture. In some embodiments, the reaction is performed at the boiling point of the solvent used. In some embodiments, the solvent is toluene, and the reaction is performed at about 107-112° C.

In some embodiments, the compound of Formula 10 is Compound 10A:

(Compound 10A)

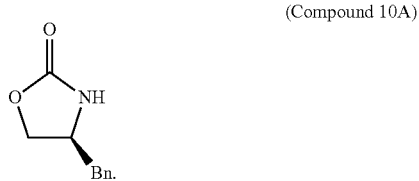 [SMILES: O=C1N[C@@H](Cc2ccccc2)CO1]

In some embodiments, the compound of Formula 11 is Compound 11A:

(Compound 11A)

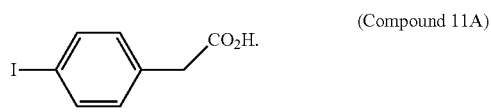 [SMILES: O=C(O)Cc1ccc(I)cc1]

In some embodiments, the compound of Formula 12 is Compound 12A:

(Compound 12A)

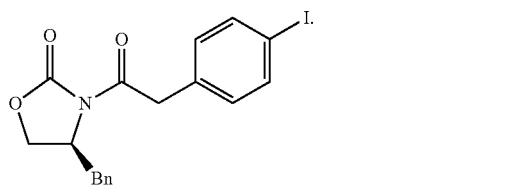

Step 9: Synthesis of a Compound of Formula 13

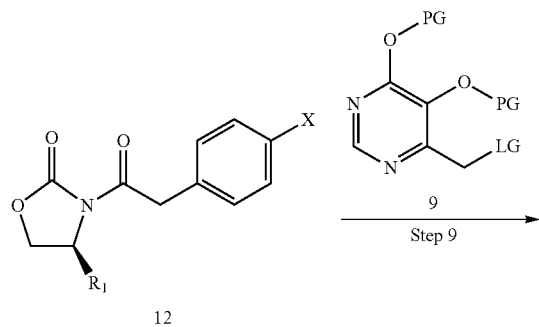

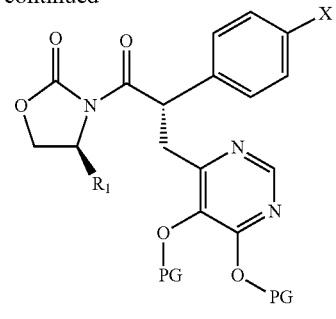

In some embodiments, using standard oxazolidinone chiral auxiliary chemistry, the chiral oxazolidinone amide of Formula 12 is reacted with a suitable base and the compound of Formula 9 (vide supra) in a suitable solvent to provide the compound of Formula 13. In some embodiments, the suitable base is n-butyl lithium, lithium diisopropylamide (LDA), lithium bis(trimethylsilyl)amide (LiHMDS), or lithium tetramethylpiperidide (LiTMP), or the like. In some embodiments, the suitable base is LiHMDS. In some embodiments, the suitable solvent is diethyl ether, diisopropyl ether, tetrahydrofuran, 2-methyltetrahydrofuran, 1,4-dioxane, tert-butyl methyl ether, cyclopropyl methyl ether, or a combination thereof. In some embodiments, the suitable solvent is tetrahydrofuran. In some embodiments, the reaction is performed at a temperature below 0° C. In some embodiments, the reaction is performed at a temperature of about −25 to about −15° C.

In some embodiments, the compound of Formula 12 is reacted with the suitable base before addition of the compound of Formula 9. In some embodiments, the compound of Formula 12 is reacted with the base for from about 15 min to about 60 min before the addition of the compound of Formula 9. In some embodiments, the compound of Formula 12 is reacted with the base for from about 15 min before the addition of the compound of Formula 9.

In some embodiments, the compound of Formula 13 is Compound 13A:

(Compound 13A)

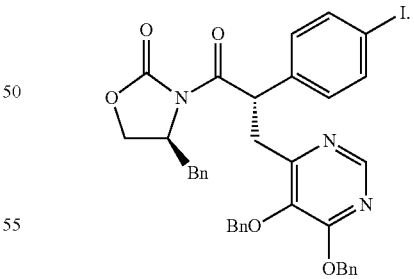

In some embodiments, the process of Steps 8 and 9 produces a single diastereomer of a compound of Formula 13 (such as Compound 13A). In some embodiments, the process produces >95% of a single diastereomer of a compound of Formula 13 (such as Compound 13A). In some embodiments, isolation of the compound of Formula 13 (such as Compound 13A) comprises a crystallization step. In some embodiments, the process of Steps 8 and 9 produces >95%, >96%, >97%, >98%, or >99% of a single diastereomer of a compound of Formula 13 (such as Compound 13A). In some embodiments, the compound of Formula 13 (such as Compound 13A) is isolated with 99% de, 99.1% de, 99.2% de, 99.3% de, 99.4% de, 99.5% de, or >99.5% de.

Step 10: Synthesis of a Compound of Formula 14

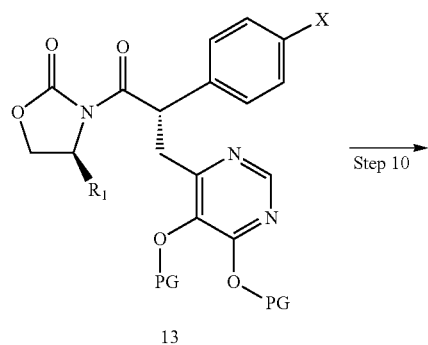

In some embodiments, the oxazolidinone is cleaved under reducing conditions to yield the primary alcohol of Formula 14. In some embodiments, the compound of Formula 13 is treated with a suitable borohydride reagent in a suitable solvent to provide the compound of Formula 14. In some embodiments, the suitable borohydride reagent is lithium borohydride, sodium borohydride, sodium cyanoborohydride, potassium borohydride, lithium triethylborohydride, or sodium triacetoxyborohydride, or the like. In some embodiments, the suitable borohydride reagent is lithium borohydride. In some embodiments, the suitable solvent is acetonitrile, methanol, ethanol, isopropyl alcohol, dimethoxyethane, 2-methyltetrahydrofuran, methyl tert-butyl ether, cyclopentyl methyl ether, tetrahydrofuran, diethyl ether, diisopropyl ether, 1,4-dioxane, toluene, water, or a combination thereof. In some embodiments, the suitable solvent is methanol, ethanol, isopropyl alcohol, tetrahydrofuran, 1,4-dioxane, or a combination thereof. In some embodiments, the suitable solvent is a mixture of tetrahydrofuran and ethanol. In some embodiments, the reaction is performed at a low temperature. In some embodiments, the reaction is performed at about 0° C. In some embodiments, the reaction mixture is allowed to warm to room temperature (about 25° C.).

In some embodiments, the compound of Formula 14 is Compound 14A:

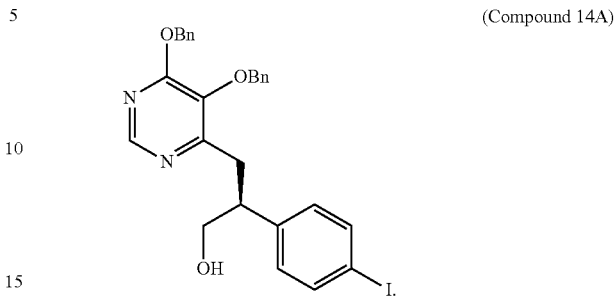

Step 10-A: Crystallization of a Compound of Formula 14

In some embodiments, the compound of Formula 14 (such as Compound 14A) is recrystallized. In some embodiments, the compound of Formula 14 (such as Compound 14A) is recrystallized from acetonitrile, methanol, ethanol, isopropyl alcohol, acetone, methyl acetate, ethyl acetate, dichloromethane, chloroform, diethyl ether, diisopropyl ether, tert-butyl methyl ether, tetrahydrofuran, 2-methyltetrahydrofuran, dioxane, benzene, toluene, petroleum ether, pentane, hexane, heptane, cyclohexane, acetic acid, water, or a mixture thereof. In some embodiments, the compound of Formula 14 (such as Compound 14A) is recrystallized from methanol, ethanol, isopropyl alcohol, or water, or a mixture thereof. In some embodiments, the compound of Formula 14 (such as Compound 14A) is recrystallized from a mixture of isopropyl alcohol and water. In some embodiments, the compound of Formula 14 (such as Compound 14A) is recrystallized from a mixture of isopropanol and water in a ratio of about 5:1, about 4:1, about 3:1, about 2:1, about 1:1, or about 1:2 isopropyl alcohol to water.

In some embodiments, the process of Steps 8-10 produces a single enantiomer of a compound of Formula 14 (such as Compound 14A). In some embodiments, the process produces >95% of a single enantiomer of a compound of Formula 14 (such as Compound 14A). In some embodiments, the process of Steps 8-10 produces >95%, >96%, >97%, >98%, or >99% of a single enantiomer of a compound of Formula 14 (such as Compound 14A). In some embodiments, the compound of Formula 14 (such as Compound 14A) is isolated with 99% ee, 99.1% ee, 99.2% ee, 99.3% ee, 99.4% ee, 99.5% ee, 99.6% ee, 99.7% ee, 99.8% ee, 99.9% ee, or >99.9% ee.

Step 11: Synthesis of a Compound of Formula 20, or a Salt Thereof

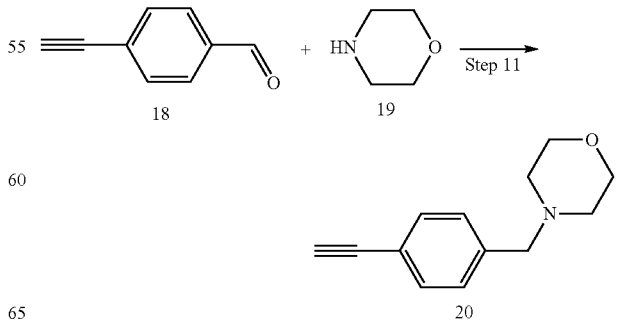

In some embodiments, the aldehyde of Formula 18 and morpholine (the compound of Formula 19), or a salt thereof, are treated with a suitable borohydride reagent in a suitable solvent to yield the compound of Formula 20, or a salt thereof. In some embodiments, the suitable borohydride reagent is lithium borohydride, sodium borohydride, sodium cyanoborohydride, potassium borohydride, lithium triethylborohydride, or sodium triacetoxyborohydride, or the like. In some embodiments, the suitable borohydride reagent is sodium triacetoxyborohydride. In some embodiments, the suitable solvent is acetonitrile, methanol, ethanol, isopropyl alcohol, dimethoxyethane, 2-methyltetrahydrofuran, methyl tert-butyl ether, cyclopentyl methyl ether, tetrahydrofuran, diethyl ether, diisopropyl ether, 1,4-dioxane, toluene, water, or a combination thereof. In some embodiments, the suitable solvent is methanol, ethanol, isopropyl alcohol, tetrahydrofuran, 1,4-dioxane, or a combination thereof. In some embodiments, the suitable solvent is tetrahydrofuran. In some embodiments, the reaction is performed at a low temperature. In some embodiments, the reaction is performed at about 0° C. In some embodiments, the reaction mixture is allowed to warm to room temperature (about 25° C.).

In some embodiments, the compound of Formula 20 is isolated as a salt. In some embodiments, the compound of Formula 20 is isolated the HCl addition salt. In some embodiments, the compound of Formula 20, or salt thereof, is Compound 20A:

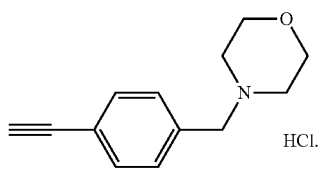

(Compound 20A)

Step 12: Synthesis of a Compound of Formula 15

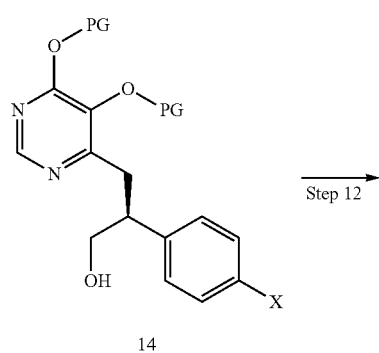

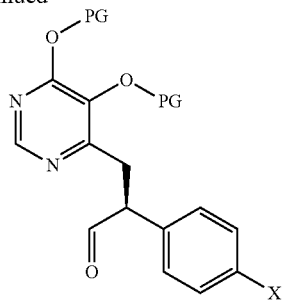

In some embodiments, the primary alcohol compound of Formula 14 is treated with a suitable oxidation reagent system in a suitable solvent to provide the aldehyde compound of Formula 15. In some embodiments, the suitable oxidation reagent system is a chromium based reagent (such as Collins reagent, pyridinium dichromate, or pyridinium chlorochromate), a sulfonium species, a hypervalent iodine reagent (such as Dess-Martin periodinane or 2-iodobenzoic acid), a TPAP/NMO system, or a TEMPO/bleach system. In some embodiments, the suitable solvent is acetonitrile, dimethylsulfoxide, dichloromethane, chloroform, dichloroethane, hexanes, ethyl acetate, acetic acid, toluene, water, or a combination thereof.

In preferred embodiments, the suitable oxidation reagent system is a TEMPO/bleach system. In some embodiments, the reaction mixture comprises substoichiometric or a catalytic amount of TEMPO. In some embodiments, the reaction mixture comprises about 0.0025, 0.005, 0.0075, 0.01, 0.015, 0.02, 0.025, 0.03, 0.05, 0.075, or 0.10 equivalents of TEMPO. In some embodiments, the reaction mixture comprises about 1.0, 1.1, 1.2, 1.3, 1.4, 1.5, 1.75, or 2.0 equivalents of bleach. In some embodiments, the pH of the bleach solution is adjusted. In some embodiments, the pH is adjusted to about 9.0, 9.1, 9.2, 9.3, 9.4, or 9.5. In some embodiments, the pH is adjusted with NaHCO₃. In some embodiments, the reaction mixture further comprises a suitable salt. In some embodiments, the suitable salt is KBr. In some embodiments, the suitable solvent is acetonitrile, dichloromethane, chloroform, dichloroethane, hexanes, water, or a combination thereof. In some embodiments, the suitable solvent is a mixture of water and dichloromethane. In some embodiments, the reaction is performed at about 0° C. In some embodiments, the reaction mixture is performed at about 0-5° C. In some embodiments, the reaction is kept below 5° C.

In some embodiments, the compound of Formula 15, or salt thereof, is Compound 15A:

(Compound 15A)

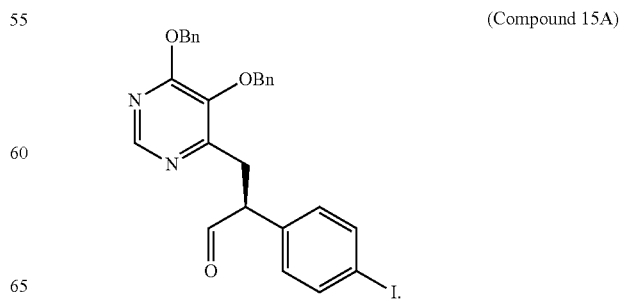

In some embodiments, using a TEMPO/bleach oxidation system does not degrade the stereochemistry of the compound. In some embodiments, using a TEMPO/bleach oxidation system does not significantly degrade the stereochemistry of the compound. In some embodiments, the ee of the compound of Formula 15 (such as Compound 15A) is the same as the ee of the compound of Formula 14 (such as 14A). In some embodiments, the ee of the compound of Formula 15 (such as Compound 15A) is substantially the same as the ee of the compound of Formula 14 (such as 14A). In some embodiments, the ee of the compound of Formula 15 (such as Compound 15A) is 0.2 or 0.1 of the ee of the compound of Formula 14 (such as 14A).

In some embodiments, the compound of Formula 15 is not isolated, and is taken onto Step 13 directly. In some embodiments, after workup of the reaction of Step 12, the compound of Formula 15 is not isolated, and is taken on to Step 13 directly. In some embodiments, the water later is removed from the reaction mixture of Step 12, and the organic layer is taken onto Step 13 directly without isolation of the compound of Formula 15 (such as Compound 15A).

Step 13: Synthesis of a Compound of Formula 17

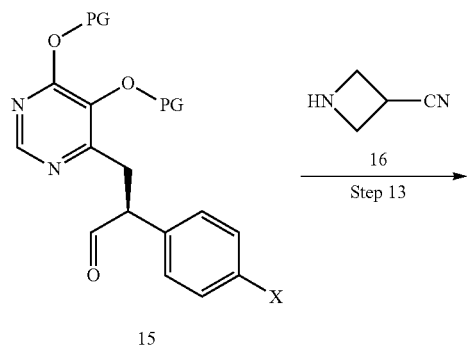

the compound of Formula 17, or a salt thereof. In some embodiments, the suitable reducing agent is sodium borohydride, sodium cyanoborohydride, sodium triacetoxyborohydride, lithium cyanoborohydride, H$_2$/catalyst, or picoline-borane. In some embodiments, the suitable reducing agent is sodium borohydride, sodium cyanoborohydride, sodium triacetoxyborohydride, lithium cyanoborohydride, or picoline-borane. In some embodiments, the suitable reducing agent is a borohydride reagent or picoline-borane. In some embodiments, the suitable reducing agent is picoline-borane. In some embodiments, the suitable solvent is acetonitrile, methanol, ethanol, dichloromethane, chloroform, dichloroethane, toluene, water, or a combination thereof. In some embodiments, the suitable solvent is a mixture of methanol and dichloromethane. In some embodiments, the reaction is performed at about 0° C. In some embodiments, the reaction mixture is allowed to warm to room temperature (about 25° C.).

In some embodiments, when the compound of Formula 15 is not isolated from Step 12, the suitable solvent is a mixture of dichloromethane and methanol. In some embodiments, the reaction mixture from Step 2 is maintained at a temperature of about 0-5° C. and the reaction of Step 13 is performed. In some embodiments, the reaction is performed at about 0° C. In some embodiments, the reaction mixture is allowed to warm to room temperature (about 25° C.).

In some embodiments, the compound of Formula 16 is used as a salt. In some embodiments, the compound of Formula 16, or salt thereof, is Compound 16A:

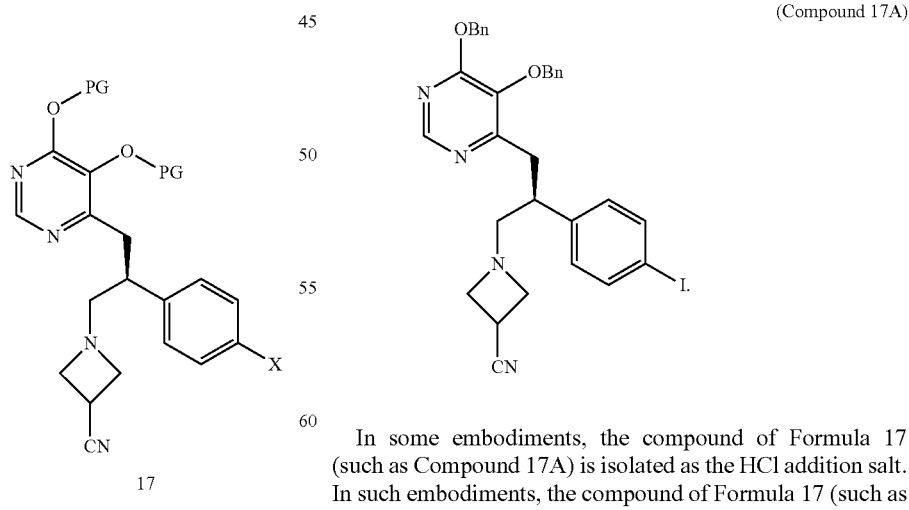

In some embodiments, the compound of Formula 17, or salt thereof, is Compound 17A:

In some embodiments, the aldehyde of Formula 15 and the compound of Formula 16, or a salt thereof, are treated with a suitable reducing agent in a suitable solvent to yield In some embodiments, the compound of Formula 17 (such as Compound 17A) is isolated as the HCl addition salt. In such embodiments, the compound of Formula 17 (such as Compound 17A) is converted to the free base for isolation and purification. In some embodiments, the compound of Formula 17 (such as Compound 17A) is isolated as the free base after aqueous extractive workup.

Step 14: Synthesis of a Compound of Formula 21

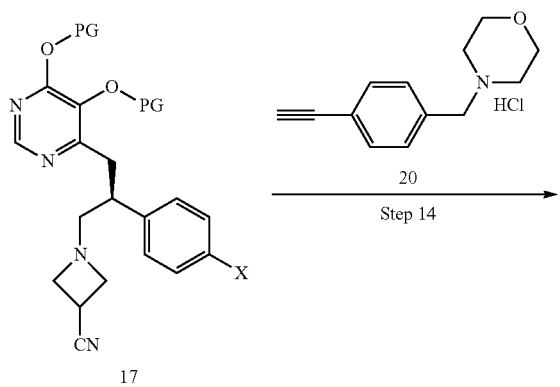

In some embodiments, the compound of Formula 17 is reacted with the compound of Formula 20 in the presence of a coupling catalyst, a suitable base, and in a suitable solvent to provide a compound of Formula 21.

In some embodiments, the coupling catalyst is a palladium catalyst. In some embodiments, the palladium catalyst is a palladium(0) catalyst. In other embodiments, the palladium catalyst is a palladium(II) catalyst. In some embodiments, the palladium catalyst is precoordinated with a ligand. In some embodiments, the palladium catalyst is $Pd(PPh_3)_2Cl_2$. In some embodiments, the palladium catalyst is $Pd(PPh_3)_3Cl$. In some embodiments, the palladium catalyst is $Pd(PPh_3)_4$. In some embodiments, the amount of palladium used is from about 0.005 equiv to about 0.1 equiv. In some embodiments, the amount of palladium used is about 0.005, 0.01, 0.02, 0.03, 0.04, 0.05, 0.06, 0.07, 0.08, 0.09, or 0.1 equiv. In some embodiments, the amount of palladium used is about 0.02 equiv.

In some embodiments, Step 14 further comprises adding an exogenous ligand. In some embodiments, the ligand is a phosphine ligand. In some embodiments, the ligand is an aliphatic phosphine ligand, such as trimethyl phosphine, tricyclohexylphosphine, tri-tert-butyl-phosphine or the like. In some embodiments, the ligand is an aromatic phosphine, such as XPhos, SPhos, JohnPhos, Amphos, triphenylphosphine, methyldiphenylphosphine, or the like. In some embodiments, the ligand is a phosphite ligand, such as trimethylphosphite, triphenylphosphite, or the like. In some embodiments, the ligand is a bis-phosphine ligand, such as diphenylphosphinomethane (dppm), diphenyl phosphinoethane (dppe), 1,1'-bis(diphenylphosphino)ferrocene (dppf), or the like. In some embodiments, the ligand is triphenylphospine.

In some embodiments, Step 14 further comprises adding a copper(I) cocatalyst. In some embodiments, the copper(I) cocatalyst in Step 1 is a copper(I) salt. In some embodiments, the copper(I) cocatalyst in Step 1 is CuCl, CuBr, or CuI. In some embodiments, the copper(I) cocatalyst is CuI. In some embodiments, the copper(I) cocatalyst is a copper(I)—N-heterocyclic carbene (Copper-NHC) complex. In some embodiments, the amount of copper(I) cocatalyst used in Step 1 is from about 0.001 equiv to about 0.1 equiv. In some embodiments, the amount of copper(I) cocatalyst used in Step 1 is about 0.001, 0.002, 0.003, 0.004, 0.005, 0.01, 0.02, 0.03, 0.04, 0.05, 0.06, 0.07, 0.08, 0.09, or 0.1 equiv. In some embodiments, the amount of copper(I) cocatalyst used in Step 1 is about 0.005 equiv.

In preferred embodiments, Step 13 does not comprise a copper(I) cocatalyst. In some instances, additional metals, such as copper, complicate the purification of the compounds described herein, or contaminate the final product, Compound A. In such instances, it is preferable to avoid the additional metal.

In some embodiments, the suitable base is an amine base. In some embodiments, the suitable base is a primary, a secondary, or a tertiary amine base. In some embodiments, the suitable base is a quaternary ammonium salt. In some embodiments, the suitable base is triethylamine, diisopropylethylamine, 1,2,2,6,6-pentamethylpiperidine, tributylamine, 1,8-diazabicycloundec-7-ene (DBU), or the like. In some embodiments, the suitable base is sec-butylamine. In some embodiments, the suitable base is tetrabutylammonium fluoride (TBAF).

In preferred embodiments, the suitable base is sec-butylamine or tetrabutylammonium fluoride (TBAF). Both of these bases allow the reaction to proceed without the addition of a copper co-catalyst. In a more preferred embodiment, the suitable base is sec-butylamine. In preferred embodiments, sec-butylamine is amenable to use in steel reaction vessels. In some embodiments, sec-butylamine is used in excess. In some embodiments, sec-butyl amine is used as a cosolvent.

In some embodiments, the suitable solvent is acetonitrile, dimethylformamide, diethyl ether, ethanol, tetrahydrofuran, isopropyl alcohol, 1,4-dioxane, toluene, water, or a combination thereof. In some embodiments, the suitable solvent is water.

In preferred embodiments, sec-butylamine and water are used in a ratio of about 5:1, about 4:1, about 3:1, about 2:1, or about 1:1 water to sec-butylamine.

In some embodiments, the compound of Formula 21, is Compound 21A:

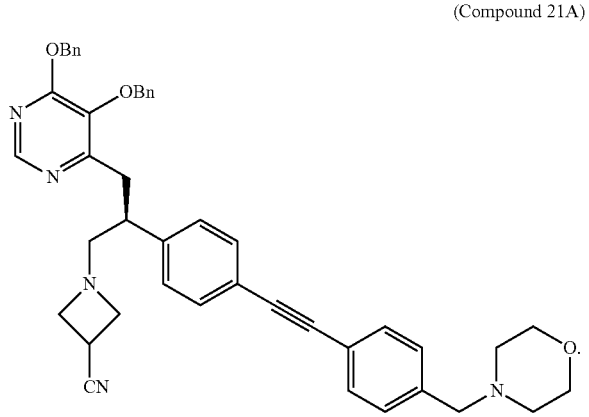 [SMILES: N#CC1CN(C[C@@H](Cc2ncnc(OCc3ccccc3)c2OCc2ccccc2)c2ccc(C#Cc3ccc(CN4CCOCC4)cc3)cc2)C1]

(Compound 21A)

Step 15: Synthesis of a Compound A

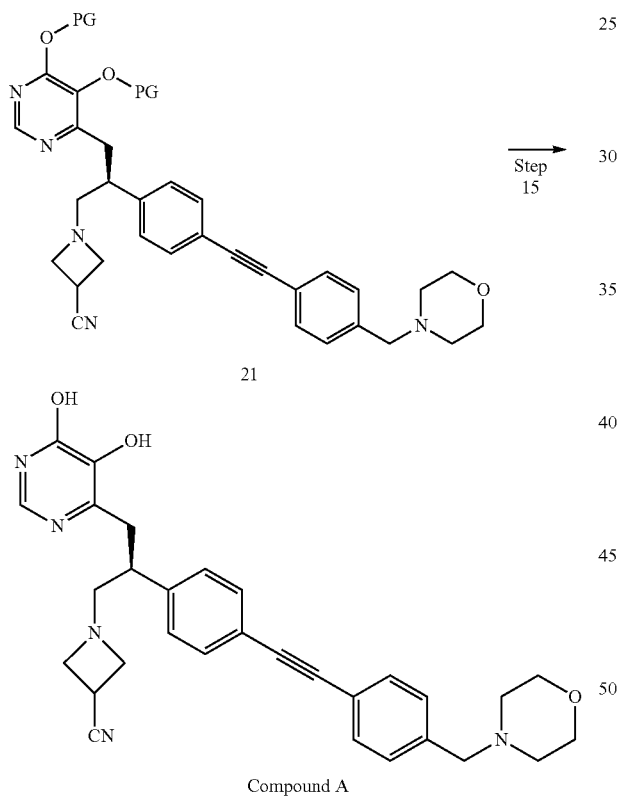

In some embodiments, the protected compound of Formula 21 is treated with appropriate deprotection conditions to yield Compound A. These conditions vary based on the nature of the protecting group(s) used. In some embodiments, the protecting groups are the same. In other embodiments the protecting groups are different. In some embodiments, the two protecting groups are removed in a single reaction. In other embodiments, two successive reactions are required for complete deprotection of the two protecting groups.

In some embodiments, the compound of Formula 21 is treated with a suitable reagent in a suitable solvent to facilitate the deprotection. In some embodiments, the suitable reagent is $H_2$/catalyst, HCl, HBr, TFA, TBAF, $BCl_3$, 9-I-BBN, $BF_3$—$OEt_2$, TMS-Cl, or TMS-Br, or the like.

In some embodiments, the suitable solvent is acetonitrile, dichloromethane, chloroform, dichloroethane, diethyl ether, tetrahydrofuran, isopropyl alcohol, 1,4-diaxane, toluene, anisole, water, or a combination thereof.

In some embodiments, when —O-PG is a benzyl ether, the suitable reagent is $H_2$/catalyst, TFA, $BCl_3$, or 9-I—BBN, or the like.

In preferred embodiments, when PG is Bn, the suitable reagent is TFA. In some such embodiments, Step 15 further comprises the addition of pentamethylbenzene. In such embodiments, a TFA/pentamethylbenzene deprotection provides higher yields and a cleaner reaction. In some such embodiments, the suitable solvent is anisole.

In some embodiments, when —O-PG is an acetal (as in a methoxymethyl group), the suitable reagent is HCl, HBr, or TMS-Br, or the like.

In some embodiments, when —O-PG is a silyl ether, or comprises a silyl group and an ether (as in [2-(trimethylsilyl)ethoxy]methyl group), the suitable reagent TBAF, or the like.

In some embodiments, the reaction is performed at a low temperature. In some embodiments, the reaction is performed at about 0° C. In some embodiments, the reaction mixture is allowed to warm to room temperature (about 25° C.).

Step 15-A: Crystallization of Compound A

In some embodiments, Compound A is recrystallized. In some embodiments, Compound A is recrystallized from acetonitrile, methanol, ethanol, isopropyl alcohol, acetone, methyl acetate, ethyl acetate, dichloromethane, chloroform, diethyl ether, diisopropyl ether, tert-butyl methyl ether, tetrahydrofuran, 2-methyltetrahydrofuran, dioxane, benzene, toluene, petroleum ether, pentane, hexane, heptane, cyclohexane, acetic acid, water, or a mixture thereof.

In some embodiments, Compound A is recrystallized from a mixture of acetic acid and tetrahydrofuran. In some embodiments, Compound A is recrystallized from a mixture of acetic acid and tetrahydrofuran in a ratio of about 2:1, about 1:1, about 1:2, about 1:3, about 1:4, about 1:5, about 1:6, about 1:7, about 1:8, or about 1:9 acetic acid to tetrahydrofuran.

In some instances, the compound of Formula 8 is synthesized as outlined in Scheme 5.

Scheme 5. Alternative Preparation of a compound of Formula 8

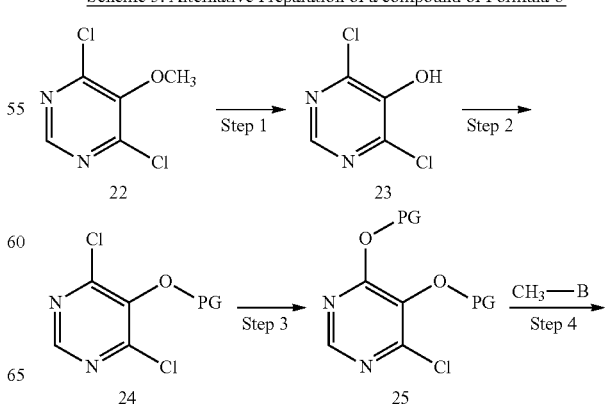

-continued

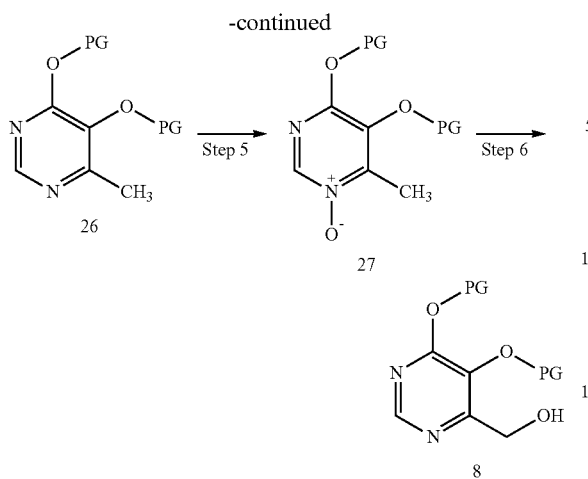

Briefly, in some embodiments, the methyl ether of Formula 22 is deprotected to yield a compound of Formula 23. In some embodiments, the compound of Formula 23 is treated with a suitable reagent to yield the protected compound of Formula 24. In some embodiments, treatment of the aryl halide 24 with a suitable alcohol (PG-OH) yields a compound of Formula 25. In some embodiments, the compound of Formula 25 is methylated under cross-coupling conditions with a compound having the formula $CH_3$—B, to yield the compound of Formula 26, wherein B is a boronic acid, boronate ester, or trifluoroborate. In some embodiments, the compound of Formula 26 is oxidized to yield a compound of Formula 27. Finally, in some embodiments, the N-oxide compound of Formula 27 undergoes a rearrangement to yield the compound of Formula 8.

As disclosed herein, variables in Scheme 5 are defined as follows: each PG is a suitable protecting group; and B is a boronic acid, boronate ester, or trifluoroborate.

In some embodiments, each PG is the same suitable protecting group. In some embodiments, each PG is a different suitable protecting group. In some embodiments, each —O-PG is an ether, a benzyl ether, an acetal, or a silyl ether; wherein each PG is the same protecting group. In some embodiments, each —O-PG is a benzyl ether, an acetal, or a silyl ether, wherein each PG is the same protecting group. In some embodiments, each PG is methyl, benzyl, p-methoxybenzyl, methoxymethyl, [2-(trimethylsilyl)ethoxy]methyl, triisopropylsilyl, or tert-butyldimethylsilyl. In some embodiments, each PG is benzyl.

Step 1: Synthesis of a Compound of Formula 23

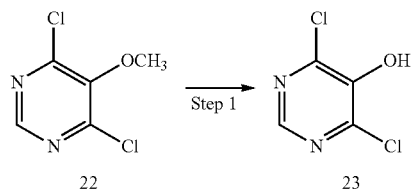 [SMILES: COc1c(Cl)ncnc1Cl ; Oc1c(Cl)ncnc1Cl]

In some embodiments, the methyl ether of Formula 22 is deprotected by treatment with a suitable reagent and in a suitable solvent to yield a compound of Formula 23. In some embodiments, the suitable reagent is $BBr_3$, pyridine-HCL, $BCl_3$, NaSEt, $AlCl_3$, or the like. In some embodiments, the suitable reagent is $AlCl_3$. In some embodiments, the suitable solvent is dimethylformamide, diethyl ether, tetrahydrofuran, 1,4-dioxane, toluene, dichloromethane, chloroform, dichloroethane, or the like, or a combination thereof. In some embodiments, the suitable solvent is dichloromethane, chloroform, or dichloroethane. In some embodiments, the suitable solvent is dichloroethane. In some embodiments, the reaction is performed at about 0° C. In some embodiments, the reaction mixture is allowed to warm to room temperature (about 25° C.). In some embodiments, the reaction begins at about 0° C. and is warmed to about 50° C.

In some embodiments, the compound of Formula 22 is Compound 22A:

(Compound 22A)

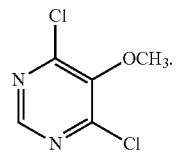

22A

In some embodiments, the compound of Formula 23 is Compound 23A:

(Compound 23A)

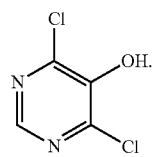

23A

Step 2: Synthesis of a Compound of Formula 24

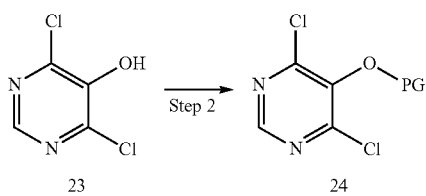

In some embodiments, a compound of Formula 23 is treated with a suitable reagent in a suitable solvent to yield the protected compound of Formula 24.

In some embodiments, the suitable reagent is a benzyl halide, such as a benzyl bromide, and a suitable base. In such embodiments, —O-PG is a benzyl ether. In some such embodiments, the suitable reagent is benzyl bromide or p-methoxybenzyl bromide, or the like. In such embodiments, PG is benzyl or p-methoxybenzyl, respectively, or the like. In some embodiments, the suitable reagent is benzyl bromide. In some embodiments, the suitable base is $Na_2CO_3$, $NaHCO_3$, $K_2CO_3$, $Li_2CO_3$, $Cs_2CO_3$, or the like. In some embodiments, the suitable base is $K_2CO_3$. In some embodiments, the suitable solvent is acetonitrile, dichloromethane, dimethylformamide, acetone, diethyl ether, ethanol, tetrahydrofuran, isopropyl alcohol, 1,4-dioxane, toluene, water, or a combination thereof. In some embodiments, the suitable solvent is acetone. In some embodiments, the reaction further comprises a phase transfer catalyst, such as tetrabutylammonium iodide (TBAI).

In other embodiments, the suitable reagent is a silyl chloride. In such embodiments, —O-PG is a silyl ether. In some such embodiments, the suitable reagent is triisopropylsilyl chloride or tert-butyldimethylsilyl chloride, or the like. In such embodiments, PG is triisopropylsilyl or tert-butyldimethylsilyl, respectively, or the like. In some embodiments, the suitable base is imidazole. In some embodiments, the suitable solvent is acetonitrile, dichloromethane, dimethylformamide, diethyl ether, ethanol, tetrahydrofuran, isopropyl alcohol, 1,4-dioxane, toluene, water, or a combination thereof.

In other embodiments, the suitable reagent is a chloromethyl ether. In such embodiments, —O-PG is an acetal. In some such embodiments, the suitable reagent is [2-(trimethylsilyl)ethoxy]methyl chloride or chloromethyl methyl ether, or the like. In such embodiments, PG is [2-(trimethylsilyl)ethoxy]methyl or methoxymethyl, respectively, or the like. In some embodiments, the suitable base is triethylamine, diisopropylethylamine, 1,2,2,6,6-pentamethylpiperidine, tributylamine, or 1,8-diazabicyclo[5.4.0]undec-7-ene (DBU), or the like. In some embodiments, the suitable solvent is acetonitrile, dichloromethane, dimethylformamide, diethyl ether, ethanol, tetrahydrofuran, isopropyl alcohol, 1,4-dioxane, toluene, water, or a combination thereof.

In some embodiments, the compound of Formula 24 is Compound 24A:

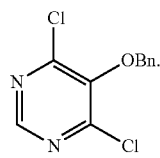

(Compound 24A)

Step 3: Synthesis of a Compound of Formula 25

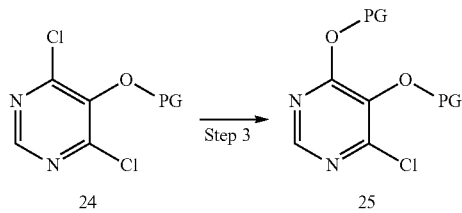

In some embodiments, treatment of the aryl halide of Formula 24 with a suitable alcohol (PG-OH) yields a compound of Formula 25. In such embodiments, —O-PG is an ether or a benzyl ether.

In some embodiments, the suitable alcohol (R—OH) is methanol, ethanol, or benzyl alcohol. In some embodiments, the suitable alcohol (R—OH) is benzyl alcohol. In some such embodiments, the compound of Formula 25 is a compound of Formula 25-I:

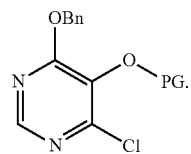

Formula 25-I

In some embodiments, the reaction comprises a suitable base and is run in a suitable solvent. In some embodiments, the suitable base is sodium hydride, triethylamine, diisopropylethylamine, sec-butylamine, 1,2,2,6,6-pentamethylpiperidine, tributylamine, or 1,8-diazabicyclo[5.4.0]undec-7-ene (DBU), or the like. In some embodiments, the suitable base is sodium hydride. In some embodiments, the suitable solvent is acetonitrile, dimethylformamide, diethyl ether, ethanol, tetrahydrofuran, isopropyl alcohol, 1,4-dioxane, toluene, water, or a combination thereof. In some embodiments, the suitable solvent is tetrahydrofuran. In other embodiments, the suitable solvent is the suitable alcohol having formula R—OH. In some such embodiments, the suitable solvent is methanol, ethanol, or benzyl alcohol.

In some embodiments, the compound of Formula 25 or Formula 25-I is Compound 6A:

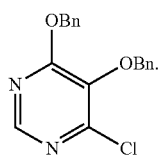

(Compound 25A)

Step 4: Synthesis of a Compound of Formula 26

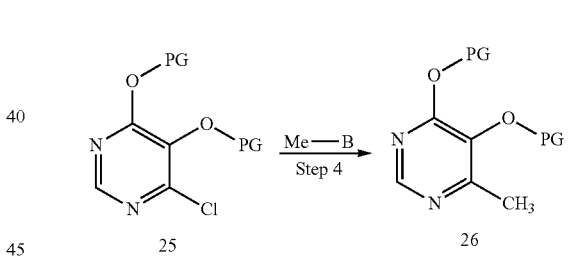

In some embodiments, the compound of Formula 25 is reacted with a compound of the formula CH$_3$—B in the presence of a coupling catalyst, a suitable base, and in a suitable solvent to provide a compound of Formula 26, wherein B is a boronic acid, boronate ester, or trifluoroborate.

In some embodiments, B is a boronic acid or a boronic ester. In some embodiments, B is

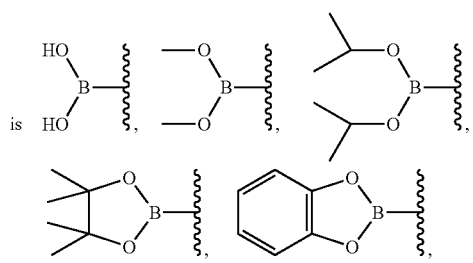

-continued

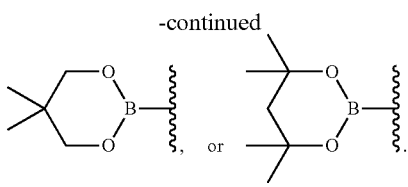

In some embodiments, B is a boronic acid. In some embodiments, B is

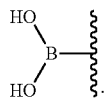

In some embodiments, B is a boronic ester. In some embodiments, B is a trifluoroborate. In some embodiments, B is

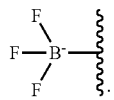

In some embodiments, the coupling catalyst is a palladium catalyst. In some embodiments, the palladium catalyst is a palladium(0) catalyst. In other embodiments, the palladium catalyst is a palladium(II) catalyst. In some embodiments, the palladium catalyst is precoordinated with a ligand. In some embodiments, the palladium catalyst is $Pd(PPh_3)_2Cl_2$. In some embodiments, the palladium catalyst is $Pd(PPh_3)_3Cl$. In some embodiments, the palladium catalyst is $Pd(PPh_3)_4$. In some embodiments, the amount of palladium used is from about 0.005 equiv to about 0.1 equiv. In some embodiments, the amount of palladium used is about 0.005, 0.01, 0.02, 0.03, 0.04, 0.05, 0.06, 0.07, 0.08, 0.09, or 0.1 equiv. In some embodiments, the amount of palladium used is about 0.02 equiv.

In some embodiments, the suitable base is an amine base. In some embodiments, the suitable base is a tertiary amine base. In some embodiments, the suitable base is triethylamine, diisopropylethylamine, 1,2,2,6,6-pentamethylpiperidine, tributylamine, 1,8-diazabicycloundec-7-ene (DBU), or the like. In other embodiments, the suitable base is an inorganic base. In some embodiments, the suitable base is $NaHCO_3$, NaOAc, KOAc, $Ba(OH)_2$, $Li_2CO_3$, $Na_2CO_3$, $K_2CO_3$, $Cs_2CO_3$, $Na_3PO_4$, $K_3PO_4$, CsF, or the like. In some embodiments, the suitable base is KOAc.

In some embodiments, Step 4 further comprises adding an exogenous ligand. In some embodiments, the ligand is a phosphine ligand. In some embodiments, the ligand is an aliphatic phosphine ligand, such as trimethyl phosphine, tricyclohexylphosphine, tri-tert-butyl-phosphine or the like. In some embodiments, the ligand is an aromatic phosphine, such as XPhos, SPhos, JohnPhos, Amphos, triphenylphosphine, methyldiphenylphosphine, or the like. In some embodiments, the ligand is a phosphite ligand, such as trimethylphosphite, triphenylphosphite, or the like. In some embodiments, the ligand is a bis-phosphine ligand, such as diphenylphosphinomethane (dppm), diphenyl phosphinoethane (dppe), 1,1'-bis(diphenylphosphino)ferrocene (dppf), or the like. In some embodiments, the ligand is triphenylphospine.

In some embodiments, the suitable solvent is acetonitrile, dimethylformamide, diethyl ether, ethanol, tetrahydrofuran, isopropyl alcohol, 1,4-dioxane, toluene, water, or a combination thereof. In some embodiments, the suitable solvent is 1,4-dioxane.

In some embodiments, the reaction is performed at an elevated temperature. In some embodiments, the reaction is performed at about 100° C.

In embodiments where the compound of Formula 25 is a compound of Formula 25-I, the compound of Formula 26 is a compound of Formula 26-I:

Formula 26-I

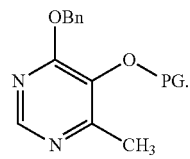

In some embodiments, the compound of Formula 26 or Formula 26-I is Compound 26A:

(Compound 26A)

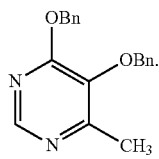

Step 5: Synthesis of a Compound of Formula 27

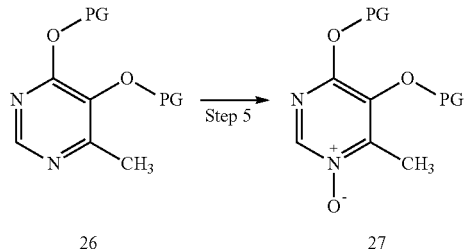

In some embodiments, the compound of Formula 26 is treated with a suitable oxidation reagent in a suitable solvent to yield a compound of Formula 27. In some embodiments, the suitable oxidation reagent is a peroxyacetic acid or a peroxybenzoic acid. In some embodiments, the suitable oxidation reagent is peracetic acid, m-chloroperoxybenzoic acid (mCPBA), or the like. In some embodiments, the suitable oxidation reagent is mCPBA. In other embodiments, the suitable oxidation reagent is hydrogen peroxide. In some embodiments, the suitable solvent is dichloromethane, chloroform, dichloroethane, or the like, or a combination thereof. In some embodiments, the suitable solvent is dichloromethane.

In embodiments where the compound of Formula 26 is a compound of Formula 26-I, the compound of Formula 27 is a compound of Formula 27-I:

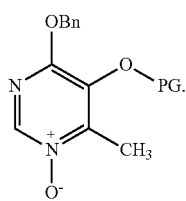

Formula 27-I

In some embodiments, the compound of Formula 27 or Formula 27-I is Compound 27A:

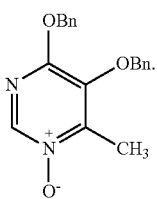

(Compound 27A)

Step 6: Synthesis of a Compound of Formula 8

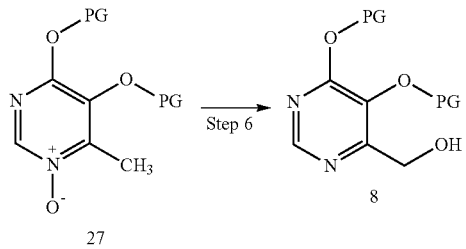

In some embodiments, the compound of Formula 27 is treated with a suitable reagent in a suitable solvent to yield a compound of Formula 8. In some embodiments, the compound of Formula 27 undergoes a [3,3]-sigmatropic rearrangement when treated with a suitable reagent in a suitable solvent to yield a compound of Formula 8. In some embodiments, the suitable reagent is an acid anhydride. In some embodiments, the suitable reagent is acetic anhydride, trifluoroacetic anhydride (TFAA), or the like. In some embodiments, the suitable reagent is TFAA. In some embodiments, the suitable solvent is acetonitrile, dichloromethane, chloroform, dichloroethane, dimethylformamide, diethyl ether, tetrahydrofuran, 1,4-dioxane, toluene, or a combination thereof. In some embodiments, the suitable solvent is dichloromethane.

In embodiments where the compound of Formula 27 is a compound of Formula 27-I, the compound of Formula 8 is a compound of Formula 8-I:

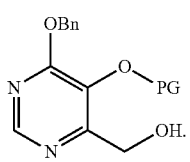

Formula 8-I

In some embodiments, the compound of Formula 8 or Formula 8-I is Compound 8A:

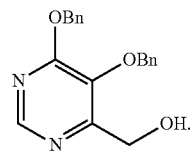

(Compound 8A)

Due to the fact that the synthetic methods described above utilize a transition metal catalyst, purification steps are performed to reduce the amount of palladium in the product Purification steps to reduce the amount of palladium in a product are conducted so that active pharmaceutical ingredients meet palladium specification guidelines. ("Guideline on the Specification Limits for Residues of Metal Catalysts" European Medicines Agency *Pre-authorisation Evaluation of Medicines for Human Use*, London, January 2007, Doc. Ref. CPMP/SWP/QWP/4446/00 corr.). In some embodiments, purification steps to reduce the amount of palladium in a product includes, but is not limited to, treatment with solid trimercaptotriazine (TMT), polystyrene-bound TMT, mercapto-porous polystyrene-bound TMT, polystyrene-bound ethylenediamine, activated carbon, glass bead sponges, Smopex™, silica bound scavengers, thiol-derivatized silica gel, N-acetylcysteine, n-Bu₃P, crystallization, extraction, l-cysteine, n-Bu₃P/lactic acid (Garrett et al., *Adv. Synth. Catal.* 2004, 346, 889-900). In some embodiments, activated carbon includes but is not limited to

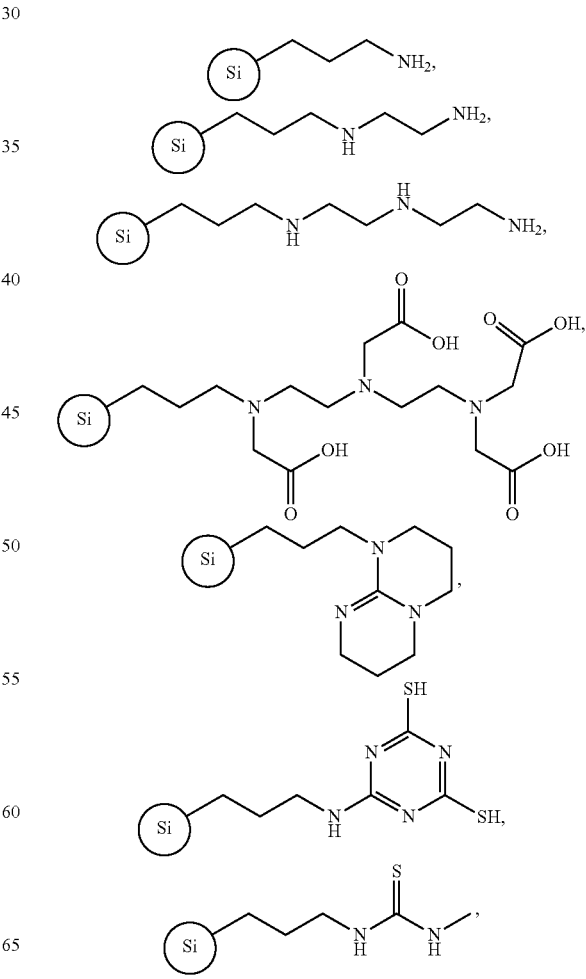

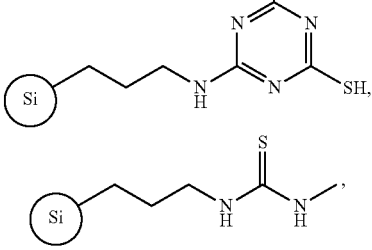

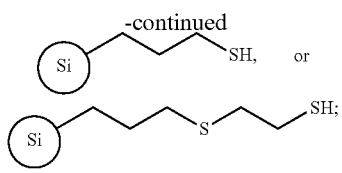

where

silica bound scavengers include but are not limited to, embodiments, the purification steps to reduce the amount of palladium include the use of activated carbon, derivatized silica gel (e.g., thiol derivatized silica gel), or combinations thereof.

In some embodiments, the compound of Formula 21 (such as Compound 21A), the compound of Formula 26 (such as 26A), or Compound A is further treated with a metal scavenger to remove residual palladium. In some embodiments, the metal scavenger comprises $SiO_2$, charcoal, aqueous solution of L-cysteine, a Silicycle metal scavenger, Si-thiol, SiliaBond DMT, SiliaBond Cysteine, or 3-mercaptopropyl ethyl sulfide silica. In some embodiments, the scavenger loading (w/w) is about 1:3, about 1:2, or about 1:1.

In some of these embodiments, palladium levels are reduced to about 10 ppm. In some of these embodiments, palladium levels are reduced sufficiently to be undetectable.

In some embodiments, the presence of residual heavy metal (e.g. palladium) impurities is determined by utilizing methods known in the art. In some embodiments, the presence of residual heavy metal (e.g. palladium) impurities is determined by the use of inductively coupled plasma mass spectrometry (ICP-MS). In some embodiments, the presence of residual heavy metal (e.g. palladium) impurities is determined by the use of techniques described in U.S. Pharmacopeia General Chapter <231> Heavy Metals.

In some embodiments, compounds described herein are synthesized as outlined in the Examples.

Definitions

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

The term "halo" or, alternatively, "halogen" or "halide" means fluoro, chloro, bromo or iodo. In some embodiments, halo is fluoro, chloro, or bromo.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "acceptable" with respect to a formulation, composition or ingredient, as used herein, means having no persistent detrimental effect on the general health of the subject being treated.

The term "prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7 9, 21 24 (Elsevier, Amsterdam). A discussion of prodrugs is provided in Higuchi, T., et al., "Pro drugs as Novel Delivery Systems," A.C.S. Symposium Series, Vol. 14, and in Bioreversible Carriers in Drug Design, ed. Edward B. Roche, American Pharmaceutical Association and Pergamon Press, 1987. The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally. In some embodiments, the compounds and compositions described herein are administered intravenously.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. the LpxC inhibitory compound disclosed herein, or an isotopic variant, tautomer, prodrug, pharmaceutically acceptable salt, solvate, or hydrate thereof, and a co-agent, are both administered to a patient simultaneously in the form of a single entity or dosage. The term "non-fixed combination" means that the active ingredients, e.g. the LpxC inhibitory compound disclosed herein, or an isotopic variant, tautomer, prodrug, pharmaceutically acceptable salt, solvate, or hydrate thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Further Forms of Compound A

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zurich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound disclosed herein with an acid. In some embodiments, the compound disclosed herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1, 5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, pharmaceutically acceptable salts are obtained by reacting a compound disclosed herein with a base. In some embodiments, the compound disclosed herein is acidic and is reacted with abase. In such situations, an acidic proton of the compound disclosed herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents inactive pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound A, comprise an organic solvent(s). In some embodiments, compositions comprising Compound A include a residual amount of an organic solvent(s). In some embodiments, compositions comprising Compound A comprise a residual amount of a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

In some embodiments, the compositions comprising Compound A include a detectable amount of an organic solvent. In some embodiments, the organic solvent is a Class 3 solvent.

In other embodiments are compositions comprising Compound A wherein the composition comprises a detectable amount of solvent that is less than about 1%, wherein the solvent is selected from acetone, 1,2-dimethoxyethane, acetonitrile, ethyl acetate, tetrahydrofuran, methanol, ethanol, heptane, and 2-propanol. In a further embodiment are compositions comprising Compound A wherein the composition comprises a detectable amount of solvent which is less than about 5000 ppm. In yet a further embodiment are compositions comprising Compound A, wherein the detectable amount of solvent is less than about 5000 ppm, less than about 4000 ppm, less than about 3000 ppm, less than about 2000 ppm, less than about 1000 ppm, less than about 500 ppm, or less than about 100 ppm.

The methods and formulations described herein include the use of N-oxides (if appropriate), or pharmaceutically acceptable salts of compounds having the structure disclosed herein, as well as active metabolites of these compounds having the same type of activity.

In some embodiments, sites on the organic radicals (e.g. alkyl groups, aromatic rings) of compounds disclosed herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{4}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or altered metabolic pathways to reduce undesirable metabolites or reduced dosage requirements.

In some embodiments, one or more hydrogen atoms on Compound Aare replaced with deuterium. In some embodiments, substitution with deuterium affords certain therapeutic advantages resulting from greater metabolic stability, such as, for example, increased in vivo half-life or reduced dosage requirements.

In one aspect, described is a compound with the following structure:

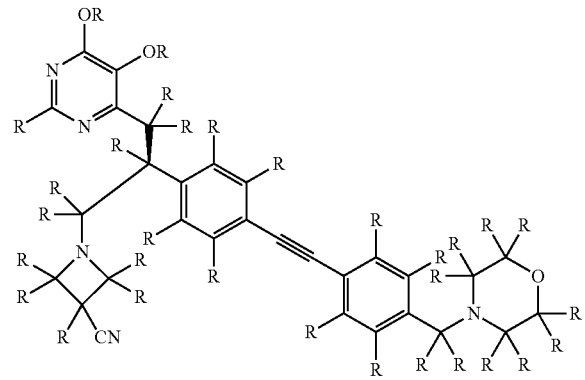

wherein,
 each R is independently selected from hydrogen or deuterium,
 or an isotopic variant, tautomer, pharmaceutically acceptable salt, solvate, or hydrate thereof.

In some embodiments, the compounds disclosed herein possess one or more stereocenters and each stereocenter exists independently in either the R or S configuration. For example, in some embodiments, the compound disclosed herein exists in the R configuration when one stereocenter is present. In other embodiments, the compound disclosed herein exists in the S configuration when one stereocenter is present. In some embodiments, the compound disclosed herein exists in the RR configuration when two stereocenters are present. In some embodiments, the compound disclosed herein exists in the R S configuration when two stereocenters are present. In some embodiments, the compound disclosed herein exists in the SS configuration when two stereocenters are present. In some embodiments, the compound disclosed herein exists in the SR configuration when two stereocenters are present.

The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds disclosed herein are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers of compounds disclosed herein is carried out using covalent diastereomeric derivatives of the compounds described herein. In another embodiment, diastereomers of compounds disclosed herein are separated by separation/resolution techniques based upon differences in solubility. In other embodiments, separation of stereoisomers of compounds disclosed herein is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

Separation of individual enantiomers from a racemic mixture is possible by the use of chiral supercritical fluid chromatography (SFC) or chiral high performance liquid chromatography (HPLC). In some embodiments, enantiomers described herein are separated from each other by the use of chiral SFC or chiral HPLC. In some embodiments, compounds disclosed herein that include one or more chiral centers (e.g. compounds disclosed herein that include the moiety trans-octahydro-1H-pyrido[3,4-b]morpholin-6-yl) are separated into individual enantiomers using chiral SFC or chiral HPLC. A wide variety of conditions and suitable columns are available.

Daicel polysaccharide chiral stationary phases (CSPs) are among the columns used for chiral SFC separations. In some embodiments, Daicel analytical immobilised and coated CHIRALPAK and CHIRALCEL HPLC columns can be used for SFC analysis.

In some embodiments, screening for the suitability of using a SFC column is performed on the four main immobilised phases (CHIRALPAK IA, IB, IC and ID) and the four main coated columns (CHIRALPAK AD and AS and CHIRALCEL OD and OJ), with varying concentrations of organic modifier. A variety of column phases are available, including but not limited to OD and OJ, OX and OZ chlorinated phases, and a range of complementary cellulose based CHIRALCEL phases including OA, OB, OC, OF, OG and OK.

Non-limiting examples of chiral selectors contemplated for use in the separation of enantiomers include amylose tris (3,5-dimethylphenylcarbamate), cellulose tris (3,5-dimethylphenylcarbamate), cellulose tris (3,5-dichlorophenylcarbamate), amylose tris (3-chlorophenylcarbamate), amylosetris (3,5-dichlorophenylcarbamate), amylosetris (3-chloro, 4-methylphenylcarbamate), amylose tris ((S)-alpha-methylbenzylcarbamate), amylose tris (5-chloro-2-methylphenylcarbamate), cellulose tris (4-methylbenzoate), cellulose tris (4-chloro-3-methylphenylcarbamate), and cellulose tris (3-chloro-4-methylphenylcarbamate).

Non-limiting examples of chiral columns contemplated for use in the separation of enantiomers include CHIRAL- PAK IA SFC, CHIRALPAK AD-H SFC, CHIRALPAK IB SFC, CHIRALCEL OD-H SFC, CHIRALPAK IC SFC, CHIRALPAK ID SFC, CHIRALPAK IE SFC, CHIRALPAK IF SFC, CHIRALPAK AZ-H SFC, CHIRALPAK AS-H SFC, CHIRALPAK AY-H SFC, CHIRALCEL OJ-H SFC, CHIRALCEL OX—H SFC, and CHIRALCEL OZ—H SFC.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Pharmaceutical Compositions

In certain embodiments, the heterocyclic LpxC inhibitory compound as described herein is administered as a pure chemical. In other embodiments, the heterocyclic LpxC inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one heterocyclic LpxC inhibitory compound as described herein, or a stereoisomer, pharmaceutically acceptable salt, or N-oxide thereof, together with one or more pharmaceutically acceptable carriers. The carrier(s)(or excipient(s)) is acceptable or suitable if the carrier is compatible with the other ingredients of the composition and not deleterious to the recipient (i.e., the subject or patient) of the composition.

One embodiment provides a pharmaceutical composition comprising Compound A, or an isotopic variant, tautomer, prodrug, pharmaceutically acceptable salt, solvate, or hydrate thereof, and at least one pharmaceutically acceptable excipient.

In some embodiments, the pharmaceutical composition is in a dosage form for dosing or administration by injection. In some embodiments, the pharmaceutical composition is in a dosage form for intravenous (I.V.) injection or infusion, or intramuscular, subcutaneous, or intradermal injection. In some embodiments, the pharmaceutical composition is in a dosage form for I.V. injection or infusion. In some embodiments, the pharmaceutical composition is a solution.

In some embodiments, the pharmaceutical composition is in a dosage form for oral dosing or administration. In some embodiments, the dosage form is a liquid. In some embodiments, the dosage form is a suspension, solution, syrup, or elixir. In some embodiments, the dosage form is a suspension. In some embodiments, the dosage form is a nanosuspension. In some embodiments, the dosage form is a solution. In other embodiments, the dosage form is a tablet or a capsule.

In some embodiments, the at least one pharmaceutically acceptable excipient is a cosolvent, oil, surfactant, complexing agent, a solubilizing polymer, a P-gp modulator, a buffering agent, or a combination thereof.

In certain embodiments, the heterocyclic LpxC inhibitory compound disclosed herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

LpxC, Lipid A and Gram-Negative Bacteria

Metalloproteins influence a vast diversity of biological systems, biological processes, and diseases. For example, UDP-{3-O—[(R)-3-hydroxymyristoyl]}-N-acetylglucosamine deacetylase (LpxC) is an essential enzyme involved in the first committed step in lipid A biosynthesis for gram-negative bacteria. Lipid A is an essential component of the outer membrane of gram-negative bacteria. LpxC is a zinc(II)-dependent metalloenzyme, with two histidines and an aspartic acid residue bound to the zinc(II) ion. Structures of LpxC show the zinc(II) ion is bound to two water molecules, both of which have been implicated in the mechanism of the enzyme. LpxC is highly conserved across strains of gram-negative bacteria, making LpxC an attractive target to treat gram-negative infections.

In recent years, there has been an increase in resistant and multi-drug resistant strains of bacteria. Thus, there is a need for new antibiotics, especially with new mechanisms of action. There remains a need for metalloprotein modulators of LpxC useful in the field of therapeutics, diagnostics, and research.

One embodiment provides a method of inhibiting UDP-{3-O—[(R)-3-hydroxymyristoyl]}-N-acetylglucosamine deacetylase enzyme comprising contacting the enzyme with the LpxC inhibitory compound disclosed herein.

Methods of Treatment

Disclosed herein are methods of treating disease wherein the inhibition of bacterial growth is indicated. Such disease includes gram-negative bacterial infection. In some embodiments, the method of treating a gram-negative bacterial infection in a patient in need thereof comprises administering to the patient a pharmaceutical composition comprising the LpxC inhibitory compound disclosed herein, or an isotopic variant, tautomer, prodrug, pharmaceutically acceptable salt, solvate, or hydrate thereof, and a pharmaceutically acceptable excipient. In some embodiments, the gram-negative bacterial infection is selected from pneumonia, sepsis, cystic fibrosis, intra-abdominal infection, skin infections and urinary tract infection. In some embodiments, the gram-negative bacterial infection is a urinary tract infection (UTI), a hospital acquired/ventilator-associated pneumonia (HAPNAP), or an intra-abdominal infection (IAI). In some embodiments, the gram-negative bacterial infection is selected from chronic urinary tract infections, complicated urinary tract infections, cystitis, pyelonephritis, urethritis, recurrent urinary tract infections, bladder infections, urethral infections, and kidney infections. In some embodiments, the compounds described herein are used for the treatment of chronic urinary tract infections. In some embodiments, the compounds described herein are used for the treatment of complicated urinary tract infections. In other embodiments, the compounds described herein are used for the treatment of complicated intra-abdominal infection. In some embodiments, the compounds described herein are used for the treatment of chronic intra-abdominal infection. In other embodiments, the compounds described herein are used for the treatment of hospital acquired pneumonia (HAP) or ventilator associated pneumonia (VAP). In some embodiments the administration is to treat an existing infection. In some embodiments the administration is provided as prophylaxis.

In some embodiments, the LpxC inhibitory compound described herein, or an isotopic variant, tautomer, prodrug, pharmaceutically acceptable salt, solvate, or hydrate thereof, is used for treating conditions caused by the bacterial production of endotoxin and, in particular, by gram-negative bacteria and bacteria that use LpxC in the biosynthesis of lipopolysaccharide (LPS) or endotoxin. In some embodiments, the method of treating a condition caused by endotoxin or LPS in a patient in need thereof comprises administering to the patient a pharmaceutical composition comprising the LpxC inhibitory compound disclosed herein, or an isotopic variant, tautomer, prodrug, pharmaceutically acceptable salt, solvate, or hydrate thereof, and a pharmaceutically acceptable excipient. In another embodiment, the heterocyclic LpxC inhibitory compound and formulations as described herein are useful in the treatment of conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). In some embodiments, the method of treating a condition caused by endotoxin or LPS in a patient in need thereof comprises administering to the patient a pharmaceutical composition comprising the LpxC inhibitory compound disclosed herein, or an isotopic variant, tautomer, prodrug, pharmaceutically acceptable salt, solvate, or hydrate thereof, and a pharmaceutically acceptable excipient, wherein the condition caused by endotoxin or LPS is selected from sepsis, septic shock, systemic inflammation, localized inflammation, chronic obstructive pulmonary disease (COPD) and acute exacerbations of chronic bronchitis (AECB).

In other embodiments, the LpxC inhibitory compound described herein, or an isotopic variant, tautomer, prodrug, pharmaceutically acceptable salt, solvate, or hydrate thereof, can be used for the treatment of a serious or chronic respiratory tract infection or complicated urinary tract infections including serious lung and nosocomial infections such as those caused by *Enterobacter aerogenes, Enterobacter cloacae, Escherichia coli, Klebsiella pneumoniae, Klebsiella oxytoca, Kluyvera ascorbata, Kluyvem cryocrescene, Shigella sonnei, Proteus mirabilis, Serratia marcescens, Stenotrophomonas maltophilia, Pseudomonas aeruginosa, Burkholderia cepacia, Acinetobacter baumannii, Alcaligenes xylosaxidans, Flavobacterium menmgosepticum, Providencia sluarlii* and *Citrobacter freundii, Haemophilus influenzae, Kluyvera species, Legionella species, Moraxella catarrhalis, Enterobacter species, Acinetobacter species, Klebsiella species, Burkholderia species* and *Proteus* species, and infections caused by other bacterial species such as *Neisseria species, Shigella species, Salmonella species, Helicobacler pylori, Vibrionaceae* and *Bordetella* species as well as the infections caused by a *Brucella species, Francisella tularensis* and/or *Yersinia pestis*.

In one embodiment provided herein is a method of treating a gram-negative bacterial infection in a patient in need thereof comprising administering to the patient a pharmaceutical composition comprising the LpxC inhibitory compound disclosed herein, or an isotopic variant, tautomer, prodrug, pharmaceutically acceptable salt, solvate, or hydrate thereof, and at least one pharmaceutically acceptable excipient.

One embodiment provides a method wherein the gram-negative bacterial infection is selected from pneumonia, sepsis, cystic fibrosis, intra-abdominal infection, skin infection and urinary tract infection.

One embodiment provides a method wherein the gram-negative bacterial infection is selected from chronic urinary tract infection, complicated urinary tract infection, cystitis, pyelonephritis, urethritis, recurrent urinary tract infections, bladder infections, urethral infections and kidney infections.

One embodiment provides a method wherein the gram-negative bacterial infection is chronic urinary tract infections. One embodiment provides a method wherein the gram-negative bacterial infection is complicated urinary tract infections. One embodiment provides a method wherein the administration is to treat an existing infection. One embodiment provides a method wherein the administration is provided as prophylaxis.

In some embodiments, the LpxC inhibitory compound described herein, or an isotopic variant, tautomer, prodrug, pharmaceutically acceptable salt, solvate, or hydrate thereof, is not active against gram-positive bacteria. In some embodiments, the LpxC inhibitory compound described herein, or an isotopic variant, tautomer, prodrug, pharmaceutically acceptable salt, solvate, or hydrate thereof is not active against *Staphylococcus aureus, Enterococcus faecalis, Streptococcus pyogenes, Bacillus thuringiensis, Lactobacillus rhamnosm, Staphylococcus epidermidis, Bidobacterium breve, Clostridiwn difficile, Clostridium sordellii, Peptostreptococcus anaerobius, Streptococcus pneumoniae, Corynebacterium jeikeium, Propionibacterim acnes, Listeria monocytogenes*, and/or *Nocardia cyriacigeorgica* complex. Most gut bacteria are Gram-positive, including *C. difficile*. Therefore, in some embodiments, the lack of activity against gram-positive bacteria is a benefit. In some embodiments, use of the LpxC inhibitory compound described herein, or an isotopic variant, tautomer, prodrug, pharmaceutically acceptable salt, solvate, or hydrate thereof, to treat a gram-negative bacterial infection, as described herein, has no effect on the gut microflora and thus reduces the risk of secondary infections from, for example, *C. docile*.

Combination Therapy

In some instances, Gram-negative bacteria are more resistant to a larger number of antibacterials and chemotherapeutic agents than are gram-positive bacteria due in part to their outer membrane, which acts as an efficient permeability barrier.

A survey of recently reported antibacterials of natural origin showed that over 90% lacked activity against *Escherichia coli*, although they were active against gram-positive bacteria. Young and Silver (J. Bacteriol. 173(12):3609-14 (1991)) demonstrated that an envA1 strain, having an altered outer membrane, is sensitive to a variety of large and hydrophobic antibacterials to which wild type *E. coli* is resistant. Additionally, Vaara, et al., (Antimicrobial Agents and Chemotherapy 37(11):2255-2260 (1993)) review a variety of outer membrane-defective mutants of *E. coli* and *S. typhimurium* that show greater susceptibility than the corresponding wild type strain to a variety of antibacterial agents.

In some embodiments, the present invention provides synergistic combinations of antibacterial agents with the LpxC inhibitory compound or pharmaceutical compositions disclosed herein. In some embodiments, the LpxC inhibitory compound disclosed herein has both intrinsic antibacterial properties as well the ability to improve permeability of the outer membrane of gram-negative bacteria to other antibacterial agents. In some embodiments, the antibacterial agent is selected from the group consisting of vancomycin, linezolid, azithromycin, imipenem, teicoplanin, daptomycin, clindamycin, rifampin, cefotaxime, gentamicin, novobiocin, and telavancin.

The use of such synergistic combinations of drugs could have many advantages over conventional single compound therapy, including lowered side-effects of the antibacterial agent due to lower doses used or to shorter time of treatment, more rapid cure of infection shortening hospital stays, increasing spectrum of pathogens controlled, and decreasing incidence of development of resistance to antibiotics.

Articles of Manufacture and Kits

Disclosed herein, in certain embodiments, are kits and articles of manufacture for use with one or more methods described herein. In some embodiments, additional components of the kit comprises a carrier, package, or container that is compartmentalized to receive one or more containers such as vials, tubes, and the like, each of the container(s) comprising one of the separate elements to be used in a method described herein. Suitable containers include, for example, bottles, vials, plates, syringes, and test tubes. In one embodiment, the containers are formed from a variety of materials such as glass or plastic.

The articles of manufacture provided herein contain packaging materials. Examples of pharmaceutical packaging materials include, but are not limited to, bottles, tubes, bags, containers, and any packaging material suitable for a selected formulation and intended mode of use.

For example, the container(s) include one or more of the compounds described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Other embodiments and uses will be apparent to one skilled in the art in light of the present disclosures. The following examples are provided merely as illustrative of various embodiments and shall not be construed to limit the invention in any way.

Examples

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (S) and coupling constants, J are reported in Hertz. For proton spectra the solvent peak was used as the reference peak.

The following abbreviations and terms have the indicated meanings throughout:

AcOH or HOAc=acetic acid
Amb=ambient temperature and humidity
ATCC=American Type Culture Collection
AUC=area under the curve
Bn=benzyl
BnOH=benzylalcohol
CPME=cyclopropyl methyl ether
CV=coefficient of variation
DBU=1,8-diazabicyclo[5.4.0]undec-7-ene
DCE=1,2-dichloroethane
DCM=dichloromethane or methylene chloride
DMF=N,N-dimethylformamide
DSM=German Collection of Microorganisms
eq or eq. or equiv.=equivalent(s)
Et=ethyl
$Et_3N$=triethylamine
EtOAc or EA=ethyl acetate
EtOH=ethanol
g=gram
h or hr=hour
HPβCD=(2-hydroxypropyl)-p-cyclodextrin
HP-55=hydroxypropyl methylcellulose phthalate
HPLC=high pressure liquid chromatography
HPMC 606=hydroxypropyl methylcellulose 606
IPA=isopropyl alcohol
kg or Kg=kilogram
L=liter
LC/MS=LCMS=liquid chromatography-mass spectrometry
LiHMDS=lithium bis(trimethylsilyl)amide or lithium hexamethyldisilazide
LpxC=UDP-{3-O—[(R)-3-hydroxymyristoyl]}-N-acetylglucosamine deacetylase
LRMS=low resolution mass spectrometry
m/z=mass-to-charge ratio
mCPBA=meta-chloroperoxybenaoic acid
Me=methyl
MeOH=methanol
mg=milligram
MIC=minimum inhibitory concentration.
min=minute
mL=milliliter mmol=millimole
MTBE=methyl tert-butyl ether
NaBH(OAc)₃=sodium triacetoxyborohydride
NaOEt=sodium ethoxide
NCTC National Collection of Type Cultures
NEQAS=United Kingdom National External Quality Assessment Scheme
NMM=N-methylmorpholine
NMR=nuclear magnetic resonance
PBS=phosphate buffered saline
PdCl₂(PPh₃)₂=dichlorobis(triphenylphosphine)palladium (II)
Ph=phenyl
rt or RT=room temperature
SHEβCD=sulfobutylether-β-cyclodextrin
SDD=spray-dried dispersion
sec-Bu-NH₂=sec-butyl amine
TEMPO=(2,2,6,6-Tetramethylpiperidin-1-yl)oxyl
TFA=trifluoroacetic acid
TFAA=trifluoroacetic anhydride
THF=tetrahydrofuran
vitamin E TPGS=D-α-tocopheryl polyethylene glycol 1000 succinate
Vol. or vol.=volume or volumes
XRPD=X-ray powder diffraction In some instances, Compound A is synthesized as outlined in Schemes A-D.

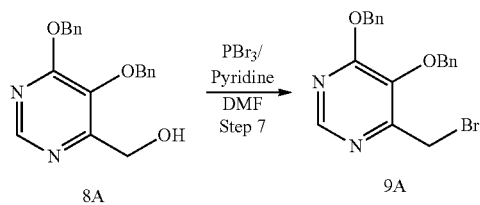

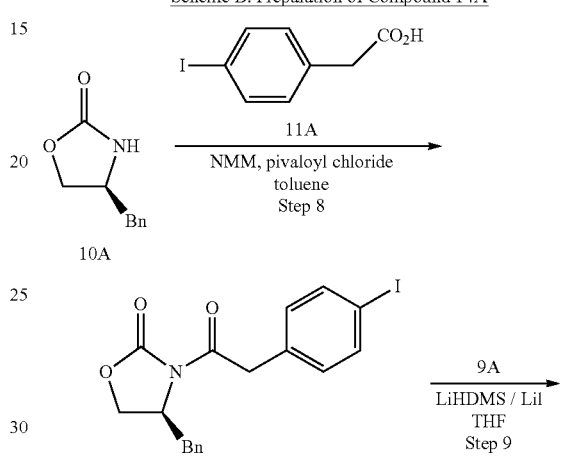

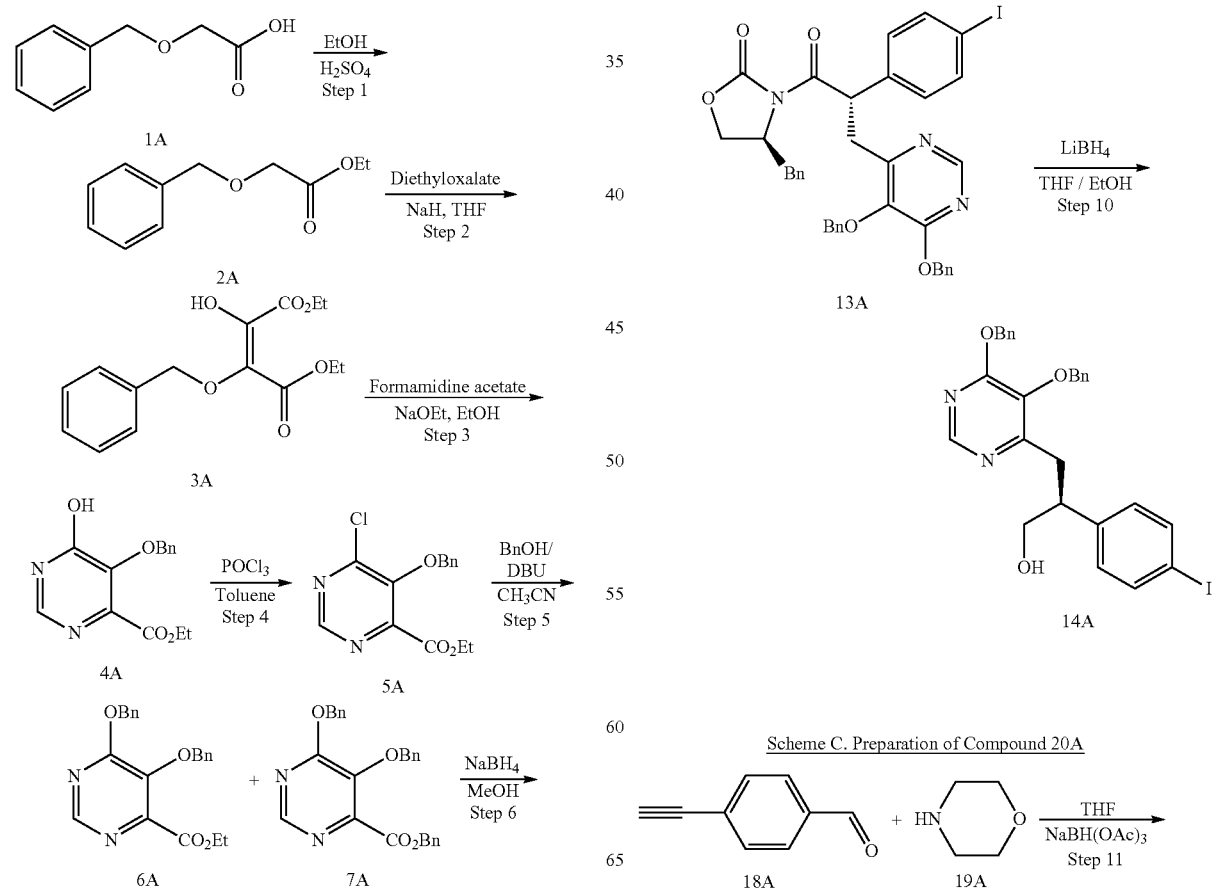

59
-continued

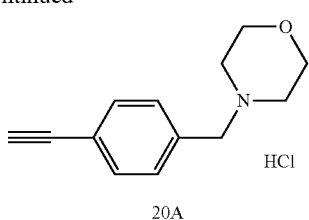

Scheme D. Preparation of Compound A

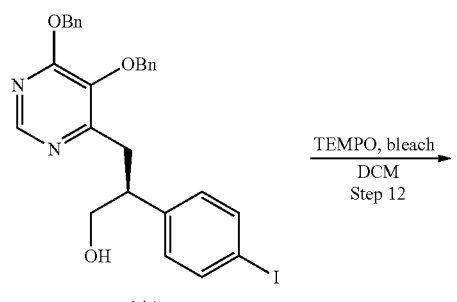

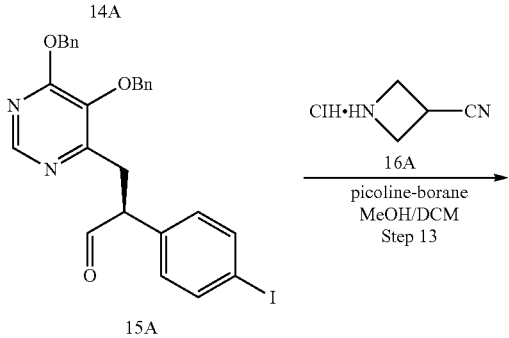

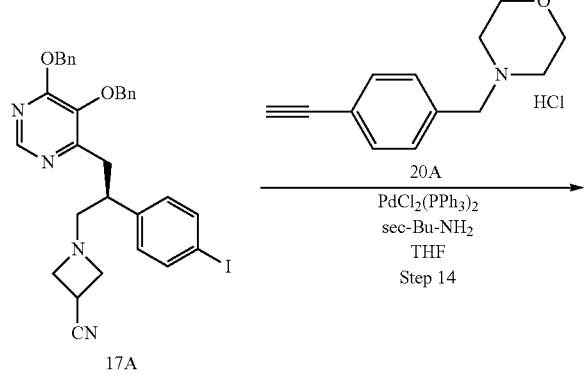

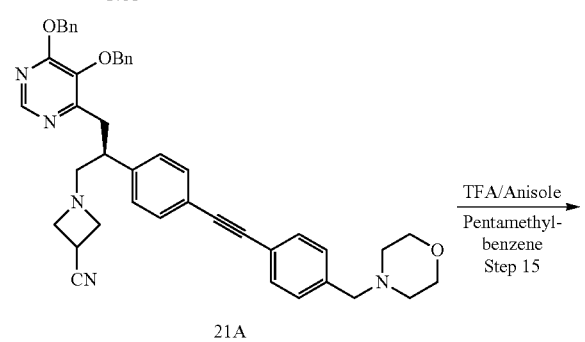

60
-continued

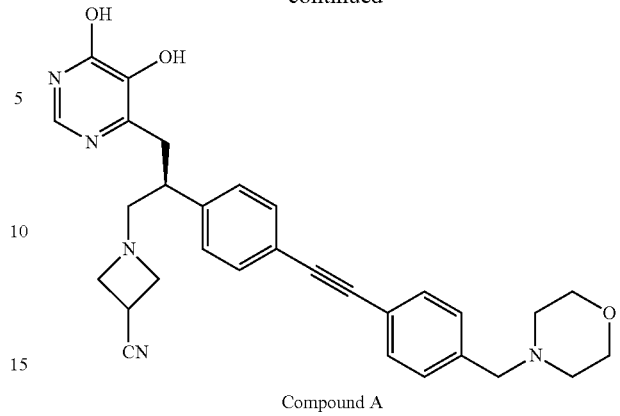

Compound A

Example 1: Preparation of (S)-1-(3-(5,6-dihydroxy-pyrimidin-4-yl)-2-(4-((4-(morpholinomethyl)phenyl)ethynyl)phenyl)propyl)azetidine-3-carbonitrile (Compound A)

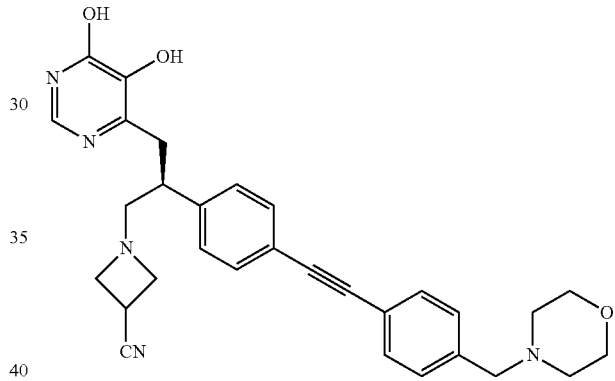

Example 1-1: Preparation of Ethyl 2-(benzyloxy)acetate (2A)

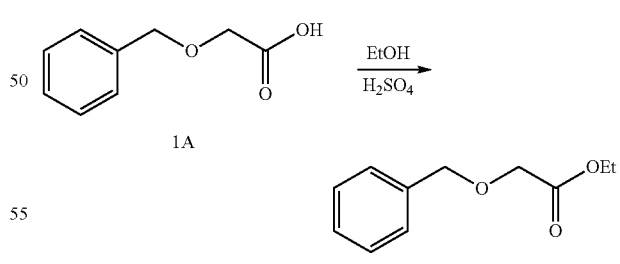

To a 3-L, three-necked round-bottom flask was charged 2-(benzyloxy)acetic acid (1A, 497.6 g, 3.00 mol, 1.0 eq.), followed by EtOH (1.65 mL, 3.3 vol.) at ambient temperature. To the stirred reaction mixture was added concentrated sulfuric acid (4.20 mL) dropwise over 2 min. After addition the mixture was heated to reflux for 23 h. After cooling to 40-50° C. the mixture was concentrated under vacuum. The resulting light yellow liquid was diluted with EtOAc (1.50

L, 3.0 vol.), and washed with saturated aqueous $K_2HPO_4$ (250 mL×2) and brine (250 mL). The organic phase was concentrated under vacuum to provide compound 2A as light yellow liquid (555.5 g, 95.5% yield). $^1H$ NMR is consistent with the structure.

Example 1-2: Preparation of Ethyl 5-(benzyloxy)-6-hydroxypyrimidine-4-carboxylate (4A)

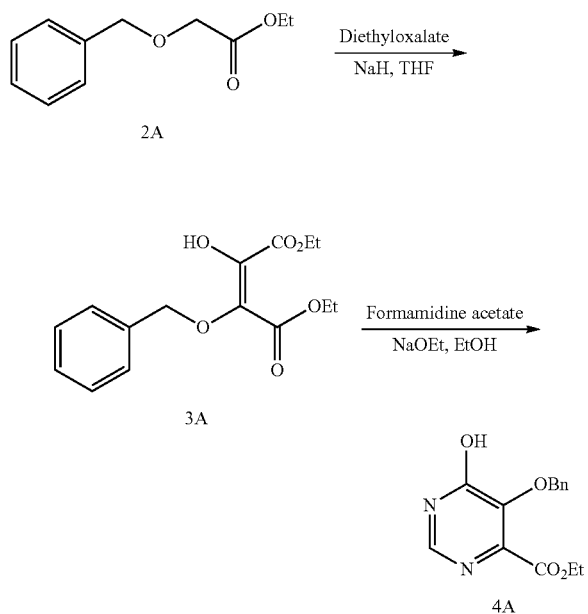

A 1-L, three-necked round-bottom flask was charged with NaH (43.7 g, 60% in mineral oil, 1.09 mol, 1.50 eq.), and then the flask was cooled in an ice-water bath and THF (566 mL, 4.0 vol.) was added. After the suspension was cooled to 0-10° C., 2A (141.5 g, 0.728 mol, 1.0 eq.) was added dropwise over 5 min. The addition funnel was washed with THF (71 mL) and the rinse was added to the batch over 5 min. Then to the batch was added diethyl oxalate (143.7 g, 0.983 mol, 1.35 eq.) dropwise over 5 min. After addition the suspension was slowly warmed to room temperature over 1 h and then stirred over 4 days at room temperature. The resulting mixture containing 3A was light brown clear solution.

The reaction mixture was then cooled to 0-10° C. and formamidine acetate solid (189.6 g, 1.82 mol, 2.5 eq.) was added portion wise over 5 min, followed by the addition of 21% NaOEt solution in EtOH (354 g, 1.09 mol, 1.5 eq.) over 5 min, and the reaction mixture was warmed to room temperature over 3 h. After stirring overnight at room temperature the reaction mixture was cooled to 0-10° C., then poured into a container with pre-cooled 2N HCl (1700 mL, 0-10° C.) and DI-water (420 mL) at 0-10° C. over 20 min. The resulting mixture was stirred for another 1 h and then filtered. The cake was washed with DI water (420 mL×2), followed by heptanes (420 mL×2), and then dried at 40-50° C. under high vacuum to provide 4A as a light yellow solid (44% yield over two steps). $^1H$ NMR is consistent with the structure.

Example 1-3: Preparation of Ethyl 5-(benzyloxy)-6-hydroxypyrimidine-4-carboxylate (5A)

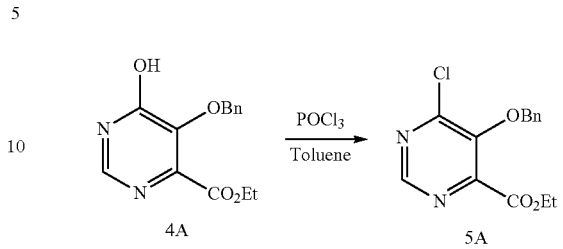

A suspension of 4A (106.0 g, 386.5 mmol, 1.0 eq.) in toluene (954 mL, 9.0 vol.) was cooled to 0-10° C. by ice-water bath. To the cooled reaction mixture was added $Et_3N$ (43.0 g, 425.1 mmol, 1.1 eq.), followed by addition of $POCl_3$ (252.2 mL, 27.1 mol, 7.0 eq.) dropwise over 40 min while maintaining the temperature at 0-10° C. After the addition was complete the reaction mixture was heated to 85-95° C. and then kept at this temperature for 1.5 h. The resulting dark solution was concentrated under vacuum. The resulting dark liquid was diluted with EtOAc (2.0 L) and cooled to 0-10° C. and the pH of the solution was adjusted to >7 by the addition of saturated aqueous $NaHCO_3$ (300 mL). After warming to room temperature, the organic phase was separated, and filtered through a short pad of $Na_2SO_4$ (106 g). The solid cake was washed with EtOAc (200 mL) and filtered. The combined filtrate was concentrated to provide 5A as light dark liquid (111.4 g, 98% yield). HPLC purity: 94.0% (AUC) at 254 nm. $^1H$ NMR is consistent with the structure. This product was used for next reaction without further purification.

Example 1-4: Preparation of Ethyl 5,6-bis(benzyloxy)pyrimidine-4-carboxylate (6A) & benzyl 5,6-bis(benzyloxy)pyrimidine-4-carboxylate (7A)

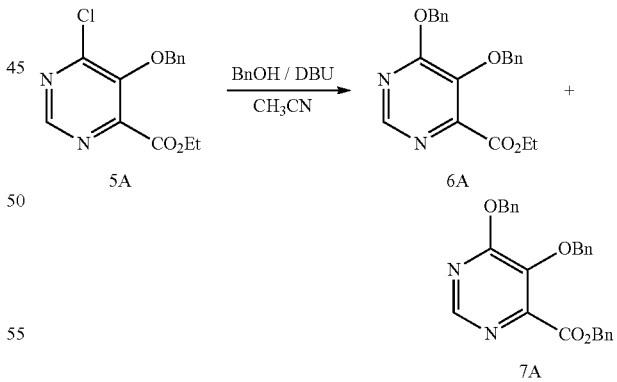

To a solution of 5A (117.6 g, 3865 mmol, 1.0 eq.) in acetonitrile (941 mL, 8.0 vol.) at room temperature was added DBU (134.6 g, 2.20 eq), followed by benzyl alcohol (86.9 g, 2.0 eq) dropwise over 20 min. A mild exothermic was observed during benzyl alcohol addition. After the addition, the clear solution was stirred overnight at room temperature and then concentrated under vacuum. The resulting residue was diluted with EtOAc (1.76 L, 15 vol), washed with water (706 mL, 6.0 vol), 1 N HCl (470 mL, 4.0 vol), and 20% brine (470 mL, 4.0 vol). The organic phase was separated and concentrated to provide a mixture of 6A & 7A as a dark solution (176.1 g, >99%). ¹H NMR is consistent with the presence of both structures. This product was used for next reaction without further purification.

Example 1-5: Preparation of (5,6-bis(benzyloxy)pyrimidin-4-yl)methanol (8A)

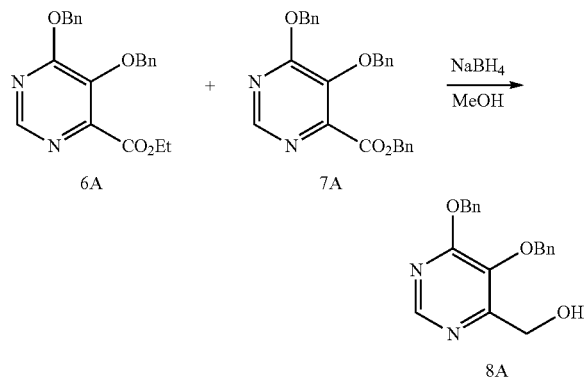

The mixture of 6A & 7A (140.0 g, 384 mmol, 1.0 eq.) is dissolved in a mixed solvent of IPA/MeOH (3/1, 840 mL/280 mL, 8.0 vol.). The reaction mixture was cooled to 0-10° C. and NaBH₄ (9.69 g, 256 mmol, 0.67 equiv.) was added in one portion. The mixture was stirred for 1 h. Then additional NaBH₄ (4.85 g, 0.34 eq) was added every 1 h. After total 2.0 eq. of NaBH₄ (29.07 g, 768 mmol) was added, the reaction was complete. The batch was cooled back to 0-10° C., saturated aqueous solution of NH₄Cl (164.4 g, 3.07 mol) in water (1680 mL) over 1.5 h. The mixture was warmed to room temperature and stirred overnight. After that the slurry was filtered; the resulting solid cake was slurry-washed with water (420 mL×2) to provide first crop of 8A as a white solid. The combined filtrated was stirred for 1 h and then filtered to provide second crop of 8A as a yellow solid. The total yield was 66%. ¹H NMR is consistent with the structure.

Example 1-6: Preparation of 4,5-bis(benzyloxy)-6-(bromomethyl)pyrimidine (9A)

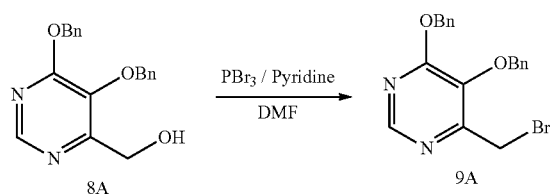

To a stirred solution of 8A (1000 g) in DMF (5.0 vol) cooled to 10° C. using ice bath, was added pyridine (1.2 eq) over a period of 10 minutes. To this PBr₃ (0.80 eq) was added slowly over a period of 30 minutes. The reaction mixture was stirred at 0° C. over a period of 1 hr and then quenched with water (8 vol) in an ice bath. The reaction mixture was extracted with dichloromethane (4.0 vol) and the organic layer was dried over Na₂SO₄ and then filtered.

The organic layer was concentrated, then the resulting residue was slurried in heptanes and filtered to give a 9A (1.5 kg) as a white solid. ¹H NMR is consistent with the structure.

Example 1-7: Preparation of (S)-4-benzyl-3-(2-(4-iodophenyl)acetyl)oxazolidin-2-one (12A)

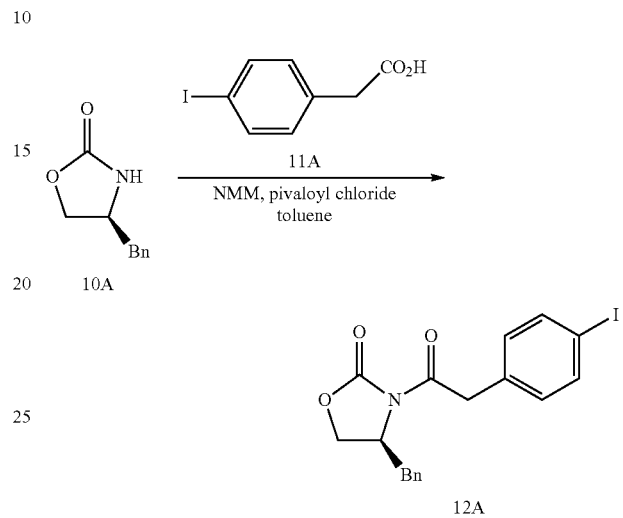

To a cloudy solution of (S)-benzyl-2-oxazolidinone (10A, 290.1 g, 1.3 eq) and NMM (1.65 L, 1.3 eq) in toluene (1.65 L, 5 vol) was added pivaloyl chloride (169.6 mL, 1.1 eq) at 19.5-20.2° C. over 9 min. The cloudy solution was heated to 80° C. and a solution of 4-iodophenylacetic acid (11A, 330.0 g, 1.0 eq) and NMM (235.4 mL, 1.7 eq) in toluene (660 mL, 2 vol) was added over 135 min. The mixture was then heated at 107-112° C. for 5 h. The mixture was cooled to 90-95° C., and another portion of pivaloyl chloride (66.0 mL, 0.43 eq) was added and the mixture was heated at 107-112° C. for another 14 h. The mixture was cooled to 90-95° C., and another portion of pivaloyl chloride (46.2 mL, 0.30 eq) was added and the mixture was heated at 107-112° C. for another 7 h. The mixture was cooled to 90-95° C., and another portion of pivaloyl chloride (18.5 mL, 0.12 eq) was added and the mixture was heated at 107-112° C. for another 17 h, and at this point the reaction was deemed to be complete. The reaction was cooled to <35° C. and 7% NaHCO₃ in H₂O (1.32 L) was added (endothermic). After being stirred for 20 min, two layers were separated. The organic phase was washed with 7% NaHCO₃ in H₂O (1.32 L), H₂O (1.32 L), and 13% NaCl in H₂O (1.32 L). The organic layer (2810 mL) was concentrated to 2.5 vol (~824 mL) containing toluene (~330 mL, 1 vol). The solution was held at rt overnight and some crude product precipitated. The mixture was heated at 35-40° C. to dissolve most solids. IPA (1980 mL, 6 vol) was added over 30 min. The resulting slurry was stirred at 35-40° C. for 2 h, and IPA (1980 mL, 6 vol) was added over 20 min at 35-40° C. The slurry was stirred at 35-40° C. for 3 h and at rt for 44 h. The slurry was then gradually cooled to 0-5° C. and stirred for 3 h. The solids were filtered, washed with IPA (660 mL×2), dried under high vacuum at 45° C. to provide 12A (405.2 g, 76% yield, 98.5% (AUC)) as an off-white solid. ¹H NMR is consistent with the structure.

Example 1-8: Preparation of (S)-4-benzyl-3-((S)-3-(5,6-bis(benzyloxy)pyrimidin-4-yl)-2-(4-iodophenyl)propanoyl)oxazolidin-2-one (13A)

Example 1-9: Preparation of (S)-3-(5,6-bis(benzyloxy)pyrimidin-4-yl)-2-(4-iodophenyl)propan-1-ol (14A)

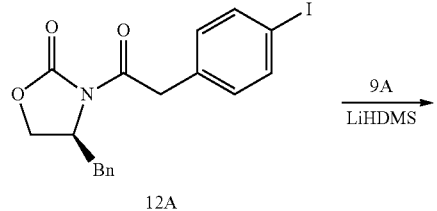

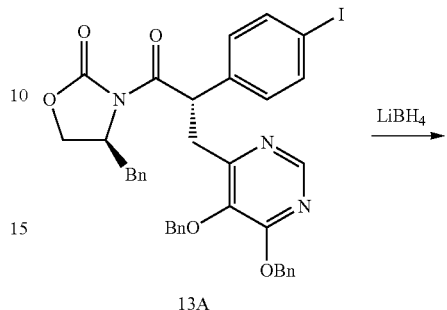

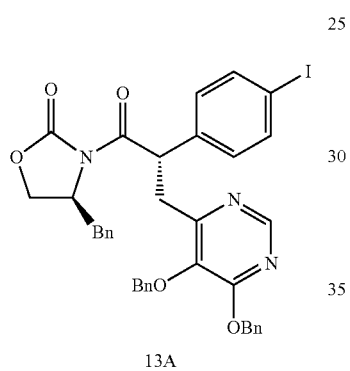

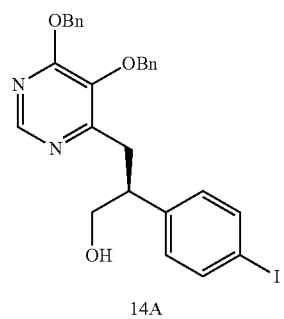

To a solution of 12A (344.4 g) and LiI (10.4 g 0.1 eq) in THF (1200 mL, 4 vol) was added 1.0 M LiHMDS solution in THF (934.4 mL, 1.2 eq) at −24.8° C. to −18.8° C. over 35 min. After 15 min, 9A (300.0 g, 1.0 eq) in THF (375 mL, 1.25 vol) was added at −24.1° C. to −19.6° C. over 23 min. The flask and addition funnel were rinsed with THF (75 mL, 0.25 vol). After the addition was complete, the resulting solution was stirred at −22.8° C. to −17.3° C. for 4 h, at this point the reaction was deemed to be complete by HPLC analysis. The reaction was quenched with 15% NH$_4$Cl solution in H$_2$O (900 mL) over 10 min at <20° C. The mixture was warmed to 10.5° C., and MTBE (900 mL, 3 vol) was added. The two phases were separated. The organic layer was washed with 1 M HCl (900 mL, 3 vol), H$_2$O (900 mL×3). The organic layer was concentrated under vacuum at 40-50° C. to 3 vol (900 mL) and was azeotroped with EtOAc. EtOAc (1200 mL, 4 vol) was added and the mixture was concentrated to 3 vol (900 mL) three times. To the concentrated residue was added heptanes dropwise (1800 mL, 6.0 vol mL) at 60° C. After the addition was complete, the solution was stirred at 60° C. for 2 h and then the resulting slurry was cooled to 10° C. over 4 h and stirred at 10° C. for 8 h, filtered, washed with EtOAc/heptanes (1:3, 600 mL×2), and dried under high vacuum at 30-40° C. for 24 h to provide 13A (399.1 g, 70.6%, 99.1% AUC, 99.5% de) as a light yellow solid. $^1$H NMR is consistent with the structure.

To a solution 13A (300.0 g, 413.35 mmol) in THF (750.0 mL, 2.5 vol) and EtOH (1350 mL, 4.5 vol) was added 2 M LiBH$_4$ in THF (206.67 mL, 1.0 equiv) dropwise over 35 min at 20 f 5° C. (T: 17.3-23.0° C.). (The mixture turned to a thick slurry when 80 mL of LiBH$_4$ was added and turned to a solution again after the completion of the addition.) After the addition was complete, the solution was stirred at 20±5° C. (T: 18.8-22.4° C.) for 5 h (97.3% conversion, e.r: 99.3: 0.7). 15% NH$_4$Cl solution in H$_2$O (900 mL, 3 vol) was added dropwise over 15 min at 15-30° C. MTBE (1200 mL, 4 vol) was added follows by 26% NaCl (300 mL, 1 vol). Two phases were separated, and the organic was washed with 13% NaCl solution in H$_2$O (900 mL×4). The organics (2.45 L, 1H NMR, THF, 28.2%; EtOH, 24.5%; MTBE, 47.3% v/v) was concentrated to 780 mL (2.6 vol). IPA (1200 mL, 4 vol) was added and the solution was concentrated to 780 mL (2.6 vol) again. IPA (1200 mL, 4 vol) was added and the solution was concentrated to 780 mL (2.6 vol). IPA (1200 mL, 4 vol) was added and the solution was concentrated to 960 mL (3.2 vol) ($^1$H NMR, IPA: 96.8%, EtOH: 3.2% v/v). H$_2$O (375 mL, 1.25 vol) was added at 50° C. The batch turned to a suspension after the addition of H$_2$O. The precipitation was started after 20 min and turned to a thick slurry. The slurry was stirred at 50° C. for 5 h, then cooled to 5° C. over 4 h, and stirred at 5° C. for 12 h (conc. 8.10 mg/mL), filtered, washed with IPA/H$_2$O (2:1, 300 mL×2), dried under high vacuum at 35-40° C. for 24 h to afford 14A (202.6 g, 88.7%, 98.4% AUC, 99.9% ee) as an off-white solid.

Example 1-10: Preparation of (S)-3-(5,6-bis(benzyloxy)pyrimidin-4-yl)-2-(4-iodophenyl)propanal (15A)

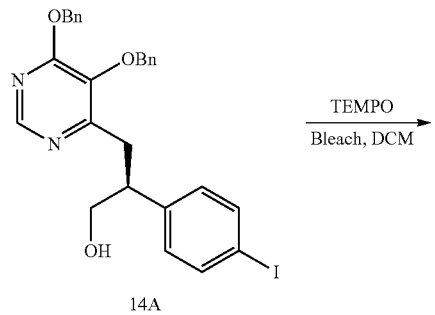

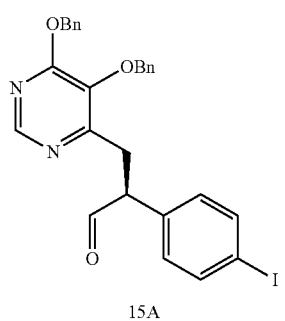

To a solution of 14A (1.5 kg, 2.72 mol, 1.0 equiv) in DCM (12 L, 8 vol, Fisher Chemicals lot #198170) in a 30-L reactor were added TEMPO (4.2 g, 0.027 mol, 0.01 equiv, KBr (32.3 g, 0.27 mol, 0.1 equiv), and water (2.25 L, 1.5 vol). The mixture was cooled to 5 f 5° C., and 10% sodium hypochlorite (2.3 L, 5.43 mol, 1.1 equiv, pH was adjusted to 9-9.3 with 0.59 L of 8% NaHCO₃ solution) was charged to the mixture slowly over a period of 1 h while keeping the temperature at 55° C. After the addition was complete, the biphasic mixture was stirred at 5±5° C. for additional 10 min. The reaction was monitored by HPLC for completion (spec: <4% 14A). Upon completion, the batch was quenched by the slow addition of 12% Na₂S₂O₃ solution (3 L, 2 vol) over 30 min keeping the batch temperature 5±5° C. (end point: negative KF-starch paper test). MeOH (3.0 L, 2 vol) was charged to the batch over 1 h with mixing and let the layers separate. The cloudy organic layer containing crude 15A was separated and directly used in stage 2, reductive amination. Analysis of 15A: Chemical purity: 93.6% AUC by HPLC.

Example 1-11: Preparation of (S)-1. (3-(5,6-bis(benzyloxy)pyrimidin-4-yl)-2-(4-iodophenyl)propyl) azetidine-3-carbonitrile (17A)

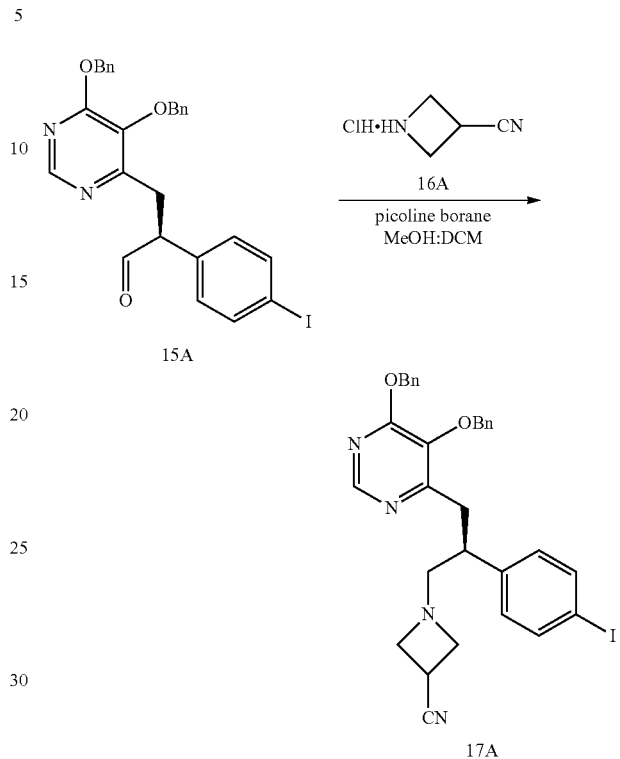

Azetidine-3-carbonitrile (16A) (032 kg, 2.73 mol, 1.0 equiv) was charged into the reactor under nitrogen atmosphere. To this the cloudy organic phase containing 15A (1.5 kg, 2.72 mol, 1.0 equiv) in DCM (≈12 L) and MeOH (3 L, 2 vol) was charged followed by the addition of additional MeOH (7.5 L, 6 vol) to form a clear yellow solution. At this point, the batch was analyzed by ¹H NMR for the DCM to MeOH ratio (53.7:46.3) and KF (3.98%) for the water content. The batch was cooled to 10±5° C. and was added a solution of 2-methyl-pyridine borane complex (0.29 kg, 2.73 mol, 1.0 equiv) in THF (0.75 L, 0.5 vol) over 1 h maintaining the batch temperature 10±5° C. Upon complete charge of borane complex, the batch was agitated for additional 10 min at 10±5° C., warmed to 20±5° C. over 1 h, and agitated at the temperature until completion (12 h) confirmed by HPLC (spec:>98%). After completion of reaction, 5% NaHCO₃ (4.5 L, 3 vol,) was added over 30 min and agitated for additional 1 h at 10±5° C. Two phases were separated and the aqueous phase was removed. The combined organic phase was washed with 10% aqueous citric acid (3 vol×2, 9 L), 8% NaHCO₃ (4.5 L, 3 vol), and 13% aqueous brine (4.5 L, 3 vol). The organic phase containing 17A was concentrated to 3 L (2 vol) under reduced pressure. Then the batch was subjected to solvent swap by MTBE (3 vol×2, 15 L) to achieve the final concentration of DCM to <5 vol % by ¹H NMR (2.5 vol %). The batch volume was adjusted by MTBE (16.5 L, 11 vol) and agitated at 20±5° C. for at least 5 h. The insoluble solid separated was removed by filtration and the filtrate was adjusted to 15 vol by the addition of MTBE (6 L, 4 vol). The batch was cooled to 5±5° C. and 3 M HCl solution in CPME (2.27 L, 2.5 equiv) was added over 1 h by maintaining the batch at 5±5° C. The slurry was stirred at 5±5° C. for at least 1 h and filtered. 17A-HCl was washed with MTBE (2 vol×2, 6 L) and conditioned for additional 4-5 h under inert atmosphere to remove most of MTBE. The filter cake was analyzed for both chemical and chiral purity by HPLC. The wet 17A was charged back to the reactor and charged DCM (6 L, 4 vol) to form suspension. To this 8% NaHCO₃ (6 L, 4 vol) was charged and agitated for 30 min at 20±5° C., and let the layers separate. The aqueous phase was removed, and the organic layer was washed with brine (3 L, 2 vol). The organic phase was concentrated to dryness to yield 17A as a yellow oil that was dried for at least 72 h under high vacuum and stored at 2-8° C. until used in stage 3. Analysis of crude 17A: Chemical purity: 78.8% (AUC) by HPLC, 96.5% (AUC) by chiral HPLC nm; net weight: 1.54 kg; potency by qNMR: 65.1 wt %; adjusted weight: 1.15 kg (67%); DCM by NMR content: 2.22 wt %.

Example 1-12: Preparation of 4-(4-ethynylbenzyl)morpholine Hydrochloride (20A)

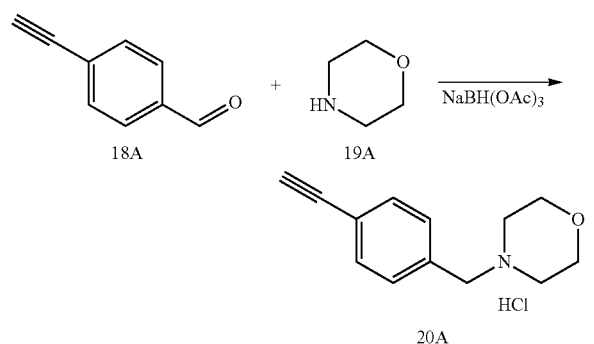

To a solution of ISA (600 g) in THF (1.2 L) was added a solution of morpholine (19A) (0.484 L, 1.2 equiv) in THF (0.60 L) over 79 min at 5±5° C. (T: 1.4° C.→7.1° C.). The solution was added at 15±5° C. (T: 11.5° C.→19.6° C.) to a slurry of NaBH(OAc)₃ (STAB, 1.173 kg, 1.2 equiv) in THF (4.2 L) over 2 h 43 min. After the addition was complete, the reaction mixture was stirred at 20±5° C. for 14 h and IPC showed 94.7% conversion. Additional morpholine (0.12 equiv) and STAB (0.12 equiv) were charged and batch was stirred for 2 h. IPC showed 100% conversion. 8% NaHCO₃ solution (90 mL, 3 vol) was added over 18 min to quench the reaction (T: 20.7° C.→21.8° C.). The mixture was stirred for 49 min. Two phases were separated. The aqueous was extracted with MTBE (2.40 L, 4 vol). The combined organics was washed with 5% NaHCO₃ solution (1.80 L, 3 vol), 2 M HCl (2.40 L×1, 1.20 L×1). The combined acidic aqueous was basified with 50% NaOH to pH=11.0±0.5 (pH=11.0), extracted with MTBE (2.40 L×2). The organics was washed with basic brine (1.80 L, pH=11.0), dried (sodium sulfate, 0.60 kg), and filtered. Filter cake was washed with MTBE (0.30 L×2). The combined filtrate was concentrated to 1.80 L. MTBE (2.40 L) was added. The solution was concentrated to 1.80 L and MTBE (2.40 L) was added again. The solution was concentrated to 1.80 L, at this point MTBF/THF (97.4:2.6, v/v). Batch was in-line filtered into the reactor and MTBE (3.00 L) was used to rinse the container holding the batch. To this solution was added 3 M HCl in CPME solution (3.074 L, 2.0 equiv) over 1 h 55 min at 5±5° C. The resulting slurry was stirred at 5±5° C. for 2 h (conc. 0.12 mg/mL in mother liquor). The slurry was filtered, washed with MTBE (1.80 L×2), and dried to give 20A-HCl (1.038 kg, 95% yield, 97.9% (AUC) by HPLC) as a light yellow solid.

Example 1-13: Preparation of (S)-1-(3-(5,6-bis(benzyloxy)pyrimidin-4-yl)-2-(4-((4-(morpholinomethyl)phenyl)ethynyl)phenyl)propyl)azetidine-3-carbonitrile (21A

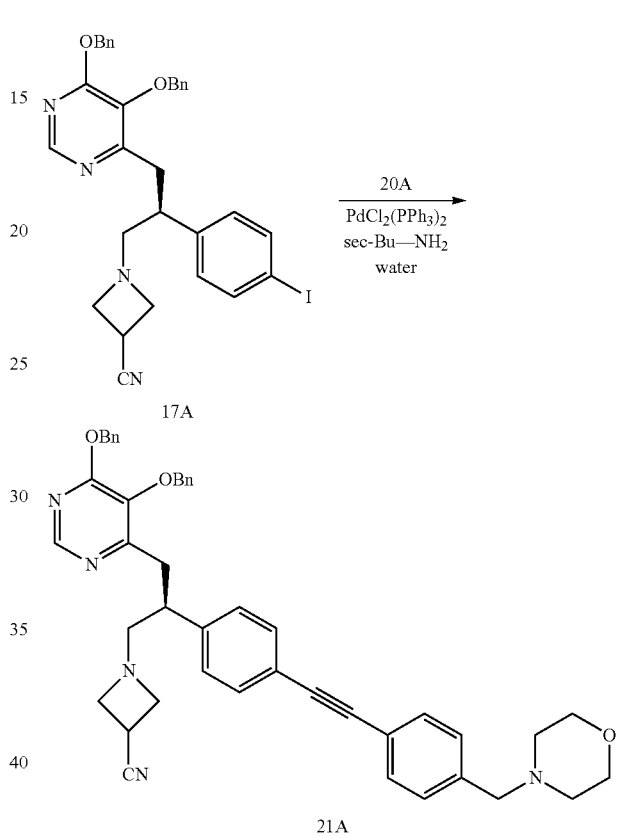

20A (0.87 kg, 3.66 mol, 1.05 equiv) was charged into a 30-L reactor under nitrogen atmosphere. To this, a solution of 17A (2.15 kg, 3.49 mol, 1.0 equiv) in sec-BuNH₂ (7.53 L, 3.5 vol) was added with stirring at 20±5° C. The container was rinsed with sec-BuNH₂ (1.075 L, 0.5 vol) and charged the rinses to the batch. No significant exotherm was observed. The reaction mixture was cooled to 10±5° C. and water (8.6 mL, 4 vol) was charged slowly to the reaction mixture over 1 h maintaining the batch temperature at 20±5° C. Then nitrogen was bubbled through the reaction mixture for at least 30 min. Pd(Ph₃P)₂Cl₂ (49 g, 0.07 mol, 0.02 equiv) was added as a slurry in sec-BuNH₂ (0.11 L, 0.05 vol) while sparging nitrogen through the reaction mixture. The container was rinsed with sec-BuNH₂ (0.11 L, 0.05 vol) and charged to the batch. The batch was gradually heated to 45±5° C. over at least 1 h. The reaction mixture was stirred at 5° C. under nitrogen atmosphere for 12 h. After 12 h, at this point the reaction was deemed to be complete by HPLC (>98%). The reaction mixture was diluted with IPAc (10.75 L, 5 vol) by quick addition and stirred for 30 min. Then 5% aqueous citric acid solution (10.75 L, 5 vol) was charged over 30 min by maintaining the batch temperature at 20±5° C. and stirred for at least 30 min before letting the layers separate. Aqueous phase (bottom phase) was removed and the organic phase was washed with 5% citric acid solution (5 vol×2, 21.5 L). The organic layer was then successively washed with 5% ammonium pyrrolidinedithiocarbamate (2.3 vol×2, 5 L), DI water (5 vol×1, 10.75 L), and 13% brine solution (5 vol×1, 10.75 L). The organic phase was separated and filtered through a pad of Celite (≈1.5 inches) to remove insoluble palladium salts. The reactor used was cleaned and inerted under nitrogen for 30 min, and charged SiliaMet-Thiol resin (0.65 kg, 30 wt %, Silicycle lot #165304) under nitrogen atmosphere. The organic phase containing 21A in IPAc was then charged with stirring and the slurry was stirred for 16 h at 20±5° C. The slurry was filtered through a pad of Celite (≈1.5 inches). SiliaMetThiol resin (0.65 kg, 30 wt %, Silicycle lot #162798) was charged into the reactor followed by the filtrate for the 2nd Pd remediation of 21A. The slurry was filtered through a pad of Celite (≈1.5 inches) and the filtrate was concentrated under reduced pressure. The residue was further dried under high vacuum until the IPAc content of the batch was less than 10 wt % by $^1$H NMR (72 h) to afford crude 21A (2.26 kg) as a dark brown gummy oil that was used in stage 4 without further purification. The batch was split into two portions for effective drying under high vacuum and the analysis of both portions is given below. 21A Crude weight: 2.26 kg; Crude purity: 73.5% (AUC) by HPLC; 97.5% (AUC) by chiral HPLC; potency by qNMR: 69.4 wt %; Adjusted weight 1.57 kg (65%); IPAc content: 7 wt %; Pd content: 428 ppm.

Example 1-14: Preparation of (S)-1-(3-(5,6-dihydroxypyrimidin-4-yl)-2-(4-((4-(morpholinomethyl)phenyl)ethynyl)phenyl)propyl)azetidine-3-carbonitriles (Compound A)

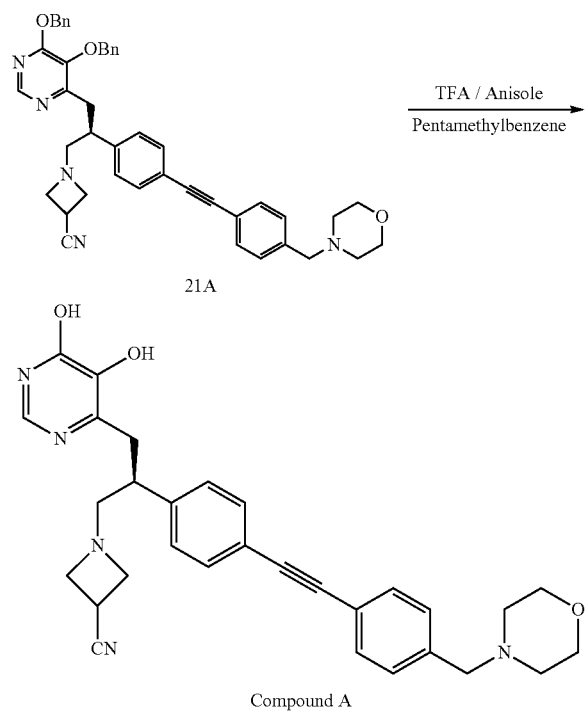

A solution of 21A (1.560 kg, 2.26 mol, 1 equiv) in anisole (1.560 L, 1 vol,) was added to a mixture of pentamethylbenzene (3.352 kg, 22.6 mol, 10.0 equiv) and TFA (9.750 L, 6.25 vol) at 30±5° C. over a period of 2 h. The containers holding 21A were rinsed with anisole (0.195 L×2, 0.125 vol×2) and the rinses were added to the reaction mixture at 30±5° C. Batch was stirred at 30° C. for 29 h, at which time HPLC analysis showed 95.4% conversion. Batch was then stirred at 20±5° C. for 10.5 h, at which time HPLC analysis showed 97.1% conversion. With stirring, batch was added to MTBE (19.5 L, 12.5 vol) over a period of 1.75 h while keeping the temperature below 15° C. The resulting suspension was stirred at 20±5° C. for 3 h and the supernatant was removed using a pump. The precipitate was rinsed with MTBE (4.7 L×2, 3 vol×2) and the rinses were removed using a pump. The precipitate was dissolved in acetonitrile (4.68 L, 3 vol) and the pH was adjusted to pH 7.28 (measured by a pH meter) using 10.1 L of 8% sodium bicarbonate solution and 6.0 L of 2 M sodium hydroxide solution. The resulting suspension was stirred at 20±5° C. for 24.5 h and filtered. The reactor was rinsed with deionized water (4.68 L×2, 3 vol×2) and the rinses were transferred to the filter funnel. The filter cake was conditioned under nitrogen for 5.5 h to provide a brownish yellow solid (2.762 kg, 26.12 wt % by quantitative NMR). The filter cake was dissolved in acetic acid (2.88 L, 4 vol, at 45±5° C. THF (25.0 L, 34.6 vol) was charged at ±45 5° C. over a period of 5 h 11 min. The resulting suspension was cooled to 20±5° C. over a period of 3 h, stirred at 20±5° C. for 18 h, and filtered. The reactor was rinsed with 12:1 THF/water (1.44 L, 2 vol) and the rinse was transferred to the filter funnel. The filter cake was washed with THF (0.72 L×2, 2 vol×2) and dried under vacuum at 45±5° C. for 39.5 h, at which time it reached constant weight (0.758 kg). This material was suspended in water (11.4 L, 15 vol) and treated with 1 M HCl (3.415 L) at 45° C. until a solution was formed at pH=2. Then 1 M NaOH solution (3.40 L) was charged slowly to endpoint of pH 7, at which time batch became a slurry. After cooling to 20±5° C., the batch was filtered. The reactor was rinsed with water (2.3 L×2, 3 vol×2) and the rinses were transferred to the filter funnel. The filter cake was dried under vacuum at 45±5° C. for 75 h to provide Compound A [0.745 kg, 65%, 97.5% AUC] as an off-white to light beige solid.

Example 2: Alternative Preparation of Compound 8A

In some instances, Compound 8A is synthesized as outlined in Scheme E.

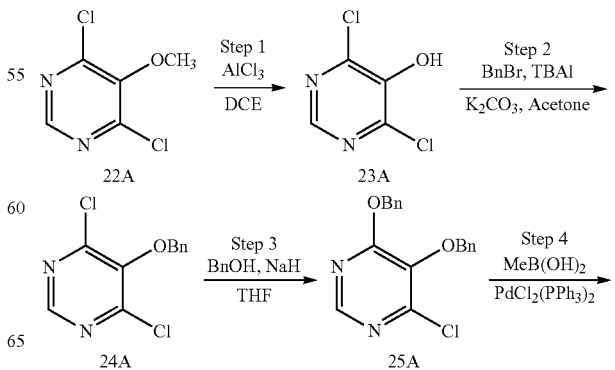

Scheme E. Alternative Preparation of Compound 8A

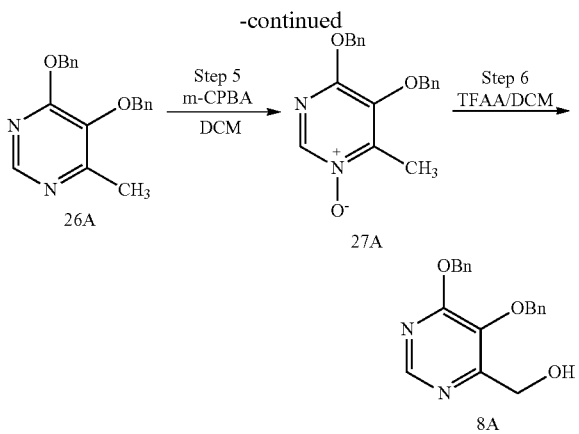

Example 2-1: Preparation of 4,6-dichloropyrimidin-5-ol (23A)

To a stirred cooled (0° C.) solution of 4,6-dichloro-5-methoxypyrimidine (50.0 g, 0.279 mol) in dichloroethane (500 mL), AlCl$_3$ (37.2 g, 1.0 eq) was added portionwise over a period of 20 minutes. The reaction mixture was heated to 50° C. and stirred at that temperature for 2 hr. LCMS indicated the disappearance of starting material. The reaction mixture was cooled to 0° C. and then quenched with ice cold water (200 mL). The compound was extracted with dichloromethane. The aqueous layer was further basified using NaHCO$_3$ and further extracted with dichloromethane. The organic layers were combined and washed with satd. NaCl and further dried (Na$_2$SO$_4$) and concentrated. The crude mixture was further purified on a silica gel column using hexanes in ethyl acetate to afford the product (23.0 g, 50%).

Example 2-2: Preparation of 5-(benzyloxy)-4,6-dichloropyrimidine (24A)

To a stirred solution of 4,6-dichloropyrimidin-5-ol (23A, 22 g, 0.133 mol) in acetone (150 mL), K$_2$CO$_3$ (46.07 g, 2.5 eq, 0.33 mol) was added followed by the addition of TBAI (5 mol %). The reaction mixture was stirred at room temperature for a period of 20 minutes, followed by the addition of benzyl bromide (17.4 mL, 0.146 mol, 1.1 eq) and continued stirring over a period of 2 hr. LCMS indicated complete conversion. The reaction mixture was concentrated and then quenched over water (100 mL). The compound was extracted with ethyl acetate (2×125 mL). The organic layers were combined and washed with saturated NaCl, dried (Na$_2$SO$_4$) and concentrated to dryness. The crude obtained is around 95% pure and yielded (34 g, 100%). No further purification was necessary, and it was taken to the step.

Example 2-3: Preparation of 4,5-bis(benzyloxy)-6-chloropyrimidine (25A)

To a solution of dried THF (25 mL), NaH (6.4 g, 1.2 eq) was added and cooled to 0° C. using an ice bath. To this BnOH (15.2 mL, 0.146 mol, 1.1 eq) dissolved in THF (20 mL) was added dropwise over a period of 30 minutes. The reaction mixture was continues stirring for 15 minutes. To this, 5-(benzyloxy)-4,6-dichloropyrimidine (24A, 34 g, 0.133 mol) dissolved in THF (50 mL) was added dropwise over a period of 10 minutes. The reaction mixture was stirred at room temperature for a period of 90 minutes. LCMS indicated completed conversion. The reaction mixture was quenched with satd. NH$_4$Cl and the compound was extracted with ethyl acetate (2×125 mL). The organic layers were combined and washed with satd. NaCl, dried (Na$_2$SO$_4$), concentrated to obtain a crude compound. The compound was purified using silica gel using hexanes in ethyl acetate to obtain Compound 25A as a colorless oil (34.0 g, 78% yield).

Example 2-4: Preparation of 4,5-bis(benzyloxy)-6-methylpyrimidine (26A)

To a stirred solution of 4,5-bis(benzyloxy)-6-chloropyrimidine (25A, 32 g 0.097 mol) in dioxane (100 mL), potassium acetate (14.4 g 0.146 mol, 1.5 eq), methyl boronic acid (7.63 g, 0.127 mol, 1.3 eq) was added along with PdCl$_2$(PPh$_3$)$_2$ (0.05 eq) and reaction mixture was heated to 100° C. over a period of 12 h. LCMS indicated completed conversion. The reaction mixture was diluted with water (75 mL) and extracted with EtOAc (2×75 mL). The organic layers were combined and washed with satd. NaCl, dried (Na$_2$SO$_4$) and concentrated to give the crude compound. The compound was purified using silica gel column to obtain Compound 26A a thick oil (24.8 g. 83%).

Example 2-5: Preparation of 4,5-bis(benzyloxy)-6-methylpyrimidine 1-oxide (27A)

To m-CPBA (77%, 4.2 g 18.6 mmol) was added slowly to a stirred solution of 4,5-bis(benzyloxy)-6-chloropyrimidine (95%, 2.0 g 6.2 mmol) in DCM (25 mL) at room temperature. The mixture was stirred at room temperature for 1 h then treated with solid K$_2$CO$_3$ (3.9 g, 6 eq). The resulting mixture was stirred for 10 min then the insolubles removed by filtration. The filter cake was washed with DCM (3×25 mL) and the filtrate concentrated in vacuo. Column chromatography (SiO$_2$ Biotage isolera, 10 g) eluting with 0 to 10% methanol in DCM afforded Compound 27A (2.2 g, 95%) as a clear oil which solidified on standing. HPLC-MS (ESI) [M+H]$^+$ m/z=323.25; $^1$H NMR (500 MHz, Chloroform-d) δ 8.60 (s, 1H), 7.53-7.27 (m, 10H), 5.50 (s, 2H), 5.12 (s, 2H), 2.36 (s, 3H).

Example 2-6: Preparation of (5,6-bis(benzyloxy)pyrimidin-4-yl)methanol (8A)

To trifluoroacetic anhydride (0.7 ml, 5.2 mmol) was added to a stirred solution of 4,5-bis(benzyloxy)-6-methylpyrimidine 1-oxide (500 mg, 1.3 mmol) in DCM (8 mL) at room temperature. The mixture was stirred overnight at room temperature then mixed with 2 M aqueous K$_2$CO$_3$ solution (20 mL). The resulting biphasic mixture was stirred for 5 min then extracted with EtOAc (2×25 mL). The combined organic phase was dried (Na$_2$SO$_4$) and concentrated in vacuo to leave a crude residue. Column chromatography (SiO$_2$ Biotage isolera, 10 g) eluting with 0 to 100% EtOAc in heptanes afforded Compound 8A (330 mg. 79%) as a clear glass which solidified on standing. HPLC-MS(ESI) [M+H]+ m/z=322.95; $^1$H NMR (500 MHz, Chloroform-d) δ 8.50 (s, 1H), 7.52-7.46 ((m, 2H), 7.43-7.34 ((m, 3H), 7.34-7.27 (m, 5H), 5.56 (s, 2H), 5.09 (s, 2H), 4.58 (s, 2H).

II. Biological Evaluation

Example 3: Bacterial Susceptibility Testing

Minimal inhibitory concentrations (MIC) against a variety of gram-negative and gram-positive bacterial strains were determined by the broth microdilution method in accordance with the Clinical and Laboratory Standards Institute (CLSI) guidelines. In brief, organism suspensions were adjusted to a 0.5 McFarland standard to yield a final inoculum between $3\times10^5$ and $7\times10^5$ colony-forming units (CFU)/mL. Drug dilutions and inocula were made in sterile, cation adjusted Mueller-Hinton Broth (Beckton Dickinson). An inoculum volume of 100 µL was added to wells containing 100 µL of broth with 2-fold serial dilutions of drug. All inoculated microdilution trays were incubated in ambient air at 35° C. for 18-24 h. Following incubation, the lowest concentration of the drug that prevented visible growth (OD600 nm<0.05) was recorded as the MIC. Performance of the assay was monitored by the use of laboratory quality-control strains and levofloxacin, a compound with a defined MIC spectrum, in accordance with CLSI guidelines.

Exemplary in vitro assay data against select bacteria for Compound A, Meropenem, and Levofloxacin is provided in Table 1.

TABLE 1

| Bacterium | Strain | MIC (µg/mL) Compound A | Meropenem | Levofloxacin |
|---|---|---|---|---|
| E. coli | ATCC 25922 | 0.5 | 0.03 | 0.03 |
| K. pneumoniae | ATCC 13883 | 0.5 | | |
| S. aureus | ATCC 29213 | >64 | 0.125 | 0.25 |
| E. faecalis | ATCC 29212 | >64 | >1 | 1 |
| S. pyogenes | ATCC 12384 | >64 | 0.008 | 0.5 |
| B. thuringiensis | ATCC 35646 | >64 | 0.06 | 0.125 |
| L. rhamnosus | ATCC 53103 | >64 | >1 | 1 |
| S. epidermidis | ATCC 35984 | >64 | >1 | 0.125 |
| B. breve | HM 412 | >64 | >1 | 4 |
| C. difficile | ATCC 700057 | >64 | 1 | 4 |
| C. sordellii | ATCC 9714 | >64 | 0.015 | 1 |
| P. anaerobius | DSM 20357 | >64 | >1 | 0.5 |
| S. pneumoniae | ATCC 49619 | >64 | 0.06 | 1 |
| C. jeikeium | NCTC 11914 | >64 | >1 | 1 |
| P. acnes | ATCC 6919 | >64 | 0.06 | 0.5 |
| L. monocytogenes | ATCC 7644 | >64 | 0.125 | 1 |
| N. cyriacigeorgica complex | NBQAS 3295 | >64 | >1 | 8 |

Compound A has high selectivity for gram-negative bacteria over gram-positive bacteria. Standard of care antibiotics Meropenem and Levofloxacin, in contrast, do have activity against various strains of gram-positive bacteria.

III. Pharmaceutical Compositions

Example 4: Intravenous (I.V.) Solution Formulation

Compound A is formulated as a solution at a target concentration of 20 mg/g of Compound A. The formulation comprises Compound A, SBEβCD (Captisol, sulfobutyle-ther-β-cyclodextrin) or HPβCD (2-hydroxypropyl-β-cyclo-dextrin), hydrochloric acid (as needed), sodium hydroxide (as needed), and water. Compound A is added to an aqueous solution of SBEβCD or HPβCD, and the pH adjusted to 4.2±0.1 using hydrochloric acid/or sodium hydroxide. The Compound A solution is then filtered through a 0.2 µm membrane filter to yield the final solution formulation.

Table 2 describes the composition of Compound A intravenous solution formulations, at about 20 mg/g.

TABLE 2

| Formulation | Excipient | Compound A concentration [mg/g]$^a$ | pH | Osmolarity [mOsm/Kg] |
|---|---|---|---|---|
| 3A | 2.5% SBEβCD | 16.98 | 4.21 | 584 |
| 3B | 5% SBEβCD | 18.16 | 4.25 | 796 |
| 3C | 10% SBEβCD | 19.34 | 4.26 | 854 |
| 3D | 2.5% HPβCD | 19.03 | 4.29 | 527 |
| 3E | 5% HPβCD | 17.62 | 4.27 | 599 |
| 3F | 10% HPβCD | 19.06 | 4.24 | 659 |

$^a$as determined by HPLC.

Turbid solutions are observed for all formulations.

The solution formulations can be stored at ambient temperature for up to 1 week with no visible changes.

Example 5: Oral Solution Formulations

Compound A is formulated as a solution at a target concentration of ca. 40-45 mg/g of Compound A. A stock solutions of ca. 75 mg/g Compound A in a 2:1 mixture of PEG400:propylene glycol, pH 0.5 was diluted into aqueous vehicles to arrive at the final solution formulations. After addition of the stock solution, the pH of the formulation was adjusted to ca. 3.0-4.0 using NaOH. No precipitation was observed upon pH adjustment.

Table 5 describes the composition of Compound A solution formulations, at about 40-45 mg/g.

TABLE 5

| Formulation | Formulation Composition | pH |
| --- | --- | --- |
| 6A | 40% PEG400, 20% PG, 5% Vitamin E TPGS | 3.36 |
| 6B | 40% PEG400, 20% PG, 5% Vitamin E TPGS + 0.1% HPMC 606 | 3.21 |
| 6C | 40% PEG400, 20% PG, 5% Vitamin E TPGS + 0.1% Soluplus | 2.98 |
| 6D | 40% PEG400, 20% PG, 10% SBEβCD | 3.67 |
| 6E | 40% PEG400, 20% PG, 10% SBEβCD + 0.1% HPMC 606 | 3.10 |
| 6F | 40% PEG400, 20% PG, 10% SBEβCD + 0.1% Poloxamer 407 | 3.63 |
| 6G | 40% PEG400, 20% PG, 20% SBEβCD | 3.96 |

Additional formulations of Compound A at a target concentration of ca. 40-45 mg/g of Compound A were prepared as per Table 6 by dissolving Compound A directly into the vehicle.

TABLE 6

| Formulation | Formulation Composition |
| --- | --- |
| 6H | 30% SBEβCD + 0.1% HPMC 606 |
| 6I | 0.1M HCl |

The examples and embodiments described herein are for illustrative purposes only and various modifications or changes suggested to persons skilled in the art are to be included within the spirit and purview of this application and scope of the appended claims.

What is claimed is:

1. A process for the preparation of Formula 15:

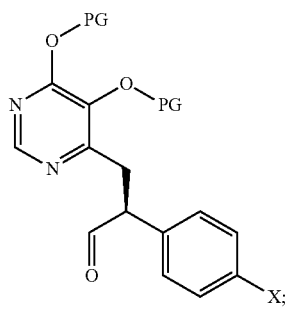

Formula 15 wherein X is halogen, —OTf, —OTs, or —OMs; and
each PG is methyl, benzyl, p-methoxybenzyl, methoxymethyl, [2-(trimethylsilyl)ethoxylmethyl, triisopropylsilyl, or tert-butyldimethylsilyl; comprising:
(1) contacting the compound of Formula 14:

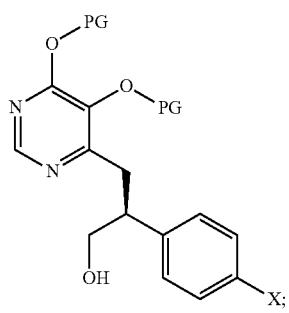

Formula 14 wherein X is halogen, —OTf, —OTs, or —OMs; and
each PG is methyl, benzyl, p-methoxybenzyl, methoxymethyl, [2-(trimethylsilyl)ethoxylmethyl, triisopropylsilyl, or tert-butyldimethylsilyl;
with a suitable oxidation reagent system in a suitable solvent to provide a compound of Formula 15;
wherein:
the suitable oxidation reagent system of step (1) is Collins reagent, pyridinium dichromate, pyridinium chlorochromate, Dess-Martin periodinane, 2-iodobenzoic acid, a TPAP/NMO system, or a TEMPO/bleach system; and
the suitable solvent of step (1) is acetonitrile, dimethylsulfoxide, dichloromethane, chloroform, dichloroethane, hexanes, ethyl acetate, acetic acid, toluene, water, or a combination thereof.

2. The process of claim 1, wherein:
the suitable oxidation reagent system of step (1) is a TEMPO/bleach system; and
the suitable solvent of step (1) is acetonitrile, dichloromethane, chloroform, dichloroethane, hexanes, water, or a combination thereof;
step (1) is performed at a temperature of from about 0° C. to about 5° C.;
each PG is benzyl, p-methoxybenzyl, methoxymethyl, [2-(trimethylsilyl)ethoxy]methyl, triisopropylsilyl, or tert-butyldimethylsilyl; and
X is Cl, Br, or I.

3. The process of claim 1, wherein the compound of Formula 14 is prepared by:
(1a) contacting a compound of Formula 13:

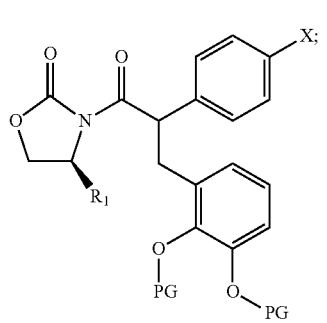

Formula 13 wherein X is halogen, —OTf, —OTs, or —OMs;
$R_1$ is $C_1$-$C_{10}$ alkyl, aryl, or benzyl; and
each PG is methyl, benzyl, p-methoxybenzyl, methoxymethyl, [2-(trimethylsilyl)ethoxylmethyl, triisopropylsilyl, or tert-butyldimethylsilyl;
with a suitable borohydride reagent in a suitable solvent to provide the compound of Formula 14;

wherein:
the suitable borohydride reagent of step (1a) is lithium borohydride, sodium borohydride, sodium cyanoborohydride, potassium borohydride, lithium triethylborohydride, or sodium triacetoxyborohydride;
the suitable solvent of step (1a) is acetonitrile, methanol, ethanol, isopropyl alcohol, dimethoxyethane, 2-methyltetrahydrofuran, methyl tert-butyl ether, cyclopentyl methyl ether, tetrahydrofuran, diethyl ether, diisopropyl ether, 1,4-dioxane, toluene, water, or a combination thereof.

4. The process of claim 3, wherein:
the suitable borohydride reagent of step (1a) is lithium borohydride;
the suitable solvent of step (1a) is a mixture of tetrahydrofuran and ethanol;
step (1a) is performed at a temperature of from about 0° C. to about 25° C.; and
$R_1$ is methyl, isopropyl, tert-butyl, phenyl, or benzyl.

5. The process of claim 3, further comprising crystallizing the compound of Formula 14 from acetonitrile, methanol, ethanol, isopropyl alcohol, acetone, methyl acetate, ethyl acetate, dichloromethane, chloroform, diethyl ether, diisopropyl ether, tert-butyl methyl ether, tetrahydrofuran, 2-methyltetrahydrofuran, dioxane, benzene, toluene, petroleum ether, pentane, hexane, heptane, cyclohexane, acetic acid, water, or a mixture thereof.

6. The process of claim 3, wherein the compound of Formula 13 is prepared by:
(1b) contacting a compound of Formula 12:

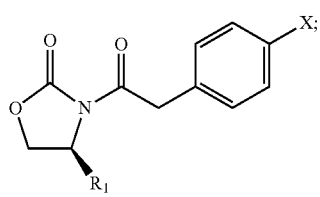

Formula 12 wherein X is halogen, —OTf, —OTs, or —OMs; and
$R_1$ is $C_1$-$C_{10}$ alkyl, aryl, or benzyl;
with a compound of Formula 9:

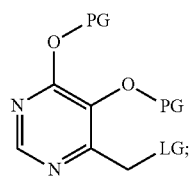

Formula 9 wherein LG is Cl, Br, I, —OTf, —OTs, or —OMs; and
each PG is methyl, benzyl, p-methoxybenzyl, methoxymethyl, [2-(trimethylsilyl)ethoxy]methyl, triisopropylsilyl, or tert-butyldimethylsilyl;
in the presence of a suitable base, and in a suitable solvent, to provide a compound of Formula 13;
wherein:
the suitable base of step (1b) is n-butyl lithium, lithium diisopropylamide (LDA), lithium bis(trimethylsilyl)amide (LiHMDS), or lithium tetramethylpiperidide (LiTMP);

the suitable solvent of step (1b) is diethyl ether, diisopropyl ether, tetrahydrofuran, 2-methyltetrahydrofuran, 1,4-dioxane, tert-butyl methyl ether, cyclopropyl methyl ether, or a combination thereof.

7. The process of claim 6, wherein:
the suitable base of step (1b) is LiHDMS;
the suitable solvent of step (1b) is tetrahydrofuran;
step (1b) is performed at a temperature of about −25 to about −15° C.; and
the compound of Formula 12 is reacted with the base for from about 15 min to about 60 min before the addition of the compound of Formula 9.

8. The process of claim 1, further comprising:
(2) contacting the compound of Formula 15 with a compound of Formula 16, or a salt thereof:

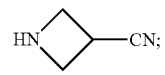

Formula 16 in the presence of a suitable reducing agent in a suitable solvent to provide a compound of Formula 17:

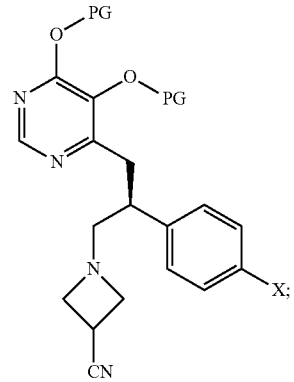

Formula 17 wherein X is halogen, —OTf, —OTs, or —OMs; and
each PG is methyl, benzyl, p-methoxybenzyl, methoxymethyl, [2-(trimethylsilyl)ethoxy]methyl, triisopropylsilyl, or tert-butyldimethylsilyl;
wherein:
the suitable reducing agent of step (2) is sodium borohydride, sodium cyanoborohydride, sodium triacetoxyborohydride, lithium cyanoborohydride, $H_2$/catalyst, or picoline-borane;
the suitable solvent of step (2) is acetonitrile, methanol, ethanol, dichloromethane, chloroform, dichloroethane, toluene, water, or a combination thereof.

9. The process of any claim 8, wherein:
the suitable reducing agent of step (2) is picoline-borane;
the suitable solvent of step (2) is a mixture of methanol and dichloromethane; and
step (2) is performed at a temperature of from about 0° C. to about 25° C.

10. The process of claim 8, further comprising:
(3) contacting the compound of Formula 17 with a compound of Formula 20, or a salt thereof:

Formula 20

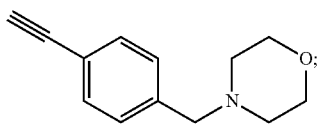

in the presence of a coupling catalyst, a suitable base, and in a suitable solvent to provide a compound of Formula 21:

Formula 21

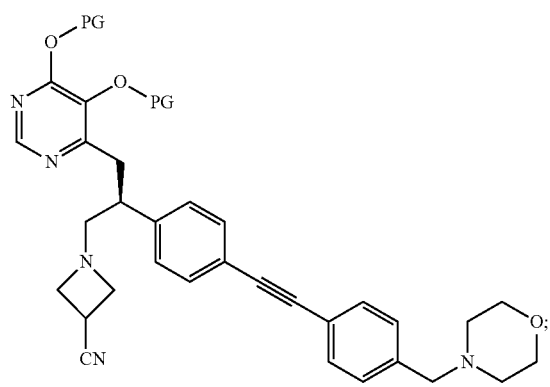

wherein:
each PG is methyl, benzyl, p-methoxybenzyl, methoxymethyl, [2-(trimethylsilyl)ethoxylmethyl, triisopropylsilyl, or tert-butyldimethylsilyl;

the suitable base of step (3) is triethylamine, diisopropylethylamine, 1,2,2,6,6-pentamethylpiperidine, tributylamine, 1,8-diazabicycloundec-7-ene (DBU), sec-butylamine, or tetrabutylammonium fluoride (TBAF); and the suitable solvent of step (3) is acetonitrile, dimethylformamide, diethyl ether, ethanol, tetrahydrofuran, isopropyl alcohol, 1,4-dioxane, toluene, water, or a combination thereof.

11. The process of claim 10, wherein:
the coupling catalyst of step (3) is a palladium catalyst;
the suitable base of step (3) is sec-butylamine or tetrabutylammonium fluoride (TBAF); and
step (3) is performed at a temperature of about 40-45° C.

12. The process of claim 10, further comprising:
(4) contacting the compound of Formula 21 with a suitable reagent in a suitable solvent to provide (S)-1-(3-(5,6-dihydroxypyrimidin-4-yl)-2-(4-((4-(morpholinomethyl)phenyl)ethynyl)phenyl)propyl)azetidine-3-carbonitrile (Compound A):

(Compound A)

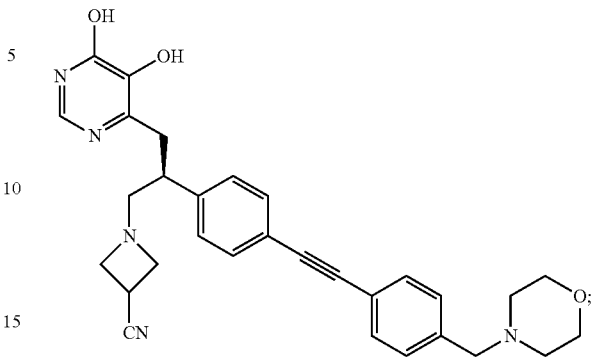

wherein:
the suitable reagent of step (4) is H$_2$/catalyst, HCl, HBr, TFA, TBAF, BCl$_3$, 9-I-BBN, BF$_3$-OEt$_2$, TMS-Cl, or TMS-Br; and the suitable solvent of step (4) is acetonitrile, dichloromethane, chloroform, dichloroethane, diethyl ether, tetrahydrofuran, isopropyl alcohol, 1,4-dioxane, toluene, anisole, water, or a combination thereof.

13. The process of claim 12, wherein:
PG is benzyl;
the suitable reagent of step (4) is TFA; and
the suitable solvent of step (4) is anisole.

14. The process of claim 12, further comprising crystallizing Compound A from acetonitrile, methanol, ethanol, isopropyl alcohol, acetone, methyl acetate, ethyl acetate, dichloromethane, chloroform, diethyl ether, diisopropyl ether, tert-butyl methyl ether, tetrahydrofuran, 2-methyltetrahydrofuran, dioxane, benzene, toluene, petroleum ether, pentane, hexane, heptane, cyclohexane, acetic acid, water, or a mixture thereof.

15. The process of claim 10, wherein the compound of Formula 21 is Compound 21A:

(Compound 21A)

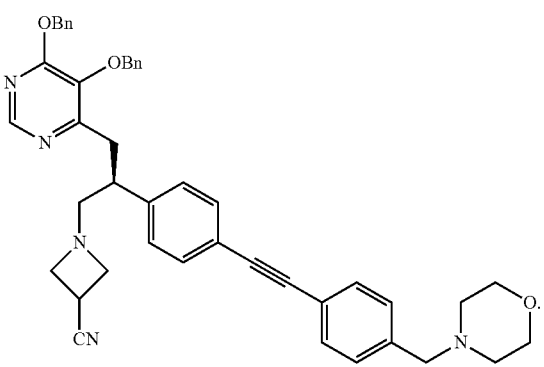 [SMILES: N#CC1CN(C[C@@H](Cc2ncnc(OCc3ccccc3)c2OCc2ccccc2)c2ccc(C#Cc3ccc(CN4CCOCC4)cc3)cc2)C1]

16. A reaction mixture comprising a compound of Formula 14:

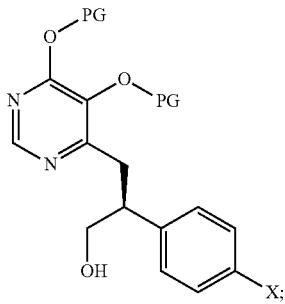

Formula 14 wherein X is halogen, —OTf, —OTs, or —OMs; and each PG is methyl, benzyl, p-methoxybenzyl, methoxymethyl, [2-(trimethylsilyl)ethoxy]methyl, triisopropylsilyl, or tert-butyldimethylsilyl;

an oxidation reagent system comprising TEMPO and NaClO (bleach); and a solvent comprising acetonitrile, dichloromethane, chloroform, dichloroethane, hexanes, water, or a combination thereof.

17. A reaction mixture comprising a compound of Formula 17:

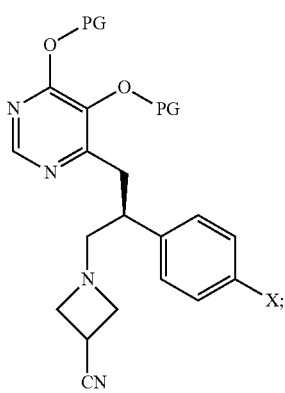

Formula 17 wherein X is halogen, —OTf, —OTs, or —OMs; and each PG is methyl, benzyl, p-methoxybenzyl, methoxymethyl, [2-(trimethylsilyl)ethoxy]methyl, triisopropylsilyl, or tert-butyldimethylsilyl;

a palladium catalyst;

sec-butyl amine; and a solvent comprising acetonitrile, dimethylformamide, diethyl ether, ethanol, tetrahydrofuran, isopropyl alcohol, 1,4-dioxane, toluene, water, or a combination thereof.

18. A compound selected from:

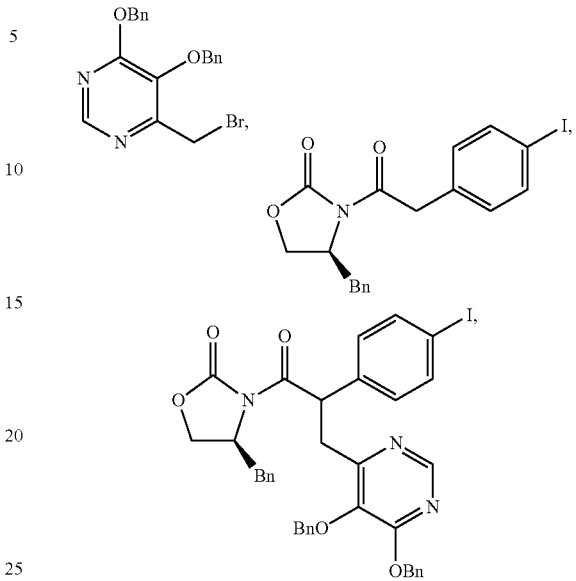

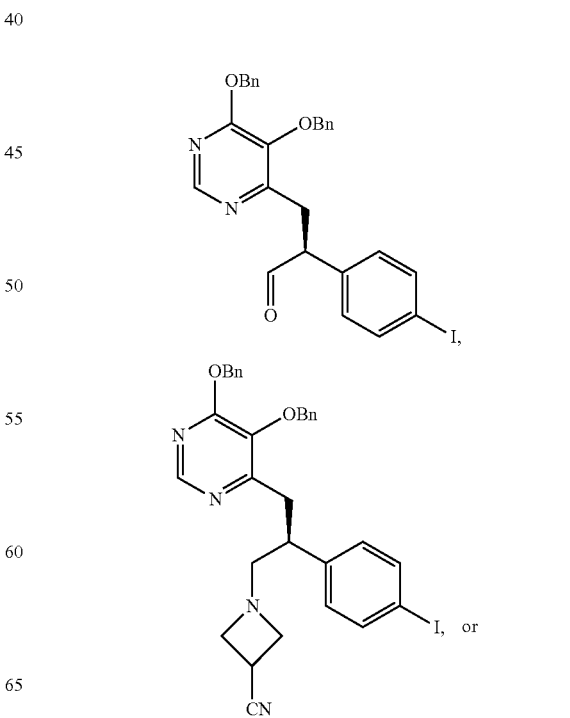

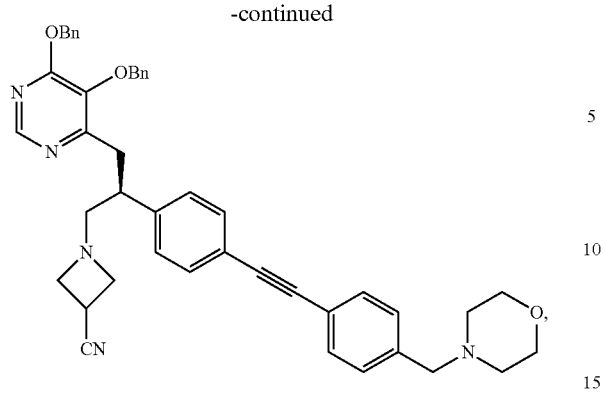
or a salt thereof.